(12) United States Patent
Pallisse Bergwerf et al.

(10) Patent No.: US 10,100,080 B2
(45) Date of Patent: Oct. 16, 2018

(54) SPLIT INTEINS AND USES THEREOF

(71) Applicant: ERA BIOTECH, S.A., Barcelona (ES)

(72) Inventors: Roser Pallisse Bergwerf, Valldoreix (ES); Stefan Robert Schmidt, Laupheim (DE); Didac Marco Feliu, Barcelona (ES); Patricia Karina Carvajal Vallejos, Barcelona (ES)

(73) Assignee: ERA BIOTECH, S.A., Cerdanyola Del Vallès, Barcelona (ES)

( * ) Notice: Subject to any disclaimer, the term of this patent is extended or adjusted under 35 U.S.C. 154(b) by 156 days.

(21) Appl. No.: 14/348,132

(22) PCT Filed: Sep. 28, 2012

(86) PCT No.: PCT/EP2012/069219
§ 371 (c)(1),
(2) Date: Mar. 28, 2014

(87) PCT Pub. No.: WO2013/045632
PCT Pub. Date: Apr. 4, 2013

(65) Prior Publication Data
US 2015/0232507 A1 Aug. 20, 2015

Related U.S. Application Data

(60) Provisional application No. 61/540,101, filed on Sep. 28, 2011.

(30) Foreign Application Priority Data

Jun. 13, 2012 (EP) .................... 12171848

(51) Int. Cl.
*C07K 2/00* (2006.01)
*C12P 21/06* (2006.01)

(52) U.S. Cl.
CPC ............ *C07K 2/00* (2013.01); *C12P 21/06* (2013.01)

(58) Field of Classification Search
None
See application file for complete search history.

(56) References Cited

U.S. PATENT DOCUMENTS

| | | | |
|---|---|---|---|
| 5,580,759 | A | 12/1996 | Yang et al. |
| 6,096,551 | A | 8/2000 | Barbas et al. |
| 7,575,860 | B2 | 8/2009 | Evans et al. |
| 2003/0194809 | A1 | 10/2003 | Yadav et al. |
| 2004/0077842 | A1 | 4/2004 | Himawan |
| 2004/0096938 | A1 | 5/2004 | Xu et al. |
| 2006/0141570 | A1 | 6/2006 | Wood et al. |
| 2007/0092937 | A1 | 4/2007 | Togi et al. |
| 2007/0207502 | A1 | 9/2007 | Benkovic et al. |
| 2011/0136170 | A1 | 6/2011 | Chen et al. |

FOREIGN PATENT DOCUMENTS

| | | |
|---|---|---|
| EP | 1621556 A1 | 2/2006 |
| EP | 2295596 A1 | 3/2011 |
| JP | 2003505012 A | 2/2003 |
| JP | 2003534768 A | 11/2003 |
| JP | 2004515233 A | 5/2004 |
| WO | 0070023 | 11/2000 |

OTHER PUBLICATIONS

Brenzel et al ('Engineering artificially split inteins for applications in protein chemistry: biochemical characterization of the split SSp DnaB intein and comparison to the split Sce VMA intein' Biochemistry v45 2006 pp. 1571-1578).*
Supplement to Dassa et al ('Fractured genes: a novel arrangement involving new split inteins and a new homing endonuclease family' Nucleic Acids Research v37(8) May 2009, the supplement is a total of 11 pages).*
Southworth et al. ('An alternative protein splicing mechanism for inteins lacking an N-terminal nucleophile' The EMBO Journal v19(18) 2000 pp. 5019-5026).*
Altschul S. F. et al., "Gapped BLAST and PSI-BLAST: a new generation of protein database search programs," Nucleic Acids Res, 1997, vol. 25:3389-3402.
Amitai, G. et al., "Modulation of intein activity by its neighboring extein substrates," Proceedings of the National of Academy Sciences, 2009, vol. 106 (27): 11005-11010.
Appleby J. H. et al., "Novel Split Intein for trans-Splicing Synthetic Peptide onto C Terminus of Protein," J. Biol. Chem., 2009, vol. 284:6194-6199.
Arnold U., "Incorporation of non-natural modules into proteins: structural features beyond the genetic code," Biotechnol Lett, 2009, vol. 31:1129-1139.
Aslanidis C. et al., "Ligation-independent cloning of PCR products (LIC-PCR)," Nucl. Acids Res., 1990, vol. 18:6069-74.
Benfey P. N. et al., "Regulated Genes in Trasngenic Plants," Science, 1989, vol. 244:174-181.
Binschik J. et al., "Photocontrol of Protein Activity Mediated by the Cleavage Reaction of a Split Intein," Angewandte Chemie International Ed., 2011, 50(14):3249-3252.
Blanusa M. et al, "Phosphorothioate-based ligase-independent gene cloning (PLICing): An enzyme-free and sequence-independent cloning method," Anal. Biochem., 2010, vol. 406: 141-146.
Carvajal-Vallejos, P. et al., "Unprecedented Rates and Efficiencies Revealed for New Natural Split Inteins from Metagenomic Sources," Journal of Biological Chemistry, 2012, vol. 287 (34): 28686-28696.
Caspi et al., "Distribution of split DnaE inteins in cyanobacteria," Mol Microbiol., 2003, vol. 50:1569-1577.

(Continued)

*Primary Examiner* — Karlheinz R. Skowronek
*Assistant Examiner* — Ronald T Niebauer
(74) *Attorney, Agent, or Firm* — Tristan A. Fuierer; Moore & Van Allen, PLLC

(57) ABSTRACT

The present invention relates generally to robust split inteins. The split inteins described herein are active over a large temperature range, including temperatures as low as 0° C., over a wide pH range, and in the presence of chaotropic salts. The split inteins also show high tolerance to sequence variability in fused heterologous polypeptides and therefore are useful in protein purification and engineering techniques.

Figure 1:
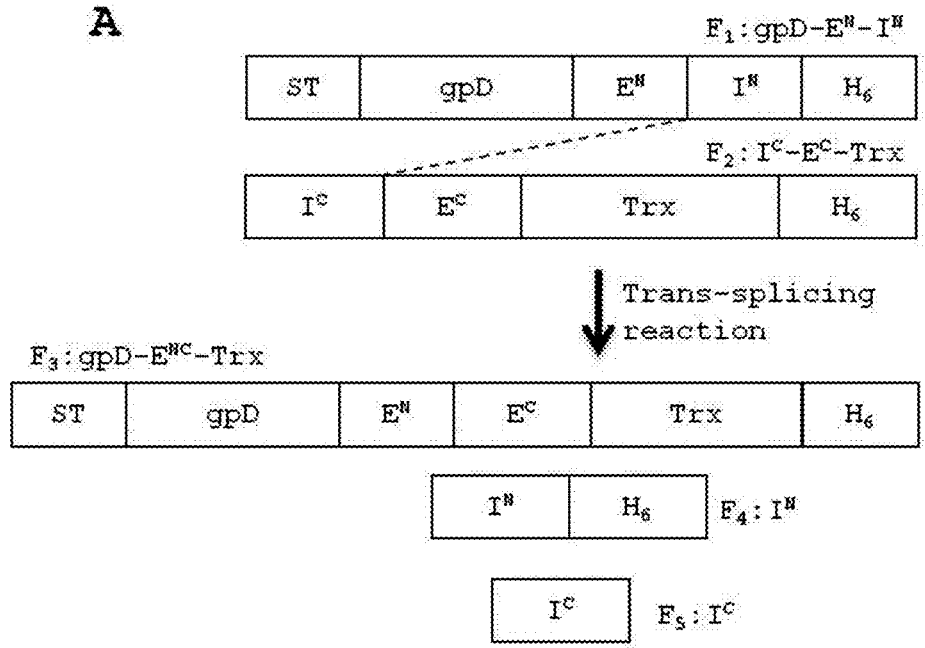
Figure 1:
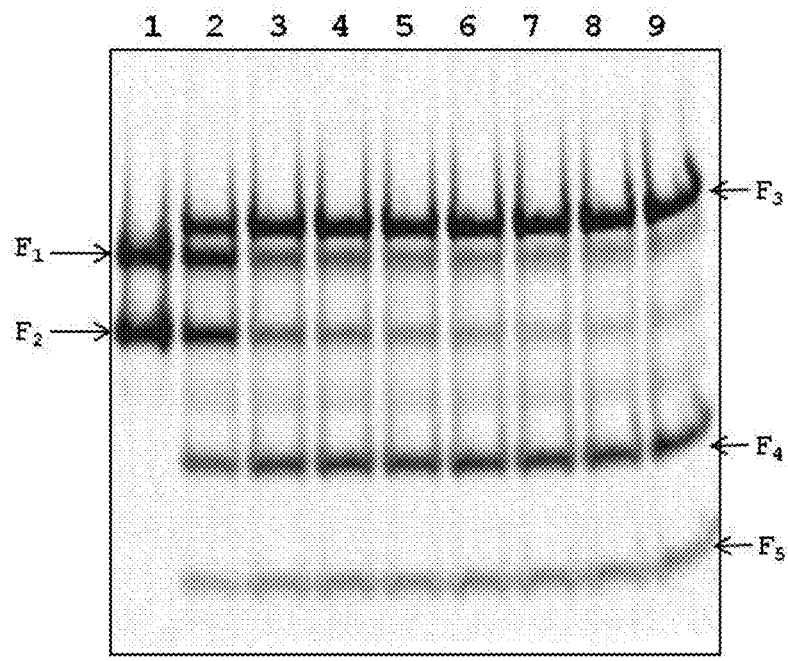

14 Claims, 3 Drawing Sheets
Specification includes a Sequence Listing.

(56) References Cited

OTHER PUBLICATIONS

Charalambous A. et al., "Intein-mediated site-specific conjugation of Quantum Dots to proteins in vivio," J. Nanobiotechnology, 2009, vol. 7:9.
Choi J. et al., "Protein Trans-splicing and Characterization of a Split Family B-type DNA Polymerase from the Hyperthermophilic Archaeal Parasite Nanoarchaeum equitans," J Mol Biol., 2006, vol. 356:1093-1106.
Chong S. et al., "Protein Splicing of the *Saccharomyces cerevisiae* VMA Intein without the Endonuclease Motifs," J. Biol. Chem., 1997, vol. 272:15587-15589.
Dassa B. et al., "Trans Protein Splicing of Cyanobacterial Split Inteins in Endogenous and Exogenous Combinations," Biochemistry, 2007, vol. 46:322-330.
Dassa B. et al., "Fractured genes: a novel genomic arrangement involving new split inteins and a new homing endonuclease family," Nucleic Acids Res., 2009, vol. 37:2560-2573.
Derbyshire V. et al., "Genetic definition of a protein-splicing domain: Functional mini-inteins support structure predictions and a model for intein evolution," Proc. Natl. Acad. Sci. USA., 1997, vol. 94:11466-11471.
Dhar, T. et al., "Modification of transmembrane and GPI-anchored proteins on living cells by efficient protein trans-splicing using the Npu DnaE intein," Chemical Communications, 2011, vol. 47 (11): 3063.
Elleuche, S. et al., "Inteins, valuable genetic elements in molecular biology and biotechnology," Applied Microbiology and Biotechnology, 2010, vol. 87 (2): 479-489.
Evans T. et al., "Protein Splicing Elements and Plants: From Transgene Containment to Protein Purification," Annu. Rev. Plant Biol., 2005, vol. 56:375-392.
Evans T. et al., "Intein-Mediated Protein Ligation: Harnessing Nature's Escape Artists," Biopolymers, 1999, vol. 51:333-342.
Iwai I. et al., "Highly efficient protein trans-splicing by a naturally split DnaE intein from Nostoc punctiforme," FEBS Letters, 2006, vol. 580:1853-1858.
Jeffries, Cy. M. et al., "Stabilization of a binary protein complex by intein-mediated cyclization," Protein Science, 2006: vol. 15 (11): 2612-2618.
Karlin S. et al., "Methods for assessing the statistical significance of molecular sequence features by using general scoring schemes," Proc. Natl. Acad. Sci. USA, 1990. vol. 87:2264-2268.
Karlin S. et al., "Applications and statistics for multiple high-scoring segments in molecular sequences," Proc. Natl. Acad. Sci. USA, 1993, vol. 90:5873-5877.
Lew B. et al., "Characteristics of Protein Splicing in trans Mediated by a Semisynthetic Split Intein," Biopolymers, 1999, vol. 51:355-362.
Liu X. et al., "Split dnaE Genes Encoding Multiple Novel Inteins in Trichodesmium erythraeum," J. Biol. Chem., 2003, vol. 278:26315-26318.
Liu Z., "Hetero-stagger cloning: efficient and rapid cloning of PCR products," Nucl. Acids Res., 1996, vol. 24: 2458-2459.
Liu XQ "Protein-Splicing Intein: Genetic Mobility, Origin, and Evolution," Ann. Rev. Genet., 2000, vol. 34:61-76.
Lu W. et al, "Split intein facilitated tag affinity purification for recombinant proteins with controllable tag removal by inducible auto-cleavage," J. Chromatography A., 2011, vol. 1218:2553-2560.
Martin D. D. et al. "Characterization of a Naturally Occurring Trans-Splicing Intein from *Synechocystis* sp. PCC6803," Biochemistry, 2001, vol. 40:1393-1402.
Matteucci et al., "Synthesis of Deoxyoligonucleotides on a Polymer Support," J. Am. Chem. Soc., 1981, vol. 103:3185.
Mohlmann, S. et al., "Site-specific modification of ED-B-targeting antibody using intein-fusion technology," BMC Biotechnology, 2011, vol. 11 (1): 76.
Mootz, H. D. et al., "Split Inteins as Versatile Tools for Protein Semisynthesis," Chembiochem, 2009, vol. 10 (16): 2579-2589.
Muir T. et al., "Expressed protein ligation: A general method for protein engineering," Proc. Natl. Acad. Sci. USA, 1998, vol. 95:6705-6710.
Nilsen I. W. et al, "Isolation of cmr, a Novel *Escherichia coli* Chloramphenicol Resistance Gene Encoding a Putative Efflux Pump," J. Bacteriol., 1996, vol. 178: 3188-3193.
Oeemig J. et al., "Solution structure of DnaE intein from Nostoc punctiforme: Structural basis for the design of a new split intein suitable for site-specific chemical modification," FEBS Letters, 2009, vol. 583:1451-1456.
Ozawa T. et al., "A genetic approach to identifying mitochondrial proteins," Nat. Biotechnol., 2003, vol. 21:287-293.
Paszkowski et al., "Direct gene transfer to plants," EMBO J., 1989, vol. 3:2719.
Perler F et al., "Protein splicing elements: inteins and exteins—a definition of terms and recommended nomenclature," Nucleic Acids Res., 1994, 22:1125-1127.
Perler F., "InBase: the Intein Database," Nucl. Acids Res., 2002, vol. 30: 383-384.
Severinov K. et al., "Expressed Protein Ligation, a Novel Method for Studying Protein-Protein Interactions in Transcription," J. Biol. Chem., 1998, vol. 273:16205-16209.
Seyedsayamdost M. et al., "Site-specific incorporation of fluorotyrosines into the R2 subunit of *E. coli* ribonucleotide reductase by expressed protein ligation," Nat. Protoc., 2007, vol. 2:1225-1235.
Shah, N. H. et al., "Ultrafast Protein Splicing is Common among Cyanobacterial Split Inteins: Implications for Protein Engineering," Journal of the American Chemical Society, 2012, vol. 134 (28): 11338-11341.
Shingledecker K. et al. "Molecular dissection of the Mycobacterium tuberculosis RecA intein: design of a minimal intein and of a trans-splicing system involving two intein fragments," Gene, 1998, vol. 207:187-195.
Smith T.F. et al., "Comparison of Biosequences," Advances in Applied Mathematics, 1981, vol. 2: 482-489.
Vijayalakshmi B. et al., "Affinity chromatography as a tool for antibody purifcation," Methods, 2012, vol. 56(2): 116-129.
Wu H. et al., "Protein trans-splicing by a split intein encoded in a split DnaE gene of *Synechocystis* sp. PCC6803," Proc. Natl. Acad. Sci. USA. 1998, vol. 95:9226-9231.
Xu, M. Q. et al., "The mechanism of protein splicing and its modulation by mutation," EMBO J., 1996, vol. 15:5146-5153.
Zettler J. et al., "The naturally split Npu DnaE intein exhibits an extraordinarily high rate in the protein trans-splicing reaction," FEBS Letters, 2009, vol. 583:909-914.
Zuger S. et al., "Intein-based biosynthetic incorporation of unlabeled protein tags into isotopically labeled proteins for NMR studies," Nat. Biotechnol., 2005, vol. 23:736-740.
International Search Report dated Jan. 2, 2013.
Mathys, Sibyllc, et al.; "Characterization of self-splicing mini-intein and its conversion into autocatalytic N- and C-terminal cleavage elements: facile production of protein building blocks for protein ligation," Gene, 1999, pp. 1-13, vol. 231.

* cited by examiner (A) Trans-splicing reaction (B) C-terminal self-cleavage reaction (C) N-terminal self-cleavage reaction

SEQUENCE LISTING

<160> NUMBER OF SEQ ID NOS: 108

<210> SEQ ID NO 1
<211> LENGTH: 678
<212> TYPE: DNA
<213> ORGANISM: Artificial Sequence
<220> FEATURE:
<223> OTHER INFORMATION: GP-41.1 N-fragment DNA

<400> SEQUENCE: 1
ccatggccag ttggagccac ccgcagttcg aaaaagcgag caaagaaacc tttacccatt    60

-continued

```
accagccgca gggcaacagt gacccggctc ataccgcaac cgcgcccggc ggattgagtg    120
cgaaagcgcc tgcaatgacc ccgctgatgc tggacacctc cagccgtaag ctggttgcgt    180
gggatggcac caccgacggt gctgccgttg cattcttgc ggttgctgct gaccagacca     240
gcaccacgct gacgttctac aagtccggca cgttccgtta tgaggatgtg ctctggccgg    300
aggctgccag cgacgagacg aaaaaacgga ccgcgtttgc cggaacggca atcagcatcg    360
ttggatccac ccgtagcggt tattgcctgg acctgaaaac ccaggtgcag accccgcagg    420
gcatgaagga gattagcaac attcaggtgg gcgacctggt tctgagcaac accggctata    480
atgaggtgct gaacgtgttc ccgaagagca aaaagaagag ctacaagatc acgctggagg    540
acggcaagga aatcatttgc agcgaagaac atctgtttcc gacccagacc ggcgaaatga    600
atattagcgg tggcctgaaa gaaggcatgt gcctgtatgt gaaagagggc ggtcaccacc    660
atcatcacca ctaagctt                                                 678
```

<210> SEQ ID NO 2
<211> LENGTH: 223
<212> TYPE: PRT
<213> ORGANISM: Artificial Sequence
<220> FEATURE:
<223> OTHER INFORMATION: GP-41.1 N-fragment Protein

<400> SEQUENCE: 2

```
Met Ala Ser Trp Ser His Pro Gln Phe Glu Lys Ala Ser Lys Glu Thr
1               5                   10                  15

Phe Thr His Tyr Gln Pro Gln Gly Asn Ser Asp Pro Ala His Thr Ala
            20                  25                  30

Thr Ala Pro Gly Gly Leu Ser Ala Lys Ala Pro Ala Met Thr Pro Leu
        35                  40                  45

Met Leu Asp Thr Ser Ser Arg Lys Leu Val Ala Trp Asp Gly Thr Thr
    50                  55                  60

Asp Gly Ala Ala Val Gly Ile Leu Ala Val Ala Ala Asp Gln Thr Ser
65                  70                  75                  80

Thr Thr Leu Thr Phe Tyr Lys Ser Gly Thr Phe Arg Tyr Glu Asp Val
                85                  90                  95

Leu Trp Pro Glu Ala Ala Ser Asp Glu Thr Lys Lys Arg Thr Ala Phe
            100                 105                 110

Ala Gly Thr Ala Ile Ser Ile Val Gly Ser Thr Arg Ser Gly Tyr Cys
        115                 120                 125

Leu Asp Leu Lys Thr Gln Val Gln Thr Pro Gln Gly Met Lys Glu Ile
    130                 135                 140

Ser Asn Ile Gln Val Gly Asp Leu Val Leu Ser Asn Thr Gly Tyr Asn
145                 150                 155                 160

Glu Val Leu Asn Val Phe Pro Lys Ser Lys Lys Ser Tyr Lys Ile
                165                 170                 175

Thr Leu Glu Asp Gly Lys Glu Ile Ile Cys Ser Glu Glu His Leu Phe
            180                 185                 190

Pro Thr Gln Thr Gly Glu Met Asn Ile Ser Gly Gly Leu Lys Glu Gly
        195                 200                 205

Met Cys Leu Tyr Val Lys Glu Gly Gly His His His His His
    210                 215                 220
```

<210> SEQ ID NO 3
<211> LENGTH: 88
<212> TYPE: PRT

```
<213> ORGANISM: Artificial Sequence
<220> FEATURE:
<223> OTHER INFORMATION: GP 41.1 (InteinN)

<400> SEQUENCE: 3

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Ser Tyr Lys
        35                  40                  45

Ile Thr Leu Glu Asp Gly Lys Glu Ile Ile Cys Ser Glu Glu His Leu
    50                  55                  60

Phe Pro Thr Gln Thr Gly Glu Met Asn Ile Ser Gly Gly Leu Lys Glu
65                  70                  75                  80

Gly Met Cys Leu Tyr Val Lys Glu
                85

<210> SEQ ID NO 4
<211> LENGTH: 5
<212> TYPE: PRT
<213> ORGANISM: Artificial Sequence
<220> FEATURE:
<223> OTHER INFORMATION: GP 41.1 (ExteinN)

<400> SEQUENCE: 4

Thr Arg Ser Gly Tyr
1               5

<210> SEQ ID NO 5
<211> LENGTH: 520
<212> TYPE: DNA
<213> ORGANISM: Artificial Sequence
<220> FEATURE:
<223> OTHER INFORMATION: GP41.1 C-fragment DNA

<400> SEQUENCE: 5
catatgggca aaacagcat gatgctgaag aagatcctga agatcgagga gctggacgag      60
cgcgagctga ttgatatcga agtgagcggc aaccacctgt tctacgccaa tgacattctg    120
acgcataata gcagcagcga tgtgggtacc ggatctgata aaattattca tctgactgat    180
gattcttttg atactgatgt acttaaggca gatggtgcaa tcctggttga tttctgggca    240
cactggtgcg gtccgtgcaa aatgatcgct ccgattctgg atgaaatcgc tgacgaatat    300
cagggcaaac tgaccgttgc aaaactgaac atcgatcaca cccgggcac tgcgccgaaa    360
tatggcatcc gtggtatccc gactctgctg ctgttcaaaa acggtgaagt ggcggcaacc    420
aaagtgggtg cactgtctaa aggtcagttg aaagagttcc tcgacgctaa cctggccggc    480
tctgaattca gatctcatca ccatcaccat cactaagctt                          520

<210> SEQ ID NO 6
<211> LENGTH: 170
<212> TYPE: PRT
<213> ORGANISM: Artificial Sequence
<220> FEATURE:
<223> OTHER INFORMATION: GP41.1 C-fragment Protein

<400> SEQUENCE: 6

Met Gly Lys Asn Ser Met Met Leu Lys Lys Ile Leu Lys Ile Glu Glu
1               5                   10                  15

Leu Asp Glu Arg Glu Leu Ile Asp Ile Glu Val Ser Gly Asn His Leu
```

```
                    20                  25                  30
Phe Tyr Ala Asn Asp Ile Leu Thr His Asn Ser Ser Asp Val Gly
            35                  40                  45

Thr Gly Ser Asp Lys Ile Ile His Leu Thr Asp Ser Phe Asp Thr
    50                  55                  60

Asp Val Leu Lys Ala Asp Gly Ala Ile Leu Val Asp Phe Trp Ala His
65                  70                  75                  80

Trp Cys Gly Pro Cys Lys Met Ile Ala Pro Ile Leu Asp Glu Ile Ala
                85                  90                  95

Asp Glu Tyr Gln Gly Lys Leu Thr Val Ala Lys Leu Asn Ile Asp His
            100                 105                 110

Asn Pro Gly Thr Ala Pro Lys Tyr Gly Ile Arg Gly Ile Pro Thr Leu
            115                 120                 125

Leu Leu Phe Lys Asn Gly Glu Val Ala Ala Thr Lys Val Gly Ala Leu
        130                 135                 140

Ser Lys Gly Gln Leu Lys Glu Phe Leu Asp Ala Asn Leu Ala Gly Ser
145                 150                 155                 160

Glu Phe Arg Ser His His His His His His
                165                 170

<210> SEQ ID NO 7
<211> LENGTH: 37
<212> TYPE: PRT
<213> ORGANISM: Artificial Sequence
<220> FEATURE:
<223> OTHER INFORMATION: GP 41.1 (InteinC)

<400> SEQUENCE: 7

Met Met Leu Lys Lys Ile Leu Lys Ile Glu Glu Leu Asp Glu Arg Glu
1               5                   10                  15

Leu Ile Asp Ile Glu Val Ser Gly Asn His Leu Phe Tyr Ala Asn Asp
            20                  25                  30

Ile Leu Thr His Asn
        35

<210> SEQ ID NO 8
<211> LENGTH: 5
<212> TYPE: PRT
<213> ORGANISM: Artificial Sequence
<220> FEATURE:
<223> OTHER INFORMATION: GP 41.1 (ExteinC)

<400> SEQUENCE: 8

Ser Ser Ser Asp Val
1               5

<210> SEQ ID NO 9
<211> LENGTH: 5
<212> TYPE: PRT
<213> ORGANISM: Artificial Sequence
<220> FEATURE:
<223> OTHER INFORMATION: E coli enhancer

<400> SEQUENCE: 9

Met Gly Lys Asn Ser
1               5

<210> SEQ ID NO 10
<211> LENGTH: 681
<212> TYPE: DNA
<213> ORGANISM: Artificial Sequence
```

<220> FEATURE:
<223> OTHER INFORMATION: GP 41.8 N-fragment DNA

<400> SEQUENCE: 10

```
ccatggccag ttggagccac ccgcagttcg aaaaagcgag caaagaaacc tttacccatt      60
accagccgca gggcaacagt gacccggctc ataccgcaac cgcgcccggc ggattgagtg     120
cgaaagcgcc tgcaatgacc ccgctgatgc tggacacctc cagccgtaag ctggttgcgt     180
gggatggcac caccgacggt gctgccgttg cattcttgc ggttgctgct gaccagacca      240
gcaccacgct gacgttctac aagtccggca cgttccgtta tgaggatgtg ctctggccgg     300
aggctgccag cgacgagacg aaaaaacgga ccgcgtttgc cggaacggca atcagcatcg     360
ttggatccag ccaactgaat cgttgcctga gcctggatac gatggttgtg accaatggca     420
aagcgattga gattcgtgat gtgaaagtgg gcgattggct ggaaagcgaa tgtgccccgg     480
tgcaggtgac cgaagtgctg ccgattatca agcagccggt gtttgaaatt gtgctgaaga     540
gcggcaaaaa gatccgtgtg agcgcgaatc ataaattccc gaccaaagat ggcctgaaaa     600
ccatcaatag cggtctgaaa gttggcgact tcctgcgtag ccgtgcgaaa ggcggccatc     660
atcaccacca tcactaagct t                                               681
```

<210> SEQ ID NO 11
<211> LENGTH: 224
<212> TYPE: PRT
<213> ORGANISM: Artificial Sequence
<220> FEATURE:
<223> OTHER INFORMATION: GP 41.8 N-fragment PROTEIN

<400> SEQUENCE: 11

```
Met Ala Ser Trp Ser His Pro Gln Phe Glu Lys Ala Ser Lys Glu Thr
1               5                   10                  15

Phe Thr His Tyr Gln Pro Gln Gly Asn Ser Asp Pro Ala His Thr Ala
            20                  25                  30

Thr Ala Pro Gly Gly Leu Ser Ala Lys Ala Pro Ala Met Thr Pro Leu
        35                  40                  45

Met Leu Asp Thr Ser Ser Arg Lys Leu Val Ala Trp Asp Gly Thr Thr
    50                  55                  60

Asp Gly Ala Ala Val Gly Ile Leu Ala Val Ala Ala Asp Gln Thr Ser
65                  70                  75                  80

Thr Thr Leu Thr Phe Tyr Lys Ser Gly Thr Phe Arg Tyr Glu Asp Val
                85                  90                  95

Leu Trp Pro Glu Ala Ala Ser Asp Glu Thr Lys Lys Arg Thr Ala Phe
            100                 105                 110

Ala Gly Thr Ala Ile Ser Ile Val Gly Ser Ser Gln Leu Asn Arg Cys
        115                 120                 125

Leu Ser Leu Asp Thr Met Val Val Thr Asn Gly Lys Ala Ile Glu Ile
    130                 135                 140

Arg Asp Val Lys Val Gly Asp Trp Leu Glu Ser Glu Cys Gly Pro Val
145                 150                 155                 160

Gln Val Thr Glu Val Leu Pro Ile Ile Lys Gln Pro Val Phe Glu Ile
                165                 170                 175

Val Leu Lys Ser Gly Lys Lys Ile Arg Val Ser Ala Asn His Lys Phe
            180                 185                 190

Pro Thr Lys Asp Gly Leu Lys Thr Ile Asn Ser Gly Leu Lys Val Gly
        195                 200                 205

Asp Phe Leu Arg Ser Arg Ala Lys Gly Gly His His His His His His
```

<210> SEQ ID NO 12
<211> LENGTH: 89
<212> TYPE: PRT
<213> ORGANISM: Artificial Sequence
<220> FEATURE:
<223> OTHER INFORMATION: GP41.8 (Intein-N)

<400> SEQUENCE: 12

Cys Leu Ser Leu Asp Thr Met Val Val Thr Asn Gly Lys Ala Ile Glu
1               5                   10                  15
Ile Arg Asp Val Lys Val Gly Asp Trp Leu Glu Ser Glu Cys Gly Pro
            20                  25                  30
Val Gln Val Thr Glu Val Leu Pro Ile Ile Lys Gln Pro Val Phe Glu
        35                  40                  45
Ile Val Leu Lys Ser Gly Lys Lys Ile Arg Val Ser Ala Asn His Lys
    50                  55                  60
Phe Pro Thr Lys Asp Gly Leu Lys Thr Ile Asn Ser Gly Leu Lys Val
65                  70                  75                  80
Gly Asp Phe Leu Arg Ser Arg Ala Lys
                85

<210> SEQ ID NO 13
<211> LENGTH: 5
<212> TYPE: PRT
<213> ORGANISM: Artificial Sequence
<220> FEATURE:
<223> OTHER INFORMATION: GP41.8 (Extein-N)

<400> SEQUENCE: 13

Ser Gln Leu Asn Arg
1               5

<210> SEQ ID NO 14
<211> LENGTH: 529
<212> TYPE: DNA
<213> ORGANISM: Artificial Sequence
<220> FEATURE:
<223> OTHER INFORMATION: GP41.8 C-term DNA

<400> SEQUENCE: 14
catatgtgcg agatcttcga gaacgagatc gactgggatg aaatcgcgag cattgagtat      60
gtgggcgttg aggagaccat tgacatcaac gtgacgaacg accgcctgtt cttcgcaaac     120
ggcattctga cccataatag cgcggtggaa gagggtaccg gatctgataa aattattcat     180
ctgactgatg attcttttga tactgatgta cttaaggcag atggtgcaat cctggttgat     240
ttctgggcac actggtgcgg tccgtgcaaa atgatcgctc cgattctgga tgaaatcgct     300
gacgaatatc agggcaaact gaccgttgca aaactgaaca tcgatcacaa cccgggcact     360
gcgccgaaat atggcatccg tggtatcccg actctgctgc tgttcaaaaa cggtgaagtg     420
gcggcaacca agtgggtgc actgtctaaa ggtcagttga agagttcct cgacgctaac     480
ctggccggct ctgaattcag atctcatcac catcaccatc actaagctt               529

<210> SEQ ID NO 15
<211> LENGTH: 173
<212> TYPE: PRT
<213> ORGANISM: Artificial Sequence
<220> FEATURE:
<223> OTHER INFORMATION: GP41.8 PROTEIN

<400> SEQUENCE: 15

Met Cys Glu Ile Phe Glu Asn Glu Ile Asp Trp Asp Glu Ile Ala Ser
1               5                   10                  15

Ile Glu Tyr Val Gly Val Glu Thr Ile Asp Ile Asn Val Thr Asn
            20                  25                  30

Asp Arg Leu Phe Phe Ala Asn Gly Ile Leu Thr His Asn Ser Ala Val
        35                  40                  45

Glu Glu Gly Thr Gly Ser Asp Lys Ile Ile His Leu Thr Asp Asp Ser
    50                  55                  60

Phe Asp Thr Asp Val Leu Lys Ala Asp Gly Ala Ile Leu Val Asp Phe
65                  70                  75                  80

Trp Ala His Trp Cys Gly Pro Cys Lys Met Ile Ala Pro Ile Leu Asp
                85                  90                  95

Glu Ile Ala Asp Glu Tyr Gln Gly Lys Leu Thr Val Ala Lys Leu Asn
            100                 105                 110

Ile Asp His Asn Pro Gly Thr Ala Pro Lys Tyr Gly Ile Arg Gly Ile
        115                 120                 125

Pro Thr Leu Leu Leu Phe Lys Asn Gly Glu Val Ala Ala Thr Lys Val
    130                 135                 140

Gly Ala Leu Ser Lys Gly Gln Leu Lys Glu Phe Leu Asp Ala Asn Leu
145                 150                 155                 160

Ala Gly Ser Glu Phe Arg Ser His His His His His
                165                 170

<210> SEQ ID NO 16
<211> LENGTH: 45
<212> TYPE: PRT
<213> ORGANISM: Artificial Sequence
<220> FEATURE:
<223> OTHER INFORMATION: GP41.8 (InteinC)

<400> SEQUENCE: 16

Met Cys Glu Ile Phe Glu Asn Glu Ile Asp Trp Asp Glu Ile Ala Ser
1               5                   10                  15

Ile Glu Tyr Val Gly Val Glu Thr Ile Asp Ile Asn Val Thr Asn
            20                  25                  30

Asp Arg Leu Phe Phe Ala Asn Gly Ile Leu Thr His Asn
        35                  40                  45

<210> SEQ ID NO 17
<211> LENGTH: 5
<212> TYPE: PRT
<213> ORGANISM: Artificial Sequence
<220> FEATURE:
<223> OTHER INFORMATION: GP41.8 (ExteinC)

<400> SEQUENCE: 17

Ser Ala Val Glu Glu
1               5

<210> SEQ ID NO 18
<211> LENGTH: 729
<212> TYPE: DNA
<213> ORGANISM: Artificial Sequence
<220> FEATURE:
<223> OTHER INFORMATION: NrdJ1 N-term DNA

<400> SEQUENCE: 18
ccatggccag ttggagccac ccgcagttcg aaaaagcgag caaagaaacc tttacccatt    60

```
accagccgca gggcaacagt gacccggctc ataccgcaac cgcgcccggc ggattgagtg    120
cgaaagcgcc tgcaatgacc ccgctgatgc tggacacctc cagccgtaag ctggttgcgt    180
gggatggcac caccgacggt gctgccgttg gcattcttgc ggttgctgct gaccagacca    240
gcaccacgct gacgttctac aagtccggca cgttccgtta tgaggatgtg ctctggccgg    300
aggctgccag cgacgagacg aaaaaacgga ccgcgtttgc cggaacggca atcagcatcg    360
ttggatccgg caccaatccg tgttgcctgg tgggcagcag cgagatcatc acccgtaact    420
acggcaaaac cacgatcaaa gaggtggttg agatcttcga caacgacaag aatatccagg    480
tgctggcgtt caacacccac acggacaata tcgaatgggc cccaattaaa gcggcgcaac    540
tgacccgtcc aaacgcagag ctggtggaac tggaaattaa cccctgcat ggcgtgaaaa    600 ccatccgttg cacccggat catccagtgt ataccaaaaa tcgtgactat gtgcgcgccg    660
atgagctgac cgatgatgat gaactggtgg tggcgattgg cggccatcac caccatcacc    720
actaagctt                                                             729
```

<210> SEQ ID NO 19
<211> LENGTH: 240
<212> TYPE: PRT
<213> ORGANISM: Artificial Sequence
<220> FEATURE:
<223> OTHER INFORMATION: NrdJ1 N-term PROTEIN

<400> SEQUENCE: 19

```
Met Ala Ser Trp Ser His Pro Gln Phe Glu Lys Ala Ser Lys Glu Thr
1               5                   10                  15

Phe Thr His Tyr Gln Pro Gln Gly Asn Ser Asp Pro Ala His Thr Ala
            20                  25                  30

Thr Ala Pro Gly Gly Leu Ser Ala Lys Ala Pro Ala Met Thr Pro Leu
        35                  40                  45

Met Leu Asp Thr Ser Ser Arg Lys Leu Val Ala Trp Asp Gly Thr Thr
    50                  55                  60

Asp Gly Ala Ala Val Gly Ile Leu Ala Val Ala Ala Asp Gln Thr Ser
65                  70                  75                  80

Thr Thr Leu Thr Phe Tyr Lys Ser Gly Thr Phe Arg Tyr Glu Asp Val
                85                  90                  95

Leu Trp Pro Glu Ala Ala Ser Asp Glu Thr Lys Lys Arg Thr Ala Phe
            100                 105                 110

Ala Gly Thr Ala Ile Ser Ile Val Gly Ser Gly Thr Asn Pro Cys Cys
        115                 120                 125

Leu Val Gly Ser Ser Glu Ile Ile Thr Arg Asn Tyr Gly Lys Thr Thr
    130                 135                 140

Ile Lys Glu Val Val Glu Ile Phe Asp Asn Asp Lys Asn Ile Gln Val
145                 150                 155                 160

Leu Ala Phe Asn Thr His Thr Asp Asn Ile Glu Trp Ala Pro Ile Lys
                165                 170                 175

Ala Ala Gln Leu Thr Arg Pro Asn Ala Glu Leu Val Glu Leu Glu Ile
            180                 185                 190

Asn Thr Leu His Gly Val Lys Thr Ile Arg Cys Thr Pro Asp His Pro
        195                 200                 205

Val Tyr Thr Lys Asn Arg Asp Tyr Val Arg Ala Asp Glu Leu Thr Asp
    210                 215                 220

Asp Asp Glu Leu Val Val Ala Ile Gly Gly His His His His His
225                 230                 235                 240
```

<210> SEQ ID NO 20
<211> LENGTH: 105
<212> TYPE: PRT
<213> ORGANISM: Artificial Sequence
<220> FEATURE:
<223> OTHER INFORMATION: NrdJ1 (InteinN)

<400> SEQUENCE: 20

Cys Leu Val Gly Ser Ser Glu Ile Ile Thr Arg Asn Tyr Gly Lys Thr
1               5                   10                  15

Thr Ile Lys Glu Val Val Glu Ile Phe Asp Asn Asp Lys Asn Ile Gln
            20                  25                  30

Val Leu Ala Phe Asn Thr His Thr Asp Asn Ile Glu Trp Ala Pro Ile
        35                  40                  45

Lys Ala Ala Gln Leu Thr Arg Pro Asn Ala Glu Leu Val Glu Leu Glu
    50                  55                  60

Ile Asn Thr Leu His Gly Val Lys Thr Ile Arg Cys Thr Pro Asp His
65                  70                  75                  80

Pro Val Tyr Thr Lys Asn Arg Asp Tyr Val Arg Ala Asp Glu Leu Thr
                85                  90                  95

Asp Asp Asp Glu Leu Val Val Ala Ile
            100                 105

<210> SEQ ID NO 21
<211> LENGTH: 5
<212> TYPE: PRT
<213> ORGANISM: Artificial Sequence
<220> FEATURE:
<223> OTHER INFORMATION: NrdJ1 (ExteinN)

<400> SEQUENCE: 21

Gly Thr Asn Pro Cys
1               5

<210> SEQ ID NO 22
<211> LENGTH: 514
<212> TYPE: DNA
<213> ORGANISM: Artificial Sequence
<220> FEATURE:
<223> OTHER INFORMATION: NrdJ1 C-term DNA

<400> SEQUENCE: 22
catatggaag cgaagaccta catcggtaaa ctgaagagcc gcaagattgt tagcaacgag      60
gacacctacg atatccagac cagcacgcat aatttctttg cgaacgacat cctggtgcac     120
aacagcgaaa ttgtgctggg taccggatct gataaaatta ttcatctgac tgatgattct     180
tttgatactg atgtacttaa ggcagatggt gcaatcctgg ttgatttctg ggcacactgg     240
tgcggtccgt gcaaaatgat cgctccgatt ctggatgaaa tcgctgacga atatcagggc     300
aaactgaccg ttgcaaaact gaacatcgat cacaacccgg gcactgcgcc gaaatatggc     360
atccgtggta tcccgactct gctgctgttc aaaaacggtg aagtggcggc aaccaaagtg     420
ggtgcactgt ctaaaggtca gttgaaagag ttcctcgacg ctaacctggc cggctctgaa     480
ttcagatctc atcaccatca ccatcactaa gctt                                 514

<210> SEQ ID NO 23
<211> LENGTH: 168
<212> TYPE: PRT
<213> ORGANISM: Artificial Sequence
<220> FEATURE:
<223> OTHER INFORMATION: NrdJ1 C-term PROTEIN

<400> SEQUENCE: 23

```
Met Glu Ala Lys Thr Tyr Ile Gly Lys Leu Lys Ser Arg Lys Ile Val
1               5                   10                  15

Ser Asn Glu Asp Thr Tyr Asp Ile Gln Thr Ser Thr His Asn Phe Phe
            20                  25                  30

Ala Asn Asp Ile Leu Val His Asn Ser Glu Ile Val Leu Gly Thr Gly
        35                  40                  45

Ser Asp Lys Ile Ile His Leu Thr Asp Asp Ser Phe Asp Thr Asp Val
    50                  55                  60

Leu Lys Ala Asp Gly Ala Ile Leu Val Asp Phe Trp Ala His Trp Cys
65                  70                  75                  80

Gly Pro Cys Lys Met Ile Ala Pro Ile Leu Asp Glu Ile Ala Asp Glu
                85                  90                  95

Tyr Gln Gly Lys Leu Thr Val Ala Lys Leu Asn Ile Asp His Asn Pro
            100                 105                 110

Gly Thr Ala Pro Lys Tyr Gly Ile Arg Gly Ile Pro Thr Leu Leu Leu
        115                 120                 125

Phe Lys Asn Gly Glu Val Ala Ala Thr Lys Val Gly Ala Leu Ser Lys
    130                 135                 140

Gly Gln Leu Lys Glu Phe Leu Asp Ala Asn Leu Ala Gly Ser Glu Phe
145                 150                 155                 160

Arg Ser His His His His His His
                165
```

<210> SEQ ID NO 24
<211> LENGTH: 40
<212> TYPE: PRT
<213> ORGANISM: Artificial Sequence
<220> FEATURE:
<223> OTHER INFORMATION: NrdJ1 (Inteinc)

<400> SEQUENCE: 24

```
Met Glu Ala Lys Thr Tyr Ile Gly Lys Leu Lys Ser Arg Lys Ile Val
1               5                   10                  15

Ser Asn Glu Asp Thr Tyr Asp Ile Gln Thr Ser Thr His Asn Phe Phe
            20                  25                  30

Ala Asn Asp Ile Leu Val His Asn
        35                  40
```

<210> SEQ ID NO 25
<211> LENGTH: 5
<212> TYPE: PRT
<213> ORGANISM: Artificial Sequence
<220> FEATURE:
<223> OTHER INFORMATION: NrdJ1 (Exteinc)

<400> SEQUENCE: 25

```
Ser Glu Ile Val Leu
1               5
```

<210> SEQ ID NO 26
<211> LENGTH: 681
<212> TYPE: DNA
<213> ORGANISM: Artificial Sequence
<220> FEATURE:
<223> OTHER INFORMATION: DNA-E N-term DNA

<400> SEQUENCE: 26

```
ccatggccag ttggagccac ccgcagttcg aaaaagcgag caaagaaacc tttacccatt    60
```

```
accagccgca gggcaacagt gacccggctc ataccgcaac cgcgcccggc ggattgagtg    120
cgaaagcgcc tgcaatgacc ccgctgatgc tggacacctc cagccgtaag ctggttgcgt    180
gggatggcac caccgacggt gctgccgttg gcattcttgc ggttgctgct gaccagacca    240
gcaccacgct gacgttctac aagtccggca cgttccgtta tgaggatgtg ctctggccgg    300
aggctgccag cgacgagacg aaaaaacgga ccgcgtttgc cggaacggca atcagcatcg    360
ttggatcctg tttaagctat gaaacggaaa tattgacagt agaatatgga ttattaccga    420
ttggtaaaat tgtagaaaag cgcatcgaat gtactgttta tagcgttgat aataatggaa    480
atatttatac acaacctgta gcacaatggc acgatcgcgg agaacaagag gtgtttgagt    540
attgtttgga agatggttca ttgattcggg caacaaaaga ccataagttt atgactgttg    600
atggtcaaat gttgccaatt gatgaaatat ttgaacgtga attggatttg atgcgggttg    660
ataatttgcc gaattaagct t                                             681
```

<210> SEQ ID NO 27
<211> LENGTH: 224
<212> TYPE: PRT
<213> ORGANISM: Artificial Sequence
<220> FEATURE:
<223> OTHER INFORMATION: DNA-E N-term PROTEIN

<400> SEQUENCE: 27

```
Met Ala Ser Trp Ser His Pro Gln Phe Glu Lys Ala Ser Lys Glu Thr
1               5                   10                  15

Phe Thr His Tyr Gln Pro Gln Gly Asn Ser Asp Pro Ala His Thr Ala
            20                  25                  30

Thr Ala Pro Gly Gly Leu Ser Ala Lys Ala Pro Ala Met Thr Pro Leu
        35                  40                  45

Met Leu Asp Thr Ser Ser Arg Lys Leu Val Ala Trp Asp Gly Thr Thr
    50                  55                  60

Asp Gly Ala Ala Val Gly Ile Leu Ala Val Ala Ala Asp Gln Thr Ser
65                  70                  75                  80

Thr Thr Leu Thr Phe Tyr Lys Ser Gly Thr Phe Arg Tyr Glu Asp Val
                85                  90                  95

Leu Trp Pro Glu Ala Ala Ser Asp Glu Thr Lys Lys Arg Thr Ala Phe
            100                 105                 110

Ala Gly Thr Ala Ile Ser Ile Val Gly Ser Cys Leu Ser Tyr Glu Thr
        115                 120                 125

Glu Ile Leu Thr Val Glu Tyr Gly Leu Leu Pro Ile Gly Lys Ile Val
    130                 135                 140

Glu Lys Arg Ile Glu Cys Thr Val Tyr Ser Val Asp Asn Asn Gly Asn
145                 150                 155                 160

Ile Tyr Thr Gln Pro Val Ala Gln Trp His Asp Arg Gly Glu Gln Glu
                165                 170                 175

Val Phe Glu Tyr Cys Leu Glu Asp Gly Ser Leu Ile Arg Ala Thr Lys
            180                 185                 190

Asp His Lys Phe Met Thr Val Asp Gly Gln Met Leu Pro Ile Asp Glu
        195                 200                 205

Ile Phe Glu Arg Glu Leu Asp Leu Met Arg Val Asp Asn Leu Pro Asn
    210                 215                 220
```

<210> SEQ ID NO 28
<211> LENGTH: 102
<212> TYPE: PRT

<213> ORGANISM: Artificial Sequence
<220> FEATURE:
<223> OTHER INFORMATION: DNA-E (Inteinn)

<400> SEQUENCE: 28

```
Cys Leu Ser Tyr Glu Thr Glu Ile Leu Thr Val Glu Tyr Gly Leu Leu
1               5                   10                  15
Pro Ile Gly Lys Ile Val Glu Lys Arg Ile Glu Cys Thr Val Tyr Ser
            20                  25                  30
Val Asp Asn Asn Gly Asn Ile Tyr Thr Gln Pro Val Ala Gln Trp His
        35                  40                  45
Asp Arg Gly Glu Gln Glu Val Phe Glu Tyr Cys Leu Glu Asp Gly Ser
    50                  55                  60
Leu Ile Arg Ala Thr Lys Asp His Lys Phe Met Thr Val Asp Gly Gln
65                  70                  75                  80
Met Leu Pro Ile Asp Glu Ile Phe Glu Arg Glu Leu Asp Leu Met Arg
                85                  90                  95
Val Asp Asn Leu Pro Asn
            100
```

<210> SEQ ID NO 29
<211> LENGTH: 496
<212> TYPE: DNA
<213> ORGANISM: Artificial Sequence
<220> FEATURE:
<223> OTHER INFORMATION: DNA-E C-term DNA

<400> SEQUENCE: 29

```
catatgatca aaatagccac acgtaaatat ttaggcaaac aaaatgtcta tgacattgga    60
gttgagcgcg accataattt tgcactcaaa aatggcttca tagcttctaa ttgtttcaat   120
ggtaccggat ctgataaaat tattcatctg actgatgatt cttttgatac tgatgtactt   180
aaggcagatg gtgcaatcct ggttgatttc tgggcacact ggtgcggtcc gtgcaaaatg   240
atcgctccga ttctggatga aatcgctgac gaatatcagg caaactgac  cgttgcaaaa   300
ctgaacatcg atcacaaccc gggcactgcg ccgaaatatg gcatccgtgg tatcccgact   360
ctgctgctgt tcaaaaacgg tgaagtggcg gcaaccaaag tgggtgcact gtctaaaggt   420
cagttgaaag agttcctcga cgctaacctg gccggctctg aattcagatc tcatcaccat   480
caccatcact aagctt                                                   496
```

<210> SEQ ID NO 30
<211> LENGTH: 162
<212> TYPE: PRT
<213> ORGANISM: Artificial Sequence
<220> FEATURE:
<223> OTHER INFORMATION: DNA-E C-term PROTEIN

<400> SEQUENCE: 30

```
Met Ile Lys Ile Ala Thr Arg Lys Tyr Leu Gly Lys Gln Asn Val Tyr
1               5                   10                  15
Asp Ile Gly Val Glu Arg Asp His Asn Phe Ala Leu Lys Asn Gly Phe
            20                  25                  30
Ile Ala Ser Asn Cys Phe Asn Gly Thr Gly Ser Asp Lys Ile Ile His
        35                  40                  45
Leu Thr Asp Asp Ser Phe Asp Thr Asp Val Leu Lys Ala Asp Gly Ala
    50                  55                  60
Ile Leu Val Asp Phe Trp Ala His Trp Cys Gly Pro Cys Lys Met Ile
65                  70                  75                  80
```

```
Ala Pro Ile Leu Asp Glu Ile Ala Asp Glu Tyr Gln Gly Lys Leu Thr
                85                  90                  95

Val Ala Lys Leu Asn Ile Asp His Asn Pro Gly Thr Ala Pro Lys Tyr
            100                 105                 110

Gly Ile Arg Gly Ile Pro Thr Leu Leu Leu Phe Lys Asn Gly Glu Val
        115                 120                 125

Ala Ala Thr Lys Val Gly Ala Leu Ser Lys Gly Gln Leu Lys Glu Phe
    130                 135                 140

Leu Asp Ala Asn Leu Ala Gly Ser Glu Phe Arg Ser His His His His
145                 150                 155                 160

His His
```

<210> SEQ ID NO 31
<211> LENGTH: 36
<212> TYPE: PRT
<213> ORGANISM: Artificial Sequence
<220> FEATURE:
<223> OTHER INFORMATION: DNA-E (InteinC)

<400> SEQUENCE: 31

```
Met Ile Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn
        35
```

<210> SEQ ID NO 32
<211> LENGTH: 717
<212> TYPE: DNA
<213> ORGANISM: Artificial Sequence
<220> FEATURE:
<223> OTHER INFORMATION: IMPDH N-term DNA

<400> SEQUENCE: 32

```
ccatggccag ttggagccac ccgcagttcg aaaaagcgag caaagaaacc tttacccatt      60
accagccgca gggcaacagt gacccggctc ataccgcaac cgcgcccggc ggattgagtg     120
cgaaagcgcc tgcaatgacc ccgctgatgc tggacacctc cagccgtaag ctggttgcgt     180
gggatggcac caccgacggt gctgccgttg cattcttgc ggttgctgct gaccagacca     240
gcaccacgct gacgttctac aagtccggca cgttccgtta tgaggatgtg ctctggccgg     300
aggctgccag cgacgagacg aaaaaacgga ccgcgtttgc cggaacggca atcagcatcg     360
ttggatccgg cattggcggt ggctgctttg tgccgggcac cctggtgaac acggaaaacg     420
gcctgaagaa aatcgaggaa attaaggtgg cgacaaggt gttcagccat accggcaaac     480
tgcaggaagt tgtggacacg ctgatctttg accgcgacga agaaatcatc agcattaacg     540
gcatcgactg cacgaaaaac cacgagttct acgtgatcga caaggagaac gcgaaccgtg     600
tgaacgaaga caatatccat ctgttcgcgc gttgggttca cgcggaggag ctggacatga     660
aaaaacatct gctgattgag ctggaaggcg ccatcatca ccaccaccac taagctt       717
```

<210> SEQ ID NO 33
<211> LENGTH: 236
<212> TYPE: PRT
<213> ORGANISM: Artificial Sequence
<220> FEATURE:
<223> OTHER INFORMATION: IMPDH N-term PROTEIN

<400> SEQUENCE: 33

```
Met Ala Ser Trp Ser His Pro Gln Phe Glu Lys Ala Ser Lys Glu Thr
1               5                   10                  15
Phe Thr His Tyr Gln Pro Gln Gly Asn Ser Asp Pro Ala His Thr Ala
                20                  25                  30
Thr Ala Pro Gly Gly Leu Ser Ala Lys Ala Pro Ala Met Thr Pro Leu
            35                  40                  45
Met Leu Asp Thr Ser Ser Arg Lys Leu Val Ala Trp Asp Gly Thr Thr
    50                  55                  60
Asp Gly Ala Ala Val Gly Ile Leu Ala Val Ala Asp Gln Thr Ser
65                  70                  75                  80
Thr Thr Leu Thr Phe Tyr Lys Ser Gly Thr Phe Arg Tyr Glu Asp Val
                85                  90                  95
Leu Trp Pro Glu Ala Ala Ser Asp Glu Thr Lys Lys Arg Thr Ala Phe
            100                 105                 110
Ala Gly Thr Ala Ile Ser Ile Val Gly Ser Gly Ile Gly Gly Cys
                115                 120                 125
Phe Val Pro Gly Thr Leu Val Asn Thr Glu Asn Gly Leu Lys Lys Ile
            130                 135                 140
Glu Glu Ile Lys Val Gly Asp Lys Val Phe Ser His Thr Gly Lys Leu
145                 150                 155                 160
Gln Glu Val Val Asp Thr Leu Ile Phe Asp Arg Asp Glu Glu Ile Ile
                165                 170                 175
Ser Ile Asn Gly Ile Asp Cys Thr Lys Asn His Glu Phe Tyr Val Ile
                180                 185                 190
Asp Lys Glu Asn Ala Asn Arg Val Asn Glu Asp Asn Ile His Leu Phe
            195                 200                 205
Ala Arg Trp Val His Ala Glu Glu Leu Asp Met Lys Lys His Leu Leu
        210                 215                 220
Ile Glu Leu Glu Gly Gly His His His His His
225                 230                 235
```

<210> SEQ ID NO 34
<211> LENGTH: 101
<212> TYPE: PRT
<213> ORGANISM: Artificial Sequence
<220> FEATURE:
<223> OTHER INFORMATION: IMPDH (Inteinn)

<400> SEQUENCE: 34

```
Cys Phe Val Pro Gly Thr Leu Val Asn Thr Glu Asn Gly Leu Lys Lys
1               5                   10                  15
Ile Glu Glu Ile Lys Val Gly Asp Lys Val Phe Ser His Thr Gly Lys
                20                  25                  30
Leu Gln Glu Val Val Asp Thr Leu Ile Phe Asp Arg Asp Glu Glu Ile
            35                  40                  45
Ile Ser Ile Asn Gly Ile Asp Cys Thr Lys Asn His Glu Phe Tyr Val
    50                  55                  60
Ile Asp Lys Glu Asn Ala Asn Arg Val Asn Glu Asp Asn Ile His Leu
65                  70                  75                  80
Phe Ala Arg Trp Val His Ala Glu Glu Leu Asp Met Lys Lys His Leu
                85                  90                  95
Leu Ile Glu Leu Glu
            100
```

```
<210> SEQ ID NO 35
<211> LENGTH: 5
<212> TYPE: PRT
<213> ORGANISM: Artificial Sequence
<220> FEATURE:
<223> OTHER INFORMATION: IMPDH (Exteinn)

<400> SEQUENCE: 35

Gly Ile Gly Gly Gly
1               5

<210> SEQ ID NO 36
<211> LENGTH: 514
<212> TYPE: DNA
<213> ORGANISM: Artificial Sequence
<220> FEATURE:
<223> OTHER INFORMATION: IMPDH C-term DNA

<400> SEQUENCE: 36
catatgaagt tcaagctgaa ggagatcacg agcatcgaga ccaagcacta caagggcaag      60
gtgcacgatc tgaccgtgaa tcaggaccac agctataacg tgcgcggcac cgtggtgcat     120
aatagcattt gcagcaccgg taccggatct gataaaatta ttcatctgac tgatgattct     180
tttgatactg atgtacttaa ggcagatggt gcaatcctgg ttgatttctg ggcacactgg     240
tgcggtccgt gcaaaatgat cgctccgatt ctggatgaaa tcgctgacga atatcagggc     300
aaactgaccg ttgcaaaact gaacatcgat cacaacccgg gcactgcgcc gaaatatggc     360
atccgtggta tcccgactct gctgctgttc aaaaacggtg aagtggcggc aaccaaagtg     420
ggtgcactgt ctaaaggtca gttgaaagag ttcctgacg ctaacctggc cggctctgaa      480
ttcagatctc atcaccatca ccatcactaa gctt                                 514

<210> SEQ ID NO 37
<211> LENGTH: 168
<212> TYPE: PRT
<213> ORGANISM: Artificial Sequence
<220> FEATURE:
<223> OTHER INFORMATION: IMPDH C-term PROTEIN

<400> SEQUENCE: 37

Met Lys Phe Lys Leu Lys Glu Ile Thr Ser Ile Glu Thr Lys His Tyr
1               5                   10                  15

Lys Gly Lys Val His Asp Leu Thr Val Asn Gln Asp His Ser Tyr Asn
            20                  25                  30

Val Arg Gly Thr Val Val His Asn Ser Ile Cys Ser Thr Gly Thr Gly
        35                  40                  45

Ser Asp Lys Ile Ile His Leu Thr Asp Asp Ser Phe Asp Thr Asp Val
    50                  55                  60

Leu Lys Ala Asp Gly Ala Ile Leu Val Asp Phe Trp Ala His Trp Cys
65                  70                  75                  80

Gly Pro Cys Lys Met Ile Ala Pro Ile Leu Asp Glu Ile Ala Asp Glu
                85                  90                  95

Tyr Gln Gly Lys Leu Thr Val Ala Lys Leu Asn Ile Asp His Asn Pro
            100                 105                 110

Gly Thr Ala Pro Lys Tyr Gly Ile Arg Gly Ile Pro Thr Leu Leu Leu
        115                 120                 125

Phe Lys Asn Gly Glu Val Ala Ala Thr Lys Val Gly Ala Leu Ser Lys
    130                 135                 140

Gly Gln Leu Lys Glu Phe Leu Asp Ala Asn Leu Ala Gly Ser Glu Phe
145                 150                 155                 160
```

Arg Ser His His His His His His
            165

<210> SEQ ID NO 38
<211> LENGTH: 40
<212> TYPE: PRT
<213> ORGANISM: Artificial Sequence
<220> FEATURE:
<223> OTHER INFORMATION: IMPDH (InteinC)

<400> SEQUENCE: 38

Met Lys Phe Lys Leu Lys Glu Ile Thr Ser Ile Glu Thr Lys His Tyr
1               5                   10                  15

Lys Gly Lys Val His Asp Leu Thr Val Asn Gln Asp His Ser Tyr Asn
            20                  25                  30

Val Arg Gly Thr Val Val His Asn
        35                  40

<210> SEQ ID NO 39
<211> LENGTH: 5
<212> TYPE: PRT
<213> ORGANISM: Artificial Sequence
<220> FEATURE:
<223> OTHER INFORMATION: IMPDH (ExteinC)

<400> SEQUENCE: 39

Ser Ile Cys Ser Thr
1               5

<210> SEQ ID NO 40
<211> LENGTH: 8
<212> TYPE: PRT
<213> ORGANISM: Artificial Sequence
<220> FEATURE:
<223> OTHER INFORMATION: Strep taq

<400> SEQUENCE: 40

Trp Ser His Pro Gln Phe Glu Lys
1               5

<210> SEQ ID NO 41
<211> LENGTH: 107
<212> TYPE: PRT
<213> ORGANISM: Artificial Sequence
<220> FEATURE:
<223> OTHER INFORMATION: gpD

<400> SEQUENCE: 41

Lys Glu Thr Phe Thr His Tyr Gln Pro Gln Gly Asn Ser Asp Pro Ala
1               5                   10                  15

His Thr Ala Thr Ala Pro Gly Gly Leu Ser Ala Lys Ala Pro Ala Met
            20                  25                  30

Thr Pro Leu Met Leu Asp Thr Ser Ser Arg Lys Leu Val Ala Trp Asp
        35                  40                  45

Gly Thr Thr Asp Gly Ala Ala Val Gly Ile Leu Ala Val Ala Ala Asp
    50                  55                  60

Gln Thr Ser Thr Thr Leu Thr Phe Tyr Lys Ser Gly Thr Phe Arg Tyr
65                  70                  75                  80

Glu Asp Val Leu Trp Pro Glu Ala Ala Ser Asp Glu Thr Lys Lys Arg
                85                  90                  95

Thr Ala Phe Ala Gly Thr Ala Ile Ser Ile Val
            100                 105

```
<210> SEQ ID NO 42
<211> LENGTH: 6
<212> TYPE: PRT
<213> ORGANISM: Artificial Sequence
<220> FEATURE:
<223> OTHER INFORMATION: H6

<400> SEQUENCE: 42

His His His His His His
1               5

<210> SEQ ID NO 43
<211> LENGTH: 111
<212> TYPE: PRT
<213> ORGANISM: Artificial Sequence
<220> FEATURE:
<223> OTHER INFORMATION: Trx

<400> SEQUENCE: 43

Gly Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala His Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp His Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser
            100                 105                 110

<210> SEQ ID NO 44
<211> LENGTH: 13
<212> TYPE: PRT
<213> ORGANISM: Artificial Sequence
<220> FEATURE:
<223> OTHER INFORMATION: Sequence ChsXcplhXTXXG comprised in the N1 box
<220> FEATURE:
<221> NAME/KEY: VARIANT
<222> LOCATION: (2)..(2)
<223> OTHER INFORMATION: Xaa is a hydrophobic amino acid
<220> FEATURE:
<221> NAME/KEY: VARIANT
<222> LOCATION: (3)..(3)
<223> OTHER INFORMATION: Xaa is a small amino acid
<220> FEATURE:
<221> NAME/KEY: VARIANT
<222> LOCATION: (4)..(4)
<223> OTHER INFORMATION: Xaa is any amino acid
<220> FEATURE:
<221> NAME/KEY: VARIANT
<222> LOCATION: (5)..(5)
<223> OTHER INFORMATION: Xaa is a charged amino acid
<220> FEATURE:
<221> NAME/KEY: VARIANT
<222> LOCATION: (6)..(6)
<223> OTHER INFORMATION: Xaa is a polar amino acid
<220> FEATURE:
<221> NAME/KEY: VARIANT
<222> LOCATION: (7)..(7)
<223> OTHER INFORMATION: Xaa is a large amino acid
<220> FEATURE:
<221> NAME/KEY: VARIANT
<222> LOCATION: (8)..(8)
```

-continued

```
<223> OTHER INFORMATION: Xaa is a hydrophobic amino acid
<220> FEATURE:
<221> NAME/KEY: VARIANT
<222> LOCATION: (9)..(9)
<223> OTHER INFORMATION: Xaa is any amino acid
<220> FEATURE:
<221> NAME/KEY: VARIANT
<222> LOCATION: (11)..(12)
<223> OTHER INFORMATION: Xaa is any amino acid

<400> SEQUENCE: 44

Cys Xaa Xaa Xaa Xaa Xaa Xaa Xaa Xaa Thr Xaa Xaa Gly
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Sequence comprised in the intein N-terminal
      domain
<220> FEATURE:
<221> NAME/KEY: VARIANT
<222> LOCATION: (1)..(1)
<223> OTHER INFORMATION: Xaa = Cys
<220> FEATURE:
<221> NAME/KEY: VARIANT
<222> LOCATION: (2)..(2)
<223> OTHER INFORMATION: Xaa = Leu, Phe, or Val
<220> FEATURE:
<221> NAME/KEY: VARIANT
<222> LOCATION: (3)..(3)
<223> OTHER INFORMATION: Xaa = Ser, Thr, Val, or Ala
<220> FEATURE:
<221> NAME/KEY: VARIANT
<222> LOCATION: (4)..(4)
<223> OTHER INFORMATION: Xaa = Leu, Pro, Gly, or Tyr
<220> FEATURE:
<221> NAME/KEY: VARIANT
<222> LOCATION: (5)..(5)
<223> OTHER INFORMATION: Xaa = Asp, Glu, Lys, or Gly
<220> FEATURE:
<221> NAME/KEY: VARIANT
<222> LOCATION: (6)..(6)
<223> OTHER INFORMATION: Xaa = Thr or Ala
<220> FEATURE:
<221> NAME/KEY: VARIANT
<222> LOCATION: (7)..(7)
<223> OTHER INFORMATION: Xaa = Glu, Gln, or Leu
<220> FEATURE:
<221> NAME/KEY: VARIANT
<222> LOCATION: (7)..(7)
<223> OTHER INFORMATION: Xaa = Met, Lys, or Thr
<220> FEATURE:
<221> NAME/KEY: VARIANT
<222> LOCATION: (8)..(8)
<223> OTHER INFORMATION: Xaa = Ile or Val
<220> FEATURE:
<221> NAME/KEY: VARIANT
<222> LOCATION: (9)..(9)
<223> OTHER INFORMATION: Xaa = Leu, Gln, Val or Asn
<220> FEATURE:
<221> NAME/KEY: VARIANT
<222> LOCATION: (9)..(9)
<223> OTHER INFORMATION: Xaa = Lys, Asp, or Thr
<220> FEATURE:
<221> NAME/KEY: VARIANT
<222> LOCATION: (10)..(10)
<223> OTHER INFORMATION: Xaa = Thr, Ile, or Val
<220> FEATURE:
<221> NAME/KEY: VARIANT
<222> LOCATION: (11)..(11)
<223> OTHER INFORMATION: Xaa = Val, Pro, Gln, or Asn
<220> FEATURE:
<221> NAME/KEY: VARIANT
<222> LOCATION: (11)..(11)
<223> OTHER INFORMATION: Xaa = Glu, Lys, or Leu
```

```
<220> FEATURE:
<221> NAME/KEY: VARIANT
<222> LOCATION: (12)..(12)
<223> OTHER INFORMATION: Xaa = Glu, Gln, Gly, or Asn
<220> FEATURE:
<221> NAME/KEY: VARIANT
<222> LOCATION: (12)..(12)
<223> OTHER INFORMATION: Xaa = Tyr, Ile, or Glu
<220> FEATURE:
<221> NAME/KEY: VARIANT
<222> LOCATION: (13)..(13)
<223> OTHER INFORMATION: Xaa = Tyr, Gly, Lys, or Pro
<220> FEATURE:
<221> NAME/KEY: VARIANT
<222> LOCATION: (13)..(13)
<223> OTHER INFORMATION: Xaa = Asp

<400> SEQUENCE: 45

Xaa Xaa Xaa Xaa Xaa Xaa Xaa Xaa Xaa Xaa Xaa Xaa Xaa
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Sequence comprised in the intein N-terminal
      domain
<220> FEATURE:
<221> NAME/KEY: VARIANT
<222> LOCATION: (1)..(1)
<223> OTHER INFORMATION: Xaa = Cys
<220> FEATURE:
<221> NAME/KEY: VARIANT
<222> LOCATION: (2)..(2)
<223> OTHER INFORMATION: Xaa = Leu, Phe, or Val
<220> FEATURE:
<221> NAME/KEY: VARIANT
<222> LOCATION: (3)..(3)
<223> OTHER INFORMATION: Xaa = Ser, Thr, Val, or Ala
<220> FEATURE:
<221> NAME/KEY: VARIANT
<222> LOCATION: (4)..(4)
<223> OTHER INFORMATION: Xaa = Leu, Pro, or Gly
<220> FEATURE:
<221> NAME/KEY: VARIANT
<222> LOCATION: (5)..(5)
<223> OTHER INFORMATION: Xaa = Asp, Lys, or Gly
<220> FEATURE:
<221> NAME/KEY: VARIANT
<222> LOCATION: (6)..(6)
<223> OTHER INFORMATION: Xaa = Thr or Ala
<220> FEATURE:
<221> NAME/KEY: VARIANT
<222> LOCATION: (7)..(7)
<223> OTHER INFORMATION: Xaa = Gln, Leu, Met, or Lys
<220> FEATURE:
<221> NAME/KEY: VARIANT
<222> LOCATION: (7)..(7)
<223> OTHER INFORMATION: Xaa = Thr
<220> FEATURE:
<221> NAME/KEY: VARIANT
<222> LOCATION: (8)..(8)
<223> OTHER INFORMATION: Xaa = Ile or Val
<220> FEATURE:
<221> NAME/KEY: VARIANT
<222> LOCATION: (9)..(9)
<223> OTHER INFORMATION: Xaa = Gln, Val, Asn, or Lys
<220> FEATURE:
<221> NAME/KEY: VARIANT
<222> LOCATION: (9)..(9)
<223> OTHER INFORMATION: Xaa = Asp or Thr
<220> FEATURE:
<221> NAME/KEY: VARIANT
<222> LOCATION: (10)..(10)
<223> OTHER INFORMATION: Xaa = Thr, Ile, or Val
<220> FEATURE:
```

```
<221> NAME/KEY: VARIANT
<222> LOCATION: (11)..(11)
<223> OTHER INFORMATION: Xaa = Pro, Gln, Asn, or Glu
<220> FEATURE:
<221> NAME/KEY: VARIANT
<222> LOCATION: (11)..(11)
<223> OTHER INFORMATION: Xaa = Lys or Leu
<220> FEATURE:
<221> NAME/KEY: VARIANT
<222> LOCATION: (12)..(12)
<223> OTHER INFORMATION: Xaa = Glu, Gln, Gly, or Asn
<220> FEATURE:
<221> NAME/KEY: VARIANT
<222> LOCATION: (12)..(12)
<223> OTHER INFORMATION: Xaa = Tyr, Ile, or Glu
<220> FEATURE:
<221> NAME/KEY: VARIANT
<222> LOCATION: (13)..(13)
<223> OTHER INFORMATION: Xaa = Gly, Lys, Pro, or Asp

<400> SEQUENCE: 46

Xaa Xaa Xaa Xaa Xaa Xaa Xaa Xaa Xaa Xaa Xaa Xaa Xaa
1               5                   10

<210> SEQ ID NO 47
<211> LENGTH: 15
<212> TYPE: PRT
<213> ORGANISM: Artificial Sequence
<220> FEATURE:
<223> OTHER INFORMATION: Sequence GXXhXhTXaHXhhTX  comprised in the N3
      box
<220> FEATURE:
<221> NAME/KEY: VARIANT
<222> LOCATION: (2)..(3)
<223> OTHER INFORMATION: Xaa is any amino acid
<220> FEATURE:
<221> NAME/KEY: VARIANT
<222> LOCATION: (4)..(4)
<223> OTHER INFORMATION: Xaa is a hydrophobic amino acid
<220> FEATURE:
<221> NAME/KEY: VARIANT
<222> LOCATION: (5)..(5)
<223> OTHER INFORMATION: Xaa is any amino acid
<220> FEATURE:
<221> NAME/KEY: VARIANT
<222> LOCATION: (6)..(6)
<223> OTHER INFORMATION: Xaa is a hydrophobic amino acid
<220> FEATURE:
<221> NAME/KEY: VARIANT
<222> LOCATION: (8)..(8)
<223> OTHER INFORMATION: Xaa is any amino acid
<220> FEATURE:
<221> NAME/KEY: VARIANT
<222> LOCATION: (9)..(9)
<223> OTHER INFORMATION: Xaa is an acidic amino acid
<220> FEATURE:
<221> NAME/KEY: VARIANT
<222> LOCATION: (11)..(11)
<223> OTHER INFORMATION: Xaa is any amino acid
<220> FEATURE:
<221> NAME/KEY: VARIANT
<222> LOCATION: (12)..(13)
<223> OTHER INFORMATION: Xaa is a hydrophobic amino acid
<220> FEATURE:
<221> NAME/KEY: VARIANT
<222> LOCATION: (15)..(15)
<223> OTHER INFORMATION: Xaa is any amino acid

<400> SEQUENCE: 47

Gly Xaa Xaa Xaa Xaa Xaa Thr Xaa Xaa His Xaa Xaa Xaa Thr Xaa
1               5                   10                  15

<210> SEQ ID NO 48
<211> LENGTH: 15
<212> TYPE: PRT
```

```
<213> ORGANISM: Artificial Sequence
<220> FEATURE:
<223> OTHER INFORMATION: Sequence comprised in the intein N-terminal
      domain
<220> FEATURE:
<221> NAME/KEY: VARIANT
<222> LOCATION: (1)..(1)
<223> OTHER INFORMATION: Xaa = Gly or Ala
<220> FEATURE:
<221> NAME/KEY: VARIANT
<222> LOCATION: (2)..(2)
<223> OTHER INFORMATION: Xaa = Ser, Lys, Gln, or Asn
<220> FEATURE:
<221> NAME/KEY: VARIANT
<222> LOCATION: (2)..(2)
<223> OTHER INFORMATION: Xaa = Phe
<220> FEATURE:
<221> NAME/KEY: VARIANT
<222> LOCATION: (3)..(3)
<223> OTHER INFORMATION: Xaa = Leu, Glu, Lys, or Arg
<220> FEATURE:
<221> NAME/KEY: VARIANT
<222> LOCATION: (4)..(4)
<223> OTHER INFORMATION: Xaa = Ile, Leu, or Val
<220> FEATURE:
<221> NAME/KEY: VARIANT
<222> LOCATION: (5)..(5)
<223> OTHER INFORMATION: Xaa = Arg, Ile, Val, or Asn
<220> FEATURE:
<221> NAME/KEY: VARIANT
<222> LOCATION: (6)..(6)
<223> OTHER INFORMATION: Xaa = Ala, Cys, Val, or Glu
<220> FEATURE:
<221> NAME/KEY: VARIANT
<222> LOCATION: (7)..(7)
<223> OTHER INFORMATION: Xaa = Thr, Ser, or Asp
<220> FEATURE:
<221> NAME/KEY: VARIANT
<222> LOCATION: (8)..(8)
<223> OTHER INFORMATION: Xaa = Lys, Glu, Ala, or Pro
<220> FEATURE:
<221> NAME/KEY: VARIANT
<222> LOCATION: (8)..(8)
<223> OTHER INFORMATION: Xaa = Asn
<220> FEATURE:
<221> NAME/KEY: VARIANT
<222> LOCATION: (9)..(9)
<223> OTHER INFORMATION: Xaa = Asp, Glu, Asn, or Ile
<220> FEATURE:
<221> NAME/KEY: VARIANT
<222> LOCATION: (10)..(10)
<223> OTHER INFORMATION: Xaa = His
<220> FEATURE:
<221> NAME/KEY: VARIANT
<222> LOCATION: (11)..(11)
<223> OTHER INFORMATION: Xaa = Lys, Leu, Gln, or Met
<220> FEATURE:
<221> NAME/KEY: VARIANT
<222> LOCATION: (12)..(12)
<223> OTHER INFORMATION: Xaa = Phe, Val, or Ile
<220> FEATURE:
<221> NAME/KEY: VARIANT
<222> LOCATION: (13)..(13)
<223> OTHER INFORMATION: Xaa = Met, Pro, Phe, or Tyr
<220> FEATURE:
<221> NAME/KEY: VARIANT
<222> LOCATION: (13)..(13)
<223> OTHER INFORMATION: Xaa = Ala
<220> FEATURE:
<221> NAME/KEY: VARIANT
<222> LOCATION: (14)..(14)
<223> OTHER INFORMATION: Xaa = Thr
<220> FEATURE:
<221> NAME/KEY: VARIANT
<222> LOCATION: (15)..(15)
<223> OTHER INFORMATION: Xaa = Val, Gln, Lys, or Leu

<400> SEQUENCE: 48
```

Xaa Xaa Xaa Xaa Xaa Xaa Xaa Xaa Xaa Xaa Xaa Xaa Xaa Xaa Xaa
1               5                   10                  15

<210> SEQ ID NO 49
<211> LENGTH: 15
<212> TYPE: PRT
<213> ORGANISM: Artificial Sequence
<220> FEATURE:
<223> OTHER INFORMATION: Sequence comprised in the intein N-terminal
      domain
<220> FEATURE:
<221> NAME/KEY: VARIANT
<222> LOCATION: (1)..(1)
<223> OTHER INFORMATION: Xaa = Gly or Ala
<220> FEATURE:
<221> NAME/KEY: VARIANT
<222> LOCATION: (2)..(2)
<223> OTHER INFORMATION: Xaa = Lys, Gln, Asn, or Phe
<220> FEATURE:
<221> NAME/KEY: VARIANT
<222> LOCATION: (3)..(3)
<223> OTHER INFORMATION: Xaa = Glu, Lys, or Arg
<220> FEATURE:
<221> NAME/KEY: VARIANT
<222> LOCATION: (4)..(4)
<223> OTHER INFORMATION: Xaa = Ile, Leu, or Val
<220> FEATURE:
<221> NAME/KEY: VARIANT
<222> LOCATION: (5)..(5)
<223> OTHER INFORMATION: Xaa = Arg, Ile, Val, or Asn
<220> FEATURE:
<221> NAME/KEY: VARIANT
<222> LOCATION: (6)..(6)
<223> OTHER INFORMATION: Xaa = Cys, Val, or Glu
<220> FEATURE:
<221> NAME/KEY: VARIANT
<222> LOCATION: (7)..(7)
<223> OTHER INFORMATION: Xaa = Thr, Ser, or Asp
<220> FEATURE:
<221> NAME/KEY: VARIANT
<222> LOCATION: (8)..(8)
<223> OTHER INFORMATION: Xaa = Glu, Ala, Pro, or Asn
<220> FEATURE:
<221> NAME/KEY: VARIANT
<222> LOCATION: (9)..(9)
<223> OTHER INFORMATION: Xaa = Asp, Glu, Asn, or Ile
<220> FEATURE:
<221> NAME/KEY: VARIANT
<222> LOCATION: (10)..(10)
<223> OTHER INFORMATION: Xaa = His
<220> FEATURE:
<221> NAME/KEY: VARIANT
<222> LOCATION: (11)..(11)
<223> OTHER INFORMATION: Xaa = Lys, Leu, Gln, or Met
<220> FEATURE:
<221> NAME/KEY: VARIANT
<222> LOCATION: (12)..(12)
<223> OTHER INFORMATION: Xaa = Phe, Val, or Ile
<220> FEATURE:
<221> NAME/KEY: VARIANT
<222> LOCATION: (13)..(13)
<223> OTHER INFORMATION: Xaa = Pro, Phe, Tyr, or Ala
<220> FEATURE:
<221> NAME/KEY: VARIANT
<222> LOCATION: (14)..(14)
<223> OTHER INFORMATION: Xaa = Thr
<220> FEATURE:
<221> NAME/KEY: VARIANT
<222> LOCATION: (15)..(15)
<223> OTHER INFORMATION: Xaa = Gln, Lys, or Leu

<400> SEQUENCE: 49

Xaa Xaa Xaa Xaa Xaa Xaa Xaa Xaa Xaa Xaa Xaa Xaa Xaa Xaa Xaa
1               5                   10                  15

<210> SEQ ID NO 50

```
<211> LENGTH: 14
<212> TYPE: PRT
<213> ORGANISM: Artificial Sequence
<220> FEATURE:
<223> OTHER INFORMATION: Sequence XhhDIpVXXpHXFX comprised in the C1
      box
<220> FEATURE:
<221> NAME/KEY: VARIANT
<222> LOCATION: (1)..(1)
<223> OTHER INFORMATION: Xaa is any amino acid
<220> FEATURE:
<221> NAME/KEY: VARIANT
<222> LOCATION: (2)..(3)
<223> OTHER INFORMATION: Xaa is a hydrophobic amino acid
<220> FEATURE:
<221> NAME/KEY: VARIANT
<222> LOCATION: (6)..(6)
<223> OTHER INFORMATION: Xaa is a polar amino acid
<220> FEATURE:
<221> NAME/KEY: VARIANT
<222> LOCATION: (8)..(9)
<223> OTHER INFORMATION: Xaa is any amino acid
<220> FEATURE:
<221> NAME/KEY: VARIANT
<222> LOCATION: (10)..(10)
<223> OTHER INFORMATION: Xaa is a polar amino acid
<220> FEATURE:
<221> NAME/KEY: VARIANT
<222> LOCATION: (12)..(12)
<223> OTHER INFORMATION: Xaa is any amino acid
<220> FEATURE:
<221> NAME/KEY: VARIANT
<222> LOCATION: (14)..(14)
<223> OTHER INFORMATION: Xaa is any amino acid

<400> SEQUENCE: 50

Xaa Xaa Xaa Asp Ile Xaa Val Xaa Xaa Xaa His Xaa Phe Xaa
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Sequence comprised in the intein C-terminal
      domain
<220> FEATURE:
<221> NAME/KEY: VARIANT
<222> LOCATION: (1)..(1)
<223> OTHER INFORMATION: Xaa = Asn, Glu, Leu, or Lys
<220> FEATURE:
<221> NAME/KEY: VARIANT
<222> LOCATION: (1)..(1)
<223> OTHER INFORMATION: Xaa = Gln, Asp, Pro, or Arg
<220> FEATURE:
<221> NAME/KEY: VARIANT
<222> LOCATION: (2)..(2)
<223> OTHER INFORMATION: Xaa = Val, Leu, or Thr
<220> FEATURE:
<221> NAME/KEY: VARIANT
<222> LOCATION: (3)..(3)
<223> OTHER INFORMATION: Xaa = Tyr, Ile, Val, or His
<220> FEATURE:
<221> NAME/KEY: VARIANT
<222> LOCATION: (3)..(3)
<223> OTHER INFORMATION: Xaa = Phe
<220> FEATURE:
<221> NAME/KEY: VARIANT
<222> LOCATION: (4)..(4)
<223> OTHER INFORMATION: Xaa = Asp
<220> FEATURE:
<221> NAME/KEY: VARIANT
<222> LOCATION: (5)..(5)
<223> OTHER INFORMATION: Xaa = Ile or Leu
<220> FEATURE:
<221> NAME/KEY: VARIANT
<222> LOCATION: (6)..(6)
```

```
<223> OTHER INFORMATION: Xaa = Gly, Glu, Thr, or Gln
<220> FEATURE:
<221> NAME/KEY: VARIANT
<222> LOCATION: (6)..(6)
<223> OTHER INFORMATION: Xaa = Lys
<220> FEATURE:
<221> NAME/KEY: VARIANT
<222> LOCATION: (7)..(7)
<223> OTHER INFORMATION: Xaa = Val or Thr
<220> FEATURE:
<221> NAME/KEY: VARIANT
<222> LOCATION: (8)..(8)
<223> OTHER INFORMATION: Xaa = Glu, Ser, Thr, or Asp
<220> FEATURE:
<221> NAME/KEY: VARIANT
<222> LOCATION: (8)..(8)
<223> OTHER INFORMATION: Xaa = Asn or Lys
<220> FEATURE:
<221> NAME/KEY: VARIANT
<222> LOCATION: (9)..(9)
<223> OTHER INFORMATION: Xaa = Arg, Gly, Asp, or Asn
<220> FEATURE:
<221> NAME/KEY: VARIANT
<222> LOCATION: (9)..(9)
<223> OTHER INFORMATION: Xaa = Gln, Ser, or Lys
<220> FEATURE:
<221> NAME/KEY: VARIANT
<222> LOCATION: (10)..(10)
<223> OTHER INFORMATION: Xaa = Asp, Glu, Asn, or Thr
<220> FEATURE:
<221> NAME/KEY: VARIANT
<222> LOCATION: (10)..(10)
<223> OTHER INFORMATION: Xaa = Lys
<220> FEATURE:
<221> NAME/KEY: VARIANT
<222> LOCATION: (11)..(11)
<223> OTHER INFORMATION: Xaa = His, Arg, Ser, or Ile
<220> FEATURE:
<221> NAME/KEY: VARIANT
<222> LOCATION: (11)..(11)
<223> OTHER INFORMATION: Xaa = Asn
<220> FEATURE:
<221> NAME/KEY: VARIANT
<222> LOCATION: (12)..(12)
<223> OTHER INFORMATION: Xaa = Asn, Leu, Ser, or Ile
<220> FEATURE:
<221> NAME/KEY: VARIANT
<222> LOCATION: (12)..(12)
<223> OTHER INFORMATION: Xaa = Asn
<220> FEATURE:
<221> NAME/KEY: VARIANT
<222> LOCATION: (13)..(13)
<223> OTHER INFORMATION: Xaa = Phe, Tyr, Leu, or Ile
<220> FEATURE:
<221> NAME/KEY: VARIANT
<222> LOCATION: (14)..(14)
<223> OTHER INFORMATION: Xaa = Ala, Tyr, Phe, or Asn
<220> FEATURE:
<221> NAME/KEY: VARIANT
<222> LOCATION: (14)..(14)
<223> OTHER INFORMATION: Xaa = Cys or Ser

<400> SEQUENCE: 51

Xaa Xaa Xaa Xaa Xaa Xaa Xaa Xaa Xaa Xaa Xaa Xaa Xaa Xaa
1               5                   10

<210> SEQ ID NO 52
<211> LENGTH: 14
<212> TYPE: PRT
<213> ORGANISM: Artificial Sequence
<220> FEATURE:
<223> OTHER INFORMATION: Sequence comprised in the intein C-terminal
      domain
<220> FEATURE:
<221> NAME/KEY: VARIANT
<222> LOCATION: (1)..(1)
<223> OTHER INFORMATION: Xaa = Glu, Leu, Lys, or Gln
```

-continued

```
<220> FEATURE:
<221> NAME/KEY: VARIANT
<222> LOCATION: (1)..(1)
<223> OTHER INFORMATION: Xaa = Asp, Pro, or Arg
<220> FEATURE:
<221> NAME/KEY: VARIANT
<222> LOCATION: (2)..(2)
<223> OTHER INFORMATION: Xaa = Val, Leu, or Thr
<220> FEATURE:
<221> NAME/KEY: VARIANT
<222> LOCATION: (3)..(3)
<223> OTHER INFORMATION: Xaa = Tyr, Ile, Val, or His
<220> FEATURE:
<221> NAME/KEY: VARIANT
<222> LOCATION: (3)..(3)
<223> OTHER INFORMATION: Xaa = Phe
<220> FEATURE:
<221> NAME/KEY: VARIANT
<222> LOCATION: (4)..(4)
<223> OTHER INFORMATION: Xaa = Asp
<220> FEATURE:
<221> NAME/KEY: VARIANT
<222> LOCATION: (5)..(5)
<223> OTHER INFORMATION: Xaa = Ile or Leu
<220> FEATURE:
<221> NAME/KEY: VARIANT
<222> LOCATION: (6)..(6)
<223> OTHER INFORMATION: Xaa = Gly, Glu, Thr, or Gln
<220> FEATURE:
<221> NAME/KEY: VARIANT
<222> LOCATION: (6)..(6)
<223> OTHER INFORMATION: Xaa = Lys
<220> FEATURE:
<221> NAME/KEY: VARIANT
<222> LOCATION: (7)..(7)
<223> OTHER INFORMATION: Xaa = Val or Thr
<220> FEATURE:
<221> NAME/KEY: VARIANT
<222> LOCATION: (8)..(8)
<223> OTHER INFORMATION: Xaa = Glu, Ser, Thr, or Asp
<220> FEATURE:
<221> NAME/KEY: VARIANT
<222> LOCATION: (8)..(8)
<223> OTHER INFORMATION: Xaa = Asn or Lys
<220> FEATURE:
<221> NAME/KEY: VARIANT
<222> LOCATION: (9)..(9)
<223> OTHER INFORMATION: Xaa = Gly, Asp, Asn, or Gln
<220> FEATURE:
<221> NAME/KEY: VARIANT
<222> LOCATION: (9)..(9)
<223> OTHER INFORMATION: Xaa = Ser or Lys
<220> FEATURE:
<221> NAME/KEY: VARIANT
<222> LOCATION: (10)..(10)
<223> OTHER INFORMATION: Xaa = Asp, Glu, Asn, or Thr
<220> FEATURE:
<221> NAME/KEY: VARIANT
<222> LOCATION: (10)..(10)
<223> OTHER INFORMATION: Xaa = Lys
<220> FEATURE:
<221> NAME/KEY: VARIANT
<222> LOCATION: (11)..(11)
<223> OTHER INFORMATION: Xaa = His, Arg, Ser or Ile
<220> FEATURE:
<221> NAME/KEY: VARIANT
<222> LOCATION: (11)..(11)
<223> OTHER INFORMATION: Xaa = Asn
<220> FEATURE:
<221> NAME/KEY: VARIANT
<222> LOCATION: (12)..(12)
<223> OTHER INFORMATION: Xaa = Asn, Leu, Ser or Ile
<220> FEATURE:
<221> NAME/KEY: VARIANT
<222> LOCATION: (12)..(12)
<223> OTHER INFORMATION: Xaa = Asn
<220> FEATURE:
<221> NAME/KEY: VARIANT
<222> LOCATION: (13)..(13)
```

```
<223> OTHER INFORMATION: Xaa = Phe, Tyr, Phe, or Asn
<220> FEATURE:
<221> NAME/KEY: VARIANT
<222> LOCATION: (14)..(14)
<223> OTHER INFORMATION: Xaa = Ala, Tyr, Phe, or Asn
<220> FEATURE:
<221> NAME/KEY: VARIANT
<222> LOCATION: (14)..(14)
<223> OTHER INFORMATION: Xaa = Cys or Ser

<400> SEQUENCE: 52

Xaa Xaa Xaa Xaa Xaa Xaa Xaa Xaa Xaa Xaa Xaa Xaa Xaa Xaa
1               5                   10

<210> SEQ ID NO 53
<211> LENGTH: 9
<212> TYPE: PRT
<213> ORGANISM: Artificial Sequence
<220> FEATURE:
<223> OTHER INFORMATION: Sequence hNXIhXHNn comprised in the C2 box
<220> FEATURE:
<221> NAME/KEY: VARIANT
<222> LOCATION: (1)..(1)
<223> OTHER INFORMATION: Xaa is a hydrophobic amino acid
<220> FEATURE:
<221> NAME/KEY: VARIANT
<222> LOCATION: (3)..(3)
<223> OTHER INFORMATION: Xaa is any amino acid
<220> FEATURE:
<221> NAME/KEY: VARIANT
<222> LOCATION: (5)..(5)
<223> OTHER INFORMATION: Xaa is a hydrophobic amino acid
<220> FEATURE:
<221> NAME/KEY: VARIANT
<222> LOCATION: (6)..(6)
<223> OTHER INFORMATION: Xaa is any amino acid
<220> FEATURE:
<221> NAME/KEY: VARIANT
<222> LOCATION: (9)..(9)
<223> OTHER INFORMATION: Xaa is a nucleophilic amino acid

<400> SEQUENCE: 53

Xaa Asn Xaa Ile Xaa Xaa His Asn Xaa
1               5

<210> SEQ ID NO 54
<211> LENGTH: 9
<212> TYPE: PRT
<213> ORGANISM: Artificial Sequence
<220> FEATURE:
<223> OTHER INFORMATION: Sequence comprised in the intein C-terminal
      domain
<220> FEATURE:
<221> NAME/KEY: VARIANT
<222> LOCATION: (1)..(1)
<223> OTHER INFORMATION: Xaa = Leu, Ala, Val, or Ile
<220> FEATURE:
<221> NAME/KEY: VARIANT
<222> LOCATION: (1)..(1)
<223> OTHER INFORMATION: Xaa = Cys
<220> FEATURE:
<221> NAME/KEY: VARIANT
<222> LOCATION: (2)..(2)
<223> OTHER INFORMATION: Xaa = Asn or Arg
<220> FEATURE:
<221> NAME/KEY: VARIANT
<222> LOCATION: (3)..(3)
<223> OTHER INFORMATION: Xaa = Gly, Asp, Ala, or Asn
<220> FEATURE:
<221> NAME/KEY: VARIANT
<222> LOCATION: (4)..(4)
<223> OTHER INFORMATION: Xaa = Ile, Phe, or Thr
<220> FEATURE:
<221> NAME/KEY: VARIANT
<222> LOCATION: (5)..(5)
```

```
<223> OTHER INFORMATION: Xaa = Leu, Ile, or Val
<220> FEATURE:
<221> NAME/KEY: VARIANT
<222> LOCATION: (6)..(6)
<223> OTHER INFORMATION: Xaa = Val, Ile, Thr, or Ala
<220> FEATURE:
<221> NAME/KEY: VARIANT
<222> LOCATION: (7)..(7)
<223> OTHER INFORMATION: Xaa = His or Ser
<220> FEATURE:
<221> NAME/KEY: VARIANT
<222> LOCATION: (8)..(8)
<223> OTHER INFORMATION: Xaa = Asn
<220> FEATURE:
<221> NAME/KEY: VARIANT
<222> LOCATION: (9)..(9)
<223> OTHER INFORMATION: Xaa = Ser, Thr, or Cys

<400> SEQUENCE: 54

Xaa Xaa Xaa Xaa Xaa Xaa Xaa Xaa Xaa
1               5

<210> SEQ ID NO 55
<211> LENGTH: 9
<212> TYPE: PRT
<213> ORGANISM: Artificial Sequence
<220> FEATURE:
<223> OTHER INFORMATION: Sequence comprised in the intein C-terminal
      domain
<220> FEATURE:
<221> NAME/KEY: VARIANT
<222> LOCATION: (1)..(1)
<223> OTHER INFORMATION: Xaa = Ala, Val, Ile, or Cys
<220> FEATURE:
<221> NAME/KEY: MISC_FEATURE
<222> LOCATION: (1)..(8)
<223> OTHER INFORMATION: intein sequence
<220> FEATURE:
<221> NAME/KEY: VARIANT
<222> LOCATION: (2)..(2)
<223> OTHER INFORMATION: Xaa = Asn or Arg
<220> FEATURE:
<221> NAME/KEY: VARIANT
<222> LOCATION: (3)..(3)
<223> OTHER INFORMATION: Xaa = Gly, Asp, Ala, or Asn
<220> FEATURE:
<221> NAME/KEY: VARIANT
<222> LOCATION: (4)..(4)
<223> OTHER INFORMATION: Xaa = Ile, Phe, or Thr
<220> FEATURE:
<221> NAME/KEY: VARIANT
<222> LOCATION: (5)..(5)
<223> OTHER INFORMATION: Xaa = Leu or Val
<220> FEATURE:
<221> NAME/KEY: VARIANT
<222> LOCATION: (6)..(6)
<223> OTHER INFORMATION: Xaa = Val, Ile, or Thr
<220> FEATURE:
<221> NAME/KEY: VARIANT
<222> LOCATION: (7)..(7)
<223> OTHER INFORMATION: Xaa = His
<220> FEATURE:
<221> NAME/KEY: VARIANT
<222> LOCATION: (8)..(8)
<223> OTHER INFORMATION: Xaa = Asn
<220> FEATURE:
<221> NAME/KEY: VARIANT
<222> LOCATION: (9)..(9)
<223> OTHER INFORMATION: Xaa = Ser, Thr, or Cys
<220> FEATURE:
<221> NAME/KEY: MISC_FEATURE
<222> LOCATION: (9)..(9)
<223> OTHER INFORMATION: first amino acid of the extein

<400> SEQUENCE: 55

Xaa Xaa Xaa Xaa Xaa Xaa Xaa Xaa Xaa
```

<210> SEQ ID NO 56
<211> LENGTH: 223
<212> TYPE: PRT
<213> ORGANISM: Artificial Sequence
<220> FEATURE:
<223> OTHER INFORMATION: GP-41.1 C1A N-fragment Protein

<400> SEQUENCE: 56

```
Met Ala Ser Trp Ser His Pro Gln Phe Glu Lys Ala Ser Lys Glu Thr
1               5                   10                  15
Phe Thr His Tyr Gln Pro Gln Gly Asn Ser Asp Pro Ala His Thr Ala
                20                  25                  30
Thr Ala Pro Gly Gly Leu Ser Ala Lys Ala Pro Ala Met Thr Pro Leu
            35                  40                  45
Met Leu Asp Thr Ser Ser Arg Lys Leu Val Ala Trp Asp Gly Thr Thr
    50                  55                  60
Asp Gly Ala Ala Val Gly Ile Leu Ala Val Ala Ala Asp Gln Thr Ser
65                  70                  75                  80
Thr Thr Leu Thr Phe Tyr Lys Ser Gly Thr Phe Arg Tyr Glu Asp Val
                85                  90                  95
Leu Trp Pro Glu Ala Ala Ser Asp Glu Thr Lys Lys Arg Thr Ala Phe
            100                 105                 110
Ala Gly Thr Ala Ile Ser Ile Val Gly Ser Thr Arg Ser Gly Tyr Ala
        115                 120                 125
Leu Asp Leu Lys Thr Gln Val Gln Thr Pro Gly Met Lys Glu Ile
    130                 135                 140
Ser Asn Ile Gln Val Gly Asp Leu Val Leu Ser Asn Thr Gly Tyr Asn
145                 150                 155                 160
Glu Val Leu Asn Val Phe Pro Lys Ser Lys Lys Ser Tyr Lys Ile
                165                 170                 175
Thr Leu Glu Asp Gly Lys Glu Ile Ile Cys Ser Glu Glu His Leu Phe
            180                 185                 190
Pro Thr Gln Thr Gly Glu Met Asn Ile Ser Gly Gly Leu Lys Glu Gly
        195                 200                 205
Met Cys Leu Tyr Val Lys Glu Gly Gly His His His His His
    210                 215                 220
```

<210> SEQ ID NO 57
<211> LENGTH: 224
<212> TYPE: PRT
<213> ORGANISM: Artificial Sequence
<220> FEATURE:
<223> OTHER INFORMATION: GP 41.8 C1A N-fragment PROTEIN

<400> SEQUENCE: 57

```
Met Ala Ser Trp Ser His Pro Gln Phe Glu Lys Ala Ser Lys Glu Thr
1               5                   10                  15
Phe Thr His Tyr Gln Pro Gln Gly Asn Ser Asp Pro Ala His Thr Ala
                20                  25                  30
Thr Ala Pro Gly Gly Leu Ser Ala Lys Ala Pro Ala Met Thr Pro Leu
            35                  40                  45
Met Leu Asp Thr Ser Ser Arg Lys Leu Val Ala Trp Asp Gly Thr Thr
    50                  55                  60
Asp Gly Ala Ala Val Gly Ile Leu Ala Val Ala Ala Asp Gln Thr Ser
65                  70                  75                  80
```

```
Thr Thr Leu Thr Phe Tyr Lys Ser Gly Thr Phe Arg Tyr Glu Asp Val
                85                  90                  95

Leu Trp Pro Glu Ala Ala Ser Asp Glu Thr Lys Lys Arg Thr Ala Phe
        100                 105                 110

Ala Gly Thr Ala Ile Ser Ile Val Gly Ser Ser Gln Leu Asn Arg Ala
            115                 120                 125

Leu Ser Leu Asp Thr Met Val Val Thr Asn Gly Lys Ala Ile Glu Ile
    130                 135                 140

Arg Asp Val Lys Val Gly Asp Trp Leu Glu Ser Glu Cys Gly Pro Val
145                 150                 155                 160

Gln Val Thr Glu Val Leu Pro Ile Ile Lys Gln Pro Val Phe Glu Ile
                165                 170                 175

Val Leu Lys Ser Gly Lys Lys Ile Arg Val Ser Ala Asn His Lys Phe
            180                 185                 190

Pro Thr Lys Asp Gly Leu Lys Thr Ile Asn Ser Gly Leu Lys Val Gly
        195                 200                 205

Asp Phe Leu Arg Ser Arg Ala Lys Gly Gly His His His His His His
    210                 215                 220
```

<210> SEQ ID NO 58
<211> LENGTH: 240
<212> TYPE: PRT
<213> ORGANISM: Artificial Sequence
<220> FEATURE:
<223> OTHER INFORMATION: NrdJ1 C1A N-term PROTEIN

<400> SEQUENCE: 58

```
Met Ala Ser Trp Ser His Pro Gln Phe Glu Lys Ala Ser Lys Glu Thr
1               5                   10                  15

Phe Thr His Tyr Gln Pro Gln Gly Asn Ser Asp Pro Ala His Thr Ala
                20                  25                  30

Thr Ala Pro Gly Gly Leu Ser Ala Lys Ala Pro Ala Met Thr Pro Leu
            35                  40                  45

Met Leu Asp Thr Ser Ser Arg Lys Leu Val Ala Trp Asp Gly Thr Thr
    50                  55                  60

Asp Gly Ala Ala Val Gly Ile Leu Ala Val Ala Ala Asp Gln Thr Ser
65                  70                  75                  80

Thr Thr Leu Thr Phe Tyr Lys Ser Gly Thr Phe Arg Tyr Glu Asp Val
                85                  90                  95

Leu Trp Pro Glu Ala Ala Ser Asp Glu Thr Lys Lys Arg Thr Ala Phe
            100                 105                 110

Ala Gly Thr Ala Ile Ser Ile Val Gly Ser Gly Thr Asn Pro Cys Ala
            115                 120                 125

Leu Val Gly Ser Ser Glu Ile Ile Thr Arg Asn Tyr Gly Lys Thr Thr
    130                 135                 140

Ile Lys Glu Val Val Glu Ile Phe Asp Asn Asp Lys Asn Ile Gln Val
145                 150                 155                 160

Leu Ala Phe Asn Thr His Thr Asp Asn Ile Glu Trp Ala Pro Ile Lys
                165                 170                 175

Ala Ala Gln Leu Thr Arg Pro Asn Ala Glu Leu Val Glu Leu Glu Ile
            180                 185                 190

Asn Thr Leu His Gly Val Lys Thr Ile Arg Cys Thr Pro Asp His Pro
        195                 200                 205

Val Tyr Thr Lys Asn Arg Asp Tyr Val Arg Ala Asp Glu Leu Thr Asp
    210                 215                 220
```

```
Asp Asp Glu Leu Val Val Ala Ile Gly Gly His His His His His His
225                 230                 235                 240
```

```
<210> SEQ ID NO 59
<211> LENGTH: 236
<212> TYPE: PRT
<213> ORGANISM: Artificial Sequence
<220> FEATURE:
<223> OTHER INFORMATION: IMPDH C1A N-term PROTEIN

<400> SEQUENCE: 59

Met Ala Ser Trp Ser His Pro Gln Phe Glu Lys Ala Ser Lys Glu Thr
1               5                   10                  15

Phe Thr His Tyr Gln Pro Gln Gly Asn Ser Asp Pro Ala His Thr Ala
                20                  25                  30

Thr Ala Pro Gly Gly Leu Ser Ala Lys Ala Pro Ala Met Thr Pro Leu
            35                  40                  45

Met Leu Asp Thr Ser Ser Arg Lys Leu Val Ala Trp Asp Gly Thr Thr
    50                  55                  60

Asp Gly Ala Ala Val Gly Ile Leu Ala Val Ala Ala Asp Gln Thr Ser
65                  70                  75                  80

Thr Thr Leu Thr Phe Tyr Lys Ser Gly Thr Phe Arg Tyr Glu Asp Val
                85                  90                  95

Leu Trp Pro Glu Ala Ala Ser Asp Glu Thr Lys Lys Arg Thr Ala Phe
            100                 105                 110

Ala Gly Thr Ala Ile Ser Ile Val Gly Ser Gly Ile Gly Gly Gly Ala
        115                 120                 125

Phe Val Pro Gly Thr Leu Val Asn Thr Glu Asn Gly Leu Lys Lys Ile
    130                 135                 140

Glu Glu Ile Lys Val Gly Asp Lys Val Phe Ser His Thr Gly Lys Leu
145                 150                 155                 160

Gln Glu Val Val Asp Thr Leu Ile Phe Asp Arg Asp Glu Glu Ile Ile
                165                 170                 175

Ser Ile Asn Gly Ile Asp Cys Thr Lys Asn His Glu Phe Tyr Val Ile
            180                 185                 190

Asp Lys Glu Asn Ala Asn Arg Val Asn Glu Asp Asn Ile His Leu Phe
        195                 200                 205

Ala Arg Trp Val His Ala Glu Glu Leu Asp Met Lys Lys His Leu Leu
    210                 215                 220

Ile Glu Leu Glu Gly Gly His His His His His
225                 230                 235
```

```
<210> SEQ ID NO 60
<211> LENGTH: 165
<212> TYPE: PRT
<213> ORGANISM: Artificial Sequence
<220> FEATURE:
<223> OTHER INFORMATION: GP41.1 deltaext C-fragment Protein

<400> SEQUENCE: 60

Met Gly Lys Asn Ser Met Met Leu Lys Lys Ile Leu Lys Ile Glu Glu
1               5                   10                  15

Leu Asp Glu Arg Glu Leu Ile Asp Ile Glu Val Ser Gly Asn His Leu
                20                  25                  30

Phe Tyr Ala Asn Asp Ile Leu Thr His Asn Gly Thr Gly Ser Asp Lys
            35                  40                  45

Ile Ile His Leu Thr Asp Asp Ser Phe Asp Thr Asp Val Leu Lys Ala
        50                  55                  60
```

```
Asp Gly Ala Ile Leu Val Asp Phe Trp Ala His Trp Cys Gly Pro Cys
 65                  70                  75                  80

Lys Met Ile Ala Pro Ile Leu Asp Glu Ile Ala Asp Glu Tyr Gln Gly
                 85                  90                  95

Lys Leu Thr Val Ala Lys Leu Asn Ile Asp His Asn Pro Gly Thr Ala
            100                 105                 110

Pro Lys Tyr Gly Ile Arg Gly Ile Pro Thr Leu Leu Phe Lys Asn
        115                 120                 125

Gly Glu Val Ala Ala Thr Lys Val Gly Ala Leu Ser Lys Gly Gln Leu
    130                 135                 140

Lys Glu Phe Leu Asp Ala Asn Leu Ala Gly Ser Glu Phe Arg Ser His
145                 150                 155                 160

His His His His His
            165

<210> SEQ ID NO 61
<211> LENGTH: 168
<212> TYPE: PRT
<213> ORGANISM: Artificial Sequence
<220> FEATURE:
<223> OTHER INFORMATION: GP41.8 deltaext C-term PROTEIN

<400> SEQUENCE: 61

Met Cys Glu Ile Phe Glu Asn Glu Ile Asp Trp Asp Glu Ile Ala Ser
1               5                  10                  15

Ile Glu Tyr Val Gly Val Glu Glu Thr Ile Asp Ile Asn Val Thr Asn
            20                  25                  30

Asp Arg Leu Phe Phe Ala Asn Gly Ile Leu Thr His Asn Gly Thr Gly
        35                  40                  45

Ser Asp Lys Ile Ile His Leu Thr Asp Asp Ser Phe Thr Asp Val
    50                  55                  60

Leu Lys Ala Asp Gly Ala Ile Leu Val Asp Phe Trp Ala His Trp Cys
 65                  70                  75                  80

Gly Pro Cys Lys Met Ile Ala Pro Ile Leu Asp Glu Ile Ala Asp Glu
                 85                  90                  95

Tyr Gln Gly Lys Leu Thr Val Ala Lys Leu Asn Ile Asp His Asn Pro
            100                 105                 110

Gly Thr Ala Pro Lys Tyr Gly Ile Arg Gly Ile Pro Thr Leu Leu Leu
        115                 120                 125

Phe Lys Asn Gly Glu Val Ala Ala Thr Lys Val Gly Ala Leu Ser Lys
    130                 135                 140

Gly Gln Leu Lys Glu Phe Leu Asp Ala Asn Leu Ala Gly Ser Glu Phe
145                 150                 155                 160

Arg Ser His His His His His His
            165

<210> SEQ ID NO 62
<211> LENGTH: 163
<212> TYPE: PRT
<213> ORGANISM: Artificial Sequence
<220> FEATURE:
<223> OTHER INFORMATION: NrdJ1 deltaext C-term PROTEIN

<400> SEQUENCE: 62

Met Glu Ala Lys Thr Tyr Ile Gly Lys Leu Lys Ser Arg Lys Ile Val
1               5                  10                  15

Ser Asn Glu Asp Thr Tyr Asp Ile Gln Thr Ser Thr His Asn Phe Phe
```

```
                    20                  25                  30
Ala Asn Asp Ile Leu Val His Asn Gly Thr Gly Ser Asp Lys Ile Ile
            35                  40                  45

His Leu Thr Asp Asp Ser Phe Asp Thr Asp Val Leu Lys Ala Asp Gly
    50                  55                  60

Ala Ile Leu Val Asp Phe Trp Ala His Trp Cys Gly Pro Cys Lys Met
65                  70                  75                  80

Ile Ala Pro Ile Leu Asp Glu Ile Ala Asp Glu Tyr Gln Gly Lys Leu
                85                  90                  95

Thr Val Ala Lys Leu Asn Ile Asp His Asn Pro Gly Thr Ala Pro Lys
            100                 105                 110

Tyr Gly Ile Arg Gly Ile Pro Thr Leu Leu Leu Phe Lys Asn Gly Glu
        115                 120                 125

Val Ala Ala Thr Lys Val Gly Ala Leu Ser Lys Gly Gln Leu Lys Glu
    130                 135                 140

Phe Leu Asp Ala Asn Leu Ala Gly Ser Glu Phe Arg Ser His His His
145                 150                 155                 160

His His His

<210> SEQ ID NO 63
<211> LENGTH: 163
<212> TYPE: PRT
<213> ORGANISM: Artificial Sequence
<220> FEATURE:
<223> OTHER INFORMATION: IMPDH deltaext C-term PROTEIN

<400> SEQUENCE: 63

Met Lys Phe Lys Leu Lys Glu Ile Thr Ser Ile Glu Thr Lys His Tyr
1               5                   10                  15

Lys Gly Lys Val His Asp Leu Thr Val Asn Gln Asp His Ser Tyr Asn
            20                  25                  30

Val Arg Gly Thr Val Val His Asn Gly Thr Gly Ser Asp Lys Ile Ile
        35                  40                  45

His Leu Thr Asp Asp Ser Phe Asp Thr Asp Val Leu Lys Ala Asp Gly
    50                  55                  60

Ala Ile Leu Val Asp Phe Trp Ala His Trp Cys Gly Pro Cys Lys Met
65                  70                  75                  80

Ile Ala Pro Ile Leu Asp Glu Ile Ala Asp Glu Tyr Gln Gly Lys Leu
                85                  90                  95

Thr Val Ala Lys Leu Asn Ile Asp His Asn Pro Gly Thr Ala Pro Lys
            100                 105                 110

Tyr Gly Ile Arg Gly Ile Pro Thr Leu Leu Leu Phe Lys Asn Gly Glu
        115                 120                 125

Val Ala Ala Thr Lys Val Gly Ala Leu Ser Lys Gly Gln Leu Lys Glu
    130                 135                 140

Phe Leu Asp Ala Asn Leu Ala Gly Ser Glu Phe Arg Ser His His His
145                 150                 155                 160

His His His

<210> SEQ ID NO 64
<211> LENGTH: 106
<212> TYPE: PRT
<213> ORGANISM: Artificial sequence
<220> FEATURE:
<223> OTHER INFORMATION: N-terminal region of the NrdA2 intein

<400> SEQUENCE: 64
```

-continued

Cys Leu Thr Gly Asp Ala Lys Ile Asp Val Leu Ile Asp Asn Ile Pro
1               5                   10                  15

Ile Ser Gln Ile Ser Leu Glu Glu Val Val Asn Leu Phe Asn Glu Gly
                20                  25                  30

Lys Glu Ile Tyr Val Leu Ser Tyr Asn Ile Asp Thr Lys Glu Val Glu
            35                  40                  45

Tyr Lys Glu Ile Ser Asp Ala Gly Leu Ile Ser Glu Ser Ala Glu Val
        50                  55                  60

Leu Glu Ile Ile Asp Glu Thr Gly Gln Lys Ile Val Cys Thr Pro
65                  70                  75                  80

Asp His Lys Val Tyr Thr Leu Asn Arg Gly Tyr Val Ser Ala Lys Asp
                85                  90                  95

Leu Lys Glu Asp Asp Glu Leu Val Phe Ser
                100                 105

<210> SEQ ID NO 65
<211> LENGTH: 34
<212> TYPE: PRT
<213> ORGANISM: Artificial sequence
<220> FEATURE:
<223> OTHER INFORMATION: C-terminal region of the NrdA2 intein

<400> SEQUENCE: 65

Met Gly Leu Lys Ile Ile Lys Arg Glu Ser Lys Glu Pro Val Phe Asp
1               5                   10                  15

Ile Thr Val Lys Asp Asn Ser Asn Phe Phe Ala Asn Asn Ile Leu Val
                20                  25                  30

His Asn

<210> SEQ ID NO 66
<211> LENGTH: 166
<212> TYPE: PRT
<213> ORGANISM: Artificial sequence
<220> FEATURE:
<223> OTHER INFORMATION: G1C(S)

<400> SEQUENCE: 66

Met Gly Lys Asn Ser Met Met Leu Lys Lys Ile Leu Lys Ile Glu Glu
1               5                   10                  15

Leu Asp Glu Arg Glu Leu Ile Asp Ile Glu Val Ser Gly Asn His Leu
                20                  25                  30

Phe Tyr Ala Asn Asp Ile Leu Thr His Asn Ser Gly Thr Gly Ser Asp
            35                  40                  45

Lys Ile Ile His Leu Thr Asp Asp Ser Phe Asp Thr Asp Val Leu Lys
        50                  55                  60

Ala Asp Gly Ala Ile Leu Val Asp Phe Trp Ala His Trp Cys Gly Pro
65                  70                  75                  80

Cys Lys Met Ile Ala Pro Ile Leu Asp Glu Ile Ala Asp Glu Tyr Gln
                85                  90                  95

Gly Lys Leu Thr Val Ala Lys Leu Asn Ile Asp His Asn Pro Gly Thr
                100                 105                 110

Ala Pro Lys Tyr Gly Ile Arg Gly Ile Pro Thr Leu Leu Leu Phe Lys
            115                 120                 125

Asn Gly Glu Val Ala Ala Thr Lys Val Gly Ala Leu Ser Lys Gly Gln
        130                 135                 140

Leu Lys Glu Phe Leu Asp Ala Asn Leu Ala Gly Ser Glu Phe Arg Ser
145                 150                 155                 160

His His His His His His
            165

<210> SEQ ID NO 67
<211> LENGTH: 218
<212> TYPE: PRT
<213> ORGANISM: Artificial
<220> FEATURE:
<223> OTHER INFORMATION: G1N(deltaext)

<400> SEQUENCE: 67

Met Ala Ser Trp Ser His Pro Gln Phe Glu Lys Ala Ser Lys Glu Thr
1               5                   10                  15

Phe Thr His Tyr Gln Pro Gln Gly Asn Ser Asp Pro Ala His Thr Ala
            20                  25                  30

Thr Ala Pro Gly Gly Leu Ser Ala Lys Ala Pro Ala Met Thr Pro Leu
        35                  40                  45

Met Leu Asp Thr Ser Ser Arg Lys Leu Val Ala Trp Asp Gly Thr Thr
50                  55                  60

Asp Gly Ala Ala Val Gly Ile Leu Ala Val Ala Ala Asp Gln Thr Ser
65                  70                  75                  80

Thr Thr Leu Thr Phe Tyr Lys Ser Gly Thr Phe Arg Tyr Glu Asp Val
                85                  90                  95

Leu Trp Pro Glu Ala Ala Ser Asp Glu Thr Lys Lys Arg Thr Ala Phe
            100                 105                 110

Ala Gly Thr Ala Ile Ser Ile Val Gly Ser Cys Leu Asp Leu Lys Thr
        115                 120                 125

Gln Val Gln Thr Pro Gln Gly Met Lys Glu Ile Ser Asn Ile Gln Val
130                 135                 140

Gly Asp Leu Val Leu Ser Asn Thr Gly Tyr Asn Glu Val Leu Asn Val
145                 150                 155                 160

Phe Pro Lys Ser Lys Lys Ser Tyr Lys Ile Thr Leu Glu Asp Gly
                165                 170                 175

Lys Glu Ile Ile Cys Ser Glu Glu His Leu Phe Pro Thr Gln Thr Gly
            180                 185                 190

Glu Met Asn Ile Ser Gly Gly Leu Lys Gly Met Cys Leu Tyr Val
        195                 200                 205

Lys Glu Gly Gly His His His His His His
    210                 215

<210> SEQ ID NO 68
<211> LENGTH: 170
<212> TYPE: PRT
<213> ORGANISM: Artificial
<220> FEATURE:
<223> OTHER INFORMATION: GP41.1 N to A C-fragment protein

<400> SEQUENCE: 68

Met Gly Lys Asn Ser Met Met Leu Lys Lys Ile Leu Lys Ile Glu Glu
1               5                   10                  15

Leu Asp Glu Arg Glu Leu Ile Asp Ile Glu Val Ser Gly Asn His Leu
            20                  25                  30

Phe Tyr Ala Asn Asp Ile Leu Thr His Ala Ser Ser Asp Val Gly
        35                  40                  45

Thr Gly Ser Asp Lys Ile Ile His Leu Thr Asp Asp Ser Phe Asp Thr
50                  55                  60

Asp Val Leu Lys Ala Asp Gly Ala Ile Leu Val Asp Phe Trp Ala His

```
                65                  70                  75                  80

Trp Cys Gly Pro Cys Lys Met Ile Ala Pro Ile Leu Asp Glu Ile Ala
                85                  90                  95

Asp Glu Tyr Gln Gly Lys Leu Thr Val Ala Lys Leu Asn Ile Asp His
               100                 105                 110

Asn Pro Gly Thr Ala Pro Lys Tyr Gly Ile Arg Gly Ile Pro Thr Leu
               115                 120                 125

Leu Leu Phe Lys Asn Gly Glu Val Ala Ala Thr Lys Val Gly Ala Leu
130                 135                 140

Ser Lys Gly Gln Leu Lys Glu Phe Leu Asp Ala Asn Leu Ala Gly Ser
145                 150                 155                 160

Glu Phe Arg Ser His His His His His His
                165                 170

<210> SEQ ID NO 69
<211> LENGTH: 173
<212> TYPE: PRT
<213> ORGANISM: Artificial
<220> FEATURE:
<223> OTHER INFORMATION: GP41-8 N to A C-terminal fragment

<400> SEQUENCE: 69

Met Cys Glu Ile Phe Glu Asn Glu Ile Asp Trp Asp Glu Ile Ala Ser
1               5                   10                  15

Ile Glu Tyr Val Gly Val Glu Thr Ile Asp Ile Asn Val Thr Asn
                20                  25                  30

Asp Arg Leu Phe Phe Ala Asn Gly Ile Leu Thr His Ala Ser Ala Val
                35                  40                  45

Glu Glu Gly Thr Gly Ser Asp Lys Ile Ile His Leu Thr Asp Asp Ser
            50                  55                  60

Phe Asp Thr Asp Val Leu Lys Ala Asp Gly Ala Ile Leu Val Asp Phe
65                  70                  75                  80

Trp Ala His Trp Cys Gly Pro Cys Lys Met Ile Ala Pro Ile Leu Asp
                85                  90                  95

Glu Ile Ala Asp Glu Tyr Gln Gly Lys Leu Thr Val Ala Lys Leu Asn
                100                 105                 110

Ile Asp His Asn Pro Gly Thr Ala Pro Lys Tyr Gly Ile Arg Gly Ile
            115                 120                 125

Pro Thr Leu Leu Leu Phe Lys Asn Gly Glu Val Ala Ala Thr Lys Val
130                 135                 140

Gly Ala Leu Ser Lys Gly Gln Leu Lys Glu Phe Leu Asp Ala Asn Leu
145                 150                 155                 160

Ala Gly Ser Glu Phe Arg Ser His His His His His
                165                 170

<210> SEQ ID NO 70
<211> LENGTH: 168
<212> TYPE: PRT
<213> ORGANISM: Artificial
<220> FEATURE:
<223> OTHER INFORMATION: NrdJ1 N to A C-terminal fragment

<400> SEQUENCE: 70

Met Glu Ala Lys Thr Tyr Ile Gly Lys Leu Lys Ser Arg Lys Ile Val
1               5                   10                  15

Ser Asn Glu Asp Thr Tyr Asp Ile Gln Thr Ser Thr His Asn Phe Phe
                20                  25                  30
```

```
Ala Asn Asp Ile Leu Val His Ala Ser Glu Ile Val Leu Gly Thr Gly
         35                  40                  45

Ser Asp Lys Ile Ile His Leu Thr Asp Ser Phe Asp Thr Asp Val
 50                  55                  60

Leu Lys Ala Asp Gly Ala Ile Leu Val Asp Phe Trp Ala His Trp Cys
 65                  70                  75                  80

Gly Pro Cys Lys Met Ile Ala Pro Ile Leu Asp Glu Ile Ala Asp Glu
                 85                  90                  95

Tyr Gln Gly Lys Leu Thr Val Ala Lys Leu Asn Ile Asp His Asn Pro
                100                 105                 110

Gly Thr Ala Pro Lys Tyr Gly Ile Arg Gly Ile Pro Thr Leu Leu Leu
                115                 120                 125

Phe Lys Asn Gly Glu Val Ala Ala Thr Lys Val Gly Ala Leu Ser Lys
130                 135                 140

Gly Gln Leu Lys Glu Phe Leu Asp Ala Asn Leu Ala Gly Ser Glu Phe
145                 150                 155                 160

Arg Ser His His His His His His
                165

<210> SEQ ID NO 71
<211> LENGTH: 168
<212> TYPE: PRT
<213> ORGANISM: Artificial
<220> FEATURE:
<223> OTHER INFORMATION: IMPDH1 N to A C-terminal fragment

<400> SEQUENCE: 71

Met Lys Phe Lys Leu Lys Glu Ile Thr Ser Ile Glu Thr Lys His Tyr
 1               5                  10                  15

Lys Gly Lys Val His Asp Leu Thr Val Asn Gln Asp His Ser Tyr Asn
                20                  25                  30

Val Arg Gly Thr Val Val His Ala Ser Ile Cys Ser Thr Gly Thr Gly
             35                  40                  45

Ser Asp Lys Ile Ile His Leu Thr Asp Asp Ser Phe Asp Thr Asp Val
 50                  55                  60

Leu Lys Ala Asp Gly Ala Ile Leu Val Asp Phe Trp Ala His Trp Cys
 65                  70                  75                  80

Gly Pro Cys Lys Met Ile Ala Pro Ile Leu Asp Glu Ile Ala Asp Glu
                 85                  90                  95

Tyr Gln Gly Lys Leu Thr Val Ala Lys Leu Asn Ile Asp His Asn Pro
                100                 105                 110

Gly Thr Ala Pro Lys Tyr Gly Ile Arg Gly Ile Pro Thr Leu Leu Leu
                115                 120                 125

Phe Lys Asn Gly Glu Val Ala Ala Thr Lys Val Gly Ala Leu Ser Lys
130                 135                 140

Gly Gln Leu Lys Glu Phe Leu Asp Ala Asn Leu Ala Gly Ser Glu Phe
145                 150                 155                 160

Arg Ser His His His His His His
                165

<210> SEQ ID NO 72
<211> LENGTH: 170
<212> TYPE: PRT
<213> ORGANISM: Artificial
<220> FEATURE:
<223> OTHER INFORMATION: GP41.1 N/S to A C-terminal fragment

<400> SEQUENCE: 72
```

```
Met Gly Lys Asn Ser Met Met Leu Lys Lys Ile Leu Lys Ile Glu Glu
1               5                   10                  15

Leu Asp Glu Arg Glu Leu Ile Asp Ile Glu Val Ser Gly Asn His Leu
            20                  25                  30

Phe Tyr Ala Asn Asp Ile Leu Thr His Ala Ala Ser Ser Asp Val Gly
            35                  40                  45

Thr Gly Ser Asp Lys Ile Ile His Leu Thr Asp Ser Phe Asp Thr
        50                  55                  60

Asp Val Leu Lys Ala Asp Gly Ala Ile Leu Val Asp Phe Trp Ala His
65                  70                  75                  80

Trp Cys Gly Pro Cys Lys Met Ile Ala Pro Ile Leu Asp Glu Ile Ala
                85                  90                  95

Asp Glu Tyr Gln Gly Lys Leu Thr Val Ala Lys Leu Asn Ile Asp His
                100                 105                 110

Asn Pro Gly Thr Ala Pro Lys Tyr Gly Ile Arg Gly Ile Pro Thr Leu
            115                 120                 125

Leu Leu Phe Lys Asn Gly Glu Val Ala Ala Thr Lys Val Gly Ala Leu
        130                 135                 140

Ser Lys Gly Gln Leu Lys Glu Phe Leu Asp Ala Asn Leu Ala Gly Ser
145                 150                 155                 160

Glu Phe Arg Ser His His His His His
                165                 170

<210> SEQ ID NO 73
<211> LENGTH: 173
<212> TYPE: PRT
<213> ORGANISM: Artificial
<220> FEATURE:
<223> OTHER INFORMATION: GP41.8 N/S to A C-terminal fragment

<400> SEQUENCE: 73

Met Cys Glu Ile Phe Glu Asn Glu Ile Asp Trp Asp Glu Ile Ala Ser
1               5                   10                  15

Ile Glu Tyr Val Gly Val Glu Glu Thr Ile Asp Ile Asn Val Thr Asn
            20                  25                  30

Asp Arg Leu Phe Phe Ala Asn Gly Ile Leu Thr His Ala Ala Ala Val
            35                  40                  45

Glu Glu Gly Thr Gly Ser Asp Lys Ile Ile His Leu Thr Asp Asp Ser
        50                  55                  60

Phe Asp Thr Asp Val Leu Lys Ala Asp Gly Ala Ile Leu Val Asp Phe
65                  70                  75                  80

Trp Ala His Trp Cys Gly Pro Cys Lys Met Ile Ala Pro Ile Leu Asp
                85                  90                  95

Glu Ile Ala Asp Glu Tyr Gln Gly Lys Leu Thr Val Ala Lys Leu Asn
                100                 105                 110

Ile Asp His Asn Pro Gly Thr Ala Pro Lys Tyr Gly Ile Arg Gly Ile
            115                 120                 125

Pro Thr Leu Leu Leu Phe Lys Asn Gly Glu Val Ala Ala Thr Lys Val
        130                 135                 140

Gly Ala Leu Ser Lys Gly Gln Leu Lys Glu Phe Leu Asp Ala Asn Leu
145                 150                 155                 160

Ala Gly Ser Glu Phe Arg Ser His His His His His
                165                 170

<210> SEQ ID NO 74
```

```
<211> LENGTH: 168
<212> TYPE: PRT
<213> ORGANISM: Artificial
<220> FEATURE:
<223> OTHER INFORMATION: NrdJ1 N/S to A C-terminal fragment

<400> SEQUENCE: 74

Met Glu Ala Lys Thr Tyr Ile Gly Lys Leu Lys Ser Arg Lys Ile Val
1               5                   10                  15

Ser Asn Glu Asp Thr Tyr Asp Ile Gln Thr Ser Thr His Asn Phe Phe
            20                  25                  30

Ala Asn Asp Ile Leu Val His Ala Ala Glu Ile Val Leu Gly Thr Gly
        35                  40                  45

Ser Asp Lys Ile Ile His Leu Thr Asp Asp Ser Phe Asp Thr Asp Val
50                  55                  60

Leu Lys Ala Asp Gly Ala Ile Leu Val Asp Phe Trp Ala His Trp Cys
65                  70                  75                  80

Gly Pro Cys Lys Met Ile Ala Pro Ile Leu Asp Glu Ile Ala Asp Glu
                85                  90                  95

Tyr Gln Gly Lys Leu Thr Val Ala Lys Leu Asn Ile Asp His Asn Pro
            100                 105                 110

Gly Thr Ala Pro Lys Tyr Gly Ile Arg Gly Ile Pro Thr Leu Leu Leu
        115                 120                 125

Phe Lys Asn Gly Glu Val Ala Ala Thr Lys Val Gly Ala Leu Ser Lys
130                 135                 140

Gly Gln Leu Lys Glu Phe Leu Asp Ala Asn Leu Ala Gly Ser Glu Phe
145                 150                 155                 160

Arg Ser His His His His His His
                165

<210> SEQ ID NO 75
<211> LENGTH: 168
<212> TYPE: PRT
<213> ORGANISM: Artificial
<220> FEATURE:
<223> OTHER INFORMATION: IMPDH1 N/S to A C-terminal fragment

<400> SEQUENCE: 75

Met Lys Phe Lys Leu Lys Glu Ile Thr Ser Ile Glu Thr Lys His Tyr
1               5                   10                  15

Lys Gly Lys Val His Asp Leu Thr Val Asn Gln Asp His Ser Tyr Asn
            20                  25                  30

Val Arg Gly Thr Val Val His Ala Ala Ile Cys Ser Thr Gly Thr Gly
        35                  40                  45

Ser Asp Lys Ile Ile His Leu Thr Asp Asp Ser Phe Asp Thr Asp Val
50                  55                  60

Leu Lys Ala Asp Gly Ala Ile Leu Val Asp Phe Trp Ala His Trp Cys
65                  70                  75                  80

Gly Pro Cys Lys Met Ile Ala Pro Ile Leu Asp Glu Ile Ala Asp Glu
                85                  90                  95

Tyr Gln Gly Lys Leu Thr Val Ala Lys Leu Asn Ile Asp His Asn Pro
            100                 105                 110

Gly Thr Ala Pro Lys Tyr Gly Ile Arg Gly Ile Pro Thr Leu Leu Leu
        115                 120                 125

Phe Lys Asn Gly Glu Val Ala Ala Thr Lys Val Gly Ala Leu Ser Lys
130                 135                 140

Gly Gln Leu Lys Glu Phe Leu Asp Ala Asn Leu Ala Gly Ser Glu Phe
```

```
145                 150                 155                 160
Arg Ser His His His His His
                165

<210> SEQ ID NO 76
<211> LENGTH: 109
<212> TYPE: PRT
<213> ORGANISM: bacteriophage lambda

<400> SEQUENCE: 76

Lys Glu Thr Phe Thr His Tyr Gln Pro Gln Gly Asn Ser Asp Pro Ala
1               5                   10                  15

His Thr Ala Thr Ala Pro Gly Gly Leu Ser Ala Lys Ala Pro Ala Met
            20                  25                  30

Thr Pro Leu Met Leu Asp Thr Ser Ser Arg Lys Leu Val Ala Trp Asp
        35                  40                  45

Gly Thr Thr Asp Gly Ala Ala Val Gly Ile Leu Ala Val Ala Ala Asp
    50                  55                  60

Gln Thr Ser Thr Thr Leu Thr Phe Tyr Lys Ser Gly Thr Phe Arg Tyr
65                  70                  75                  80

Glu Asp Val Leu Trp Pro Glu Ala Ala Ser Asp Glu Thr Lys Lys Arg
                85                  90                  95

Thr Ala Phe Ala Gly Thr Ala Ile Ser Ile Val Gly Ser
            100                 105

<210> SEQ ID NO 77
<211> LENGTH: 111
<212> TYPE: PRT
<213> ORGANISM: Escherichia coli

<400> SEQUENCE: 77

Gly Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala His Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp His Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser
            100                 105                 110

<210> SEQ ID NO 78
<211> LENGTH: 9
<212> TYPE: PRT
<213> ORGANISM: Artificial
<220> FEATURE:
<223> OTHER INFORMATION: C1-Box of the C-terminal region of the GP41-1
      intein

<400> SEQUENCE: 78

Ala Asn Asp Ile Leu Thr His Asn Ser
1               5

<210> SEQ ID NO 79
```

<211> LENGTH: 88
<212> TYPE: PRT
<213> ORGANISM: Artificial
<220> FEATURE:
<223> OTHER INFORMATION: gp41-1 N-intein

<400> SEQUENCE: 79

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Lys Ser Tyr Lys
        35                  40                  45

Ile Thr Leu Glu Asp Gly Lys Glu Ile Ile Cys Ser Glu Glu His Leu
    50                  55                  60

Phe Pro Thr Gln Thr Gly Glu Met Asn Ile Ser Gly Leu Lys Glu
65                  70                  75                  80

Gly Met Cys Leu Tyr Val Lys Glu
                85

<210> SEQ ID NO 80
<211> LENGTH: 27
<212> TYPE: PRT
<213> ORGANISM: Artificial
<220> FEATURE:
<223> OTHER INFORMATION: gp41-2 N-intein

<400> SEQUENCE: 80

Cys Leu Asp Leu Lys Thr Gln Val Gln Thr Gln Gln Gly Leu Lys Asp
1               5                   10                  15

Ile Ser Asn Ile Gln Val Gly Asp Leu Val Leu
            20                  25

<210> SEQ ID NO 81
<211> LENGTH: 46
<212> TYPE: PRT
<213> ORGANISM: Artificial
<220> FEATURE:
<223> OTHER INFORMATION: gp41-3 N-intein

<400> SEQUENCE: 81

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Lys Ser
        35                  40                  45

<210> SEQ ID NO 82
<211> LENGTH: 88
<212> TYPE: PRT
<213> ORGANISM: Artificial
<220> FEATURE:
<223> OTHER INFORMATION: gp41-4 N-intein

<400> SEQUENCE: 82

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Lys Ser Tyr Lys
        35                  40                  45

Ile Thr Leu Glu Asp Gly Lys Glu Ile Ile Cys Ser Glu Glu His Leu
    50                  55                  60

Phe Pro Thr Gln Thr Gly Glu Met Asn Ile Ser Gly Gly Leu Lys Glu
65                  70                  75                  80

Gly Met Cys Leu Tyr Val Lys Glu
                85

<210> SEQ ID NO 83
<211> LENGTH: 88
<212> TYPE: PRT
<213> ORGANISM: Artificial
<220> FEATURE:
<223> OTHER INFORMATION: gp41-5 N-intein

<400> SEQUENCE: 83

Cys Leu Asp Leu Lys Thr Gln Val Gln Thr Pro Gln Gly Met Lys Glu
1               5                   10                  15

Ile Ser Asn Ile Gln Val Gly Asp Leu Val Leu Ser Asn Thr Gly Tyr
            20                  25                  30

Asn Glu Val Leu Asn Val Phe Pro Lys Ser Lys Lys Ser Tyr Lys
        35                  40                  45

Ile Thr Leu Glu Asp Gly Lys Glu Ile Ile Cys Ser Glu Glu His Leu
    50                  55                  60

Phe Pro Thr Gln Thr Gly Glu Met Asn Ile Ser Gly Gly Leu Lys Glu
65                  70                  75                  80

Gly Met Cys Leu Tyr Val Lys Glu
                85

<210> SEQ ID NO 84
<211> LENGTH: 43
<212> TYPE: PRT
<213> ORGANISM: Artificial
<220> FEATURE:
<223> OTHER INFORMATION: gp41-6 N-intein

<400> SEQUENCE: 84

Ser Tyr Lys Ile Thr Leu Glu Asp Gly Lys Glu Ile Ile Cys Ser Glu
1               5                   10                  15

Glu His Leu Phe Pro Thr Gln Asn Gly Glu Val Asn Ile Lys Gly Gly
            20                  25                  30

Leu Lys Glu Gly Met Cys Leu Tyr Val Lys Glu
            35                  40

<210> SEQ ID NO 85
<211> LENGTH: 88
<212> TYPE: PRT
<213> ORGANISM: Artificial
<220> FEATURE:
<223> OTHER INFORMATION: gp41-7 N-intein

<400> SEQUENCE: 85

Cys Leu Asp Leu Lys Thr Gln Val Gln Thr Pro Gln Gly Met Lys Glu
1               5                   10                  15

Leu Ser Asn Ile Gln Val Gly Asp Leu Val Leu Ser Asn Thr Gly Tyr
            20                  25                  30

Asn Gln Val Leu Asn Val Phe Pro Lys Ser Lys Lys Ser Tyr Lys
        35                  40                  45

Ile Thr Leu Glu Asp Gly Lys Glu Ile Ile Cys Ser Glu Glu His Leu
    50                  55                  60

Phe Pro Thr Gln Asn Gly Glu Val Asn Ile Lys Gly Gly Leu Lys Glu
65                  70                  75                  80

Gly Met Cys Leu Tyr Val Lys Glu
                85

<210> SEQ ID NO 86
<211> LENGTH: 89
<212> TYPE: PRT
<213> ORGANISM: Artificial
<220> FEATURE:
<223> OTHER INFORMATION: gp41-8 N-intein

<400> SEQUENCE: 86

Cys Leu Ser Leu Asp Thr Met Val Val Thr Asn Gly Lys Ala Ile Glu
1               5                   10                  15

Ile Arg Asp Val Lys Val Gly Asp Trp Leu Glu Ser Glu Cys Gly Pro
            20                  25                  30

Val Gln Val Thr Glu Val Leu Pro Ile Ile Lys Gln Pro Val Phe Glu
        35                  40                  45

Ile Val Leu Lys Ser Gly Lys Lys Ile Arg Val Ser Ala Asn His Lys
    50                  55                  60

Phe Pro Thr Lys Asp Gly Leu Lys Thr Ile Asn Ser Gly Leu Lys Val
65                  70                  75                  80

Gly Asp Phe Leu Arg Ser Arg Ala Lys
                85

<210> SEQ ID NO 87
<211> LENGTH: 101
<212> TYPE: PRT
<213> ORGANISM: Artificial
<220> FEATURE:
<223> OTHER INFORMATION: IMPDH-1 N-intein

<400> SEQUENCE: 87

Cys Phe Val Pro Gly Thr Leu Val Asn Thr Glu Asn Gly Leu Lys Lys
1               5                   10                  15

Ile Glu Glu Ile Lys Val Gly Asp Lys Val Phe Ser His Thr Gly Lys
            20                  25                  30

Leu Gln Glu Val Val Asp Thr Leu Ile Phe Asp Arg Asp Glu Glu Ile
        35                  40                  45

Ile Ser Ile Asn Gly Ile Asp Cys Thr Lys Asn His Glu Phe Tyr Val
    50                  55                  60

Ile Asp Lys Glu Asn Ala Asn Arg Val Asn Glu Asp Asn Ile His Leu
65                  70                  75                  80

Phe Ala Arg Trp Val His Ala Glu Glu Leu Asp Met Lys Lys His Leu
                85                  90                  95

Leu Ile Glu Leu Glu
            100

<210> SEQ ID NO 88
<211> LENGTH: 133
<212> TYPE: PRT
<213> ORGANISM: Artificial
<220> FEATURE:
<223> OTHER INFORMATION: NrdA-1 N-intein

<400> SEQUENCE: 88

Cys Val Ala Gly Asp Thr Lys Ile Lys Ile Lys Tyr Pro Glu Ser Val
1               5                   10                  15

Gly Asp Gln Tyr Gly Thr Trp Tyr Trp Asn Val Leu Glu Lys Glu Ile

```
                20                  25                  30
Gln Ile Glu Asp Leu Glu Asp Tyr Ile Ile Met Arg Glu Cys Glu Ile
            35                  40                  45
Tyr Asp Ser Asn Ala Pro Gln Ile Glu Val Leu Ser Tyr Asn Ile Glu
        50                  55                  60
Thr Gly Glu Gln Glu Trp Lys Pro Ile Thr Ala Phe Ala Gln Thr Ser
65                  70                  75                  80
Pro Lys Ala Lys Val Met Lys Ile Thr Asp Glu Glu Ser Gly Lys Ser
                85                  90                  95
Ile Val Val Thr Pro Glu His Gln Val Phe Thr Lys Asn Arg Gly Tyr
            100                 105                 110
Val Met Ala Lys Asp Leu Ile Glu Thr Asp Glu Pro Ile Ile Val Asn
        115                 120                 125
Lys Asp Met Asn Phe
        130

<210> SEQ ID NO 89
<211> LENGTH: 106
<212> TYPE: PRT
<213> ORGANISM: Artificial
<220> FEATURE:
<223> OTHER INFORMATION: NrdA-2 N-intein

<400> SEQUENCE: 89

Cys Leu Thr Gly Asp Ala Lys Ile Asp Val Leu Ile Asp Asn Ile Pro
1               5                   10                  15
Ile Ser Gln Ile Ser Leu Glu Glu Val Val Asn Leu Phe Asn Glu Gly
            20                  25                  30
Lys Glu Ile Tyr Val Leu Ser Tyr Asn Ile Asp Thr Lys Glu Val Glu
        35                  40                  45
Tyr Lys Glu Ile Ser Asp Ala Gly Leu Ile Ser Glu Ser Ala Glu Val
    50                  55                  60
Leu Glu Ile Ile Asp Glu Glu Thr Gly Gln Lys Ile Val Cys Thr Pro
65                  70                  75                  80
Asp His Lys Val Tyr Thr Leu Asn Arg Gly Tyr Val Ser Ala Lys Asp
                85                  90                  95
Leu Lys Glu Asp Asp Glu Leu Val Phe Ser
            100                 105

<210> SEQ ID NO 90
<211> LENGTH: 105
<212> TYPE: PRT
<213> ORGANISM: Artificial
<220> FEATURE:
<223> OTHER INFORMATION: NrdA-4 N-intein

<400> SEQUENCE: 90

Cys Leu Ala Gly Asp Thr Thr Val Thr Val Leu Glu Gly Asp Ile Val
1               5                   10                  15
Phe Glu Met Thr Leu Glu Asn Leu Val Ser Leu Tyr Lys Asn Val Phe
            20                  25                  30
Ser Val Ser Val Leu Ser Phe Asn Pro Glu Thr Gln Lys Gln Glu Phe
        35                  40                  45
Lys Pro Val Thr Asn Ala Ala Leu Met Asn Pro Glu Ser Lys Val Leu
    50                  55                  60
Lys Ile Thr Asp Ser Asp Thr Gly Lys Ser Ile Val Cys Thr Pro Asp
65                  70                  75                  80
```

His Lys Val Phe Thr Lys Asn Arg Gly Tyr Val Ile Ala Ser Glu Leu
                85                  90                  95

Asn Ala Glu Asp Ile Leu Glu Ile Lys
            100                 105

<210> SEQ ID NO 91
<211> LENGTH: 65
<212> TYPE: PRT
<213> ORGANISM: Artificial
<220> FEATURE:
<223> OTHER INFORMATION: NrdA-5 N-intein

<400> SEQUENCE: 91

His Thr Glu Thr Val Arg Arg Val Gly Thr Ile Thr Ala Phe Ala Gln
1               5                   10                  15

Thr Ser Pro Lys Ser Lys Val Met Lys Ile Thr Asp Glu Glu Ser Gly
                20                  25                  30

Asn Ser Ile Val Val Thr Pro Glu His Lys Val Phe Thr Lys Asn Arg
            35                  40                  45

Gly Tyr Val Met Ala Lys Asn Leu Val Glu Thr Asp Glu Leu Val Ile
        50                  55                  60

Asn
65

<210> SEQ ID NO 92
<211> LENGTH: 49
<212> TYPE: PRT
<213> ORGANISM: Artificial
<220> FEATURE:
<223> OTHER INFORMATION: NrdA-6 N-intein

<400> SEQUENCE: 92

Tyr Val Cys Ser Arg Asp Thr Thr Gly Phe Lys Leu Ile Cys Thr
1               5                   10                  15

Pro Asp His Met Ile Tyr Thr Lys Asn Arg Gly Tyr Ile Met Ala Lys
                20                  25                  30

Tyr Leu Lys Glu Asp Asp Glu Leu Leu Ile Asn Glu Ile His Leu Pro
            35                  40                  45

Thr

<210> SEQ ID NO 93
<211> LENGTH: 105
<212> TYPE: PRT
<213> ORGANISM: Artificial
<220> FEATURE:
<223> OTHER INFORMATION: NrdJ-1 N-intein

<400> SEQUENCE: 93

Cys Leu Val Gly Ser Ser Glu Ile Ile Thr Arg Asn Tyr Gly Lys Thr
1               5                   10                  15

Thr Ile Lys Glu Val Val Glu Ile Phe Asp Asn Asp Lys Asn Ile Gln
                20                  25                  30

Val Leu Ala Phe Asn Thr His Thr Asp Asn Ile Glu Trp Ala Pro Ile
            35                  40                  45

Lys Ala Ala Gln Leu Thr Arg Pro Asn Ala Glu Leu Val Glu Leu Glu
        50                  55                  60

Ile Asp Thr Leu His Gly Val Lys Thr Ile Arg Cys Thr Pro Asp His
65                  70                  75                  80

Pro Val Tyr Thr Lys Asn Arg Gly Tyr Val Arg Ala Asp Glu Leu Thr
                85                  90                  95

```
Asp Asp Asp Glu Leu Val Val Ala Ile
            100                 105

<210> SEQ ID NO 94
<211> LENGTH: 105
<212> TYPE: PRT
<213> ORGANISM: Artificial
<220> FEATURE:
<223> OTHER INFORMATION: NrdJ-2 N-intein

<400> SEQUENCE: 94

Cys Leu Val Gly Ser Ser Glu Ile Ile Thr Arg Asn Tyr Gly Lys Thr
1               5                   10                  15

Thr Ile Lys Glu Val Val Glu Ile Phe Asp Asn Asp Lys Asn Ile Gln
            20                  25                  30

Val Leu Ala Phe Asn Thr His Thr Asp Asn Ile Glu Trp Ala Pro Ile
        35                  40                  45

Lys Ala Ala Gln Leu Thr Arg Pro Asn Ala Glu Leu Val Glu Leu Glu
    50                  55                  60

Ile Asn Thr Leu His Gly Val Lys Thr Ile Arg Cys Thr Pro Asp His
65              70                  75                  80

Pro Val Tyr Thr Lys Asn Arg Asp Tyr Val Arg Ala Asp Glu Leu Thr
                85                  90                  95

Asp Asp Asp Glu Leu Val Val Ala Ile
            100                 105

<210> SEQ ID NO 95
<211> LENGTH: 38
<212> TYPE: PRT
<213> ORGANISM: Artificial
<220> FEATURE:
<223> OTHER INFORMATION: gp41-1 C-intein

<400> SEQUENCE: 95

Met Met Leu Lys Lys Ile Leu Lys Ile Glu Glu Leu Asp Glu Arg Glu
1               5                   10                  15

Leu Ile Asp Ile Glu Val Ser Gly Asn His Leu Phe Tyr Ala Asn Asp
            20                  25                  30

Ile Leu Thr His Asn Ser
        35

<210> SEQ ID NO 96
<211> LENGTH: 38
<212> TYPE: PRT
<213> ORGANISM: Artificial
<220> FEATURE:
<223> OTHER INFORMATION: gp41-2 C-intein

<400> SEQUENCE: 96

Met Met Leu Lys Lys Ile Leu Lys Ile Glu Glu Leu Asp Glu Arg Glu
1               5                   10                  15

Leu Ile Asp Ile Glu Val Ser Gly Asn His Leu Phe Tyr Ala Asn Ala
            20                  25                  30

Ile Leu Thr His Asn Ser
        35

<210> SEQ ID NO 97
<211> LENGTH: 26
<212> TYPE: PRT
<213> ORGANISM: Artificial
<220> FEATURE:
```

<223> OTHER INFORMATION: gp41-7 C-intein

<400> SEQUENCE: 97

Met Met Leu Lys Lys Ile Leu Lys Ile Glu Glu Leu Asp Glu Arg Glu
1               5                   10                  15

Leu Ile Asp Ile Glu Val Ser Gly Asn His
            20                  25

<210> SEQ ID NO 98
<211> LENGTH: 46
<212> TYPE: PRT
<213> ORGANISM: Artificial
<220> FEATURE:
<223> OTHER INFORMATION: gp41-8 C-intein

<400> SEQUENCE: 98

Met Cys Glu Ile Phe Glu Asn Glu Ile Asp Trp Asp Glu Ile Ala Ser
1               5                   10                  15

Ile Glu Tyr Val Gly Val Glu Glu Thr Ile Asp Ile Asn Val Thr Asn
            20                  25                  30

Asp Arg Leu Phe Phe Ala Asn Gly Ile Leu Thr His Asn Ser
        35                  40                  45

<210> SEQ ID NO 99
<211> LENGTH: 47
<212> TYPE: PRT
<213> ORGANISM: Artificial
<220> FEATURE:
<223> OTHER INFORMATION: gp41-9 C-intein

<400> SEQUENCE: 99

Met Ile Met Lys Asn Arg Glu Arg Phe Ile Thr Glu Lys Ile Leu Asn
1               5                   10                  15

Ile Glu Glu Ile Asp Asp Asp Leu Thr Val Asp Ile Gly Met Asp Asn
            20                  25                  30

Glu Asp His Tyr Phe Val Ala Asn Asp Ile Leu Thr His Asn Thr
        35                  40                  45

<210> SEQ ID NO 100
<211> LENGTH: 41
<212> TYPE: PRT
<213> ORGANISM: Artificial
<220> FEATURE:
<223> OTHER INFORMATION: IMPDH-1 C-intein

<400> SEQUENCE: 100

Met Lys Phe Lys Leu Lys Glu Ile Thr Ser Ile Glu Thr Lys His Tyr
1               5                   10                  15

Lys Gly Lys Val His Asp Leu Thr Val Asn Gln Asp Ser Tyr Asn
            20                  25                  30

Val Arg Gly Thr Val Val His Asn Ser
        35                  40

<210> SEQ ID NO 101
<211> LENGTH: 43
<212> TYPE: PRT
<213> ORGANISM: Artificial
<220> FEATURE:
<223> OTHER INFORMATION: IMPDH-2 C.intein

<400> SEQUENCE: 101

Met Lys Phe Thr Leu Glu Pro Ile Thr Lys Ile Asp Ser Tyr Glu Val
1               5                   10                  15

```
Thr Ala Glu Pro Val Tyr Asp Ile Glu Val Glu Asn Asp His Ser Phe
            20                  25                  30

Cys Val Glu Asn Gly Phe Val Val His Asn Ser
        35                  40

<210> SEQ ID NO 102
<211> LENGTH: 41
<212> TYPE: PRT
<213> ORGANISM: Artificial
<220> FEATURE:
<223> OTHER INFORMATION: IMPDH-3 C-intein

<400> SEQUENCE: 102

Met Lys Phe Lys Leu Val Glu Ile Thr Ser Lys Glu Thr Phe Asn Tyr
1               5                   10                  15

Ser Gly Gln Val His Asp Leu Thr Val Glu Asp His Ser Tyr Ser
            20                  25                  30

Ile Asn Asn Ile Val Val His Asn Ser
        35                  40

<210> SEQ ID NO 103
<211> LENGTH: 35
<212> TYPE: PRT
<213> ORGANISM: Artificial
<220> FEATURE:
<223> OTHER INFORMATION: NrdA-2 C-intein

<400> SEQUENCE: 103

Met Gly Leu Lys Ile Ile Lys Arg Glu Ser Lys Glu Pro Val Phe Asp
1               5                   10                  15

Ile Thr Val Lys Asp Asn Ser Asn Phe Phe Ala Asn Asn Ile Leu Val
            20                  25                  30

His Asn Cys
        35

<210> SEQ ID NO 104
<211> LENGTH: 34
<212> TYPE: PRT
<213> ORGANISM: Artificial
<220> FEATURE:
<223> OTHER INFORMATION: NrdA-3

<400> SEQUENCE: 104

Met Leu Lys Ile Glu Tyr Leu Glu Glu Ile Pro Val Tyr Asp Ile
1               5                   10                  15

Thr Val Glu Glu Thr His Asn Phe Phe Ala Asn Asp Ile Leu Ile His
            20                  25                  30

Asn Cys

<210> SEQ ID NO 105
<211> LENGTH: 28
<212> TYPE: PRT
<213> ORGANISM: Artificial
<220> FEATURE:
<223> OTHER INFORMATION: NrdA-5 C-intein

<400> SEQUENCE: 105

Met Leu Lys Ile Glu Tyr Leu Glu Glu Ile Pro Val Tyr Asp Ile
1               5                   10                  15

Thr Val Glu Gly Thr His Asn Leu Ala Tyr Ser Leu
            20                  25
```

```
<210> SEQ ID NO 106
<211> LENGTH: 33
<212> TYPE: PRT
<213> ORGANISM: Artificial
<220> FEATURE:
<223> OTHER INFORMATION: NrdA-6 C-intein

<400> SEQUENCE: 106

Met Gly Ile Lys Ile Arg Lys Leu Glu Gln Asn Arg Val Tyr Asp Ile
1               5                   10                  15

Lys Val Glu Lys Ile Ile Ile Phe Cys Asn Asn Ile Leu Val His Asn
            20                  25                  30

Cys

<210> SEQ ID NO 107
<211> LENGTH: 34
<212> TYPE: PRT
<213> ORGANISM: Artificial
<220> FEATURE:
<223> OTHER INFORMATION: NrdA-7 C-intein

<400> SEQUENCE: 107

Met Leu Lys Ile Glu Tyr Leu Glu Glu Ile Pro Val Tyr Asp Ile
1               5                   10                  15

Thr Val Glu Lys Thr Asn Asn Phe Phe Ala Asn Asp Ile Leu Val His
            20                  25                  30

Asn Cys

<210> SEQ ID NO 108
<211> LENGTH: 41
<212> TYPE: PRT
<213> ORGANISM: Artificial
<220> FEATURE:
<223> OTHER INFORMATION: NrdJ-1 C-intein

<400> SEQUENCE: 108

Met Glu Ala Lys Thr Tyr Ile Gly Lys Leu Lys Ser Arg Lys Ile Val
1               5                   10                  15

Ser Asn Glu Asp Thr Tyr Asp Ile Gln Thr Ser Thr His Asn Phe Phe
            20                  25                  30

Ala Asn Asp Ile Leu Val His Asn Ser
            35                  40
```

SPLIT INTEINS AND USES THEREOF

CROSS-REFERENCE TO RELATED APPLICATIONS

This application is filed under the provisions of 35 U.S.C. § 371 and claims the priority of International Patent Application No. PCT/EP2012/069219 filed on 28 Sep. 2012 entitled "SPLIT INTEINS AND USES THEREOF" in the name of Roser PALLISSE BERGWERF, et al., which claims priority to European Patent Application No. 12171848.0 filed on 13 Jun. 2012 and U.S. Provisional Patent Application No. 61/540,101 filed on 28 Sep. 2011, all of which are hereby incorporated by reference herein in their entirety.

FIELD OF THE INVENTION

The present invention relates generally to robust split inteins and uses thereof, for example, in protein purification and engineering.

BACKGROUND

Inteins are internal protein elements that self-excise from their host protein and catalyze ligation of the flanking sequences (exteins) with a peptide bond. Intein excision is a posttranslational process that does not require auxiliary enzymes or cofactors. This self-excision process is called "protein splicing," by analogy to the splicing of RNA introns from pre-mRNA (Perler F et al., *Nucl Acids Res.* 22:1125-1127 (1994)). The segments are called "intein" for internal protein sequence, and "extein" for external protein sequence, with upstream exteins termed "N-exteins" and downstream exteins called "C-exteins." The products of the protein splicing process are two stable proteins: the mature protein and the intein.

Structure of Mini-inteins and Large Inteins

Inteins are classified into two groups: large and minimal (mini) (Liu XQ, *Ann Rev Genet* 34:61-76 (2000)). Large inteins contain a homing endonuclease domain that is absent in mini-inteins. Splicing-efficient mini-inteins have been engineered from large inteins by deleting the central endonuclease domain, demonstrating that the endonuclease domain is not involved in protein splicing (Chong S. and Xu M., *J Biol Chem.* 272:15587-15589 (1997); Derbyshire V. et al., *Proc Natl Acad Sci USA.* 94:11466-11471 (1997); and Shingledecker K. et al. *Gene.* 207:187-195 (1998)).

All known inteins share a low degree of sequence similarity, with conserved residues only at the N- and C-termini. Most inteins begin with Ser or Cys and end in His-Asn or in His-Gln. The first amino acid of the C-extein is an invariant Ser, Thr, or Cys, but the residue preceding the intein at the N-extein is not conserved (Perler F. 2002, Nucl. Acids Res. 30: 383-384). However, residues proximal to the intein-splicing junction at both the N- and C-terminal exteins were recently found to accelerate or attenuate protein splicing (Amitai G et al. 2009, Proc. Natl. Acad. Sci. USA. 106: 11005-11010).

Cis- and Trans-splicing Mechanisms of Inteins

The inteins can be classified by their splicing mechanism. Class 1 inteins, which are the most studied group of inteins, have a rapid process of four nucleophilic attacks, mediated by three of the four conserved splice junction residues. In step 1, the splicing process begins with an acyl-shift of the serine or cysteine residue located at the first position of the N-terminal splicing domain. This forms a (thio)ester bond at the N-extein/intein junction. In step 2, the (thio)ester bond is attacked by the OH- or SH-group of the first residue in the C-extein (Cys, Ser, or Thr). This leads to a transesterification, which transfers the N-extein to the side-chain of the first residue of the C-extein. In step 3, the cyclization of the conserved Asn or Gln residue located at the last position of the C-terminal splicing domain links the exteins by a (thio) ester bond. Finally, step 4 is a rearrangement of the (thio) ester bond to a peptide bond by a spontaneous S—N or O—N acyl shift. The important amino acids involved directly or indirectly in the splicing reaction are shown in FIG. 3A.

Site-specific cleavage of the inteinextein junctions in class 1 inteins can be achieved by mutation of the conserved intein residues. Mutation of the Asn or Gln residue at the intein C-terminus abolishes steps 3 and 4 of the splicing reaction and results in N-terminal cleavage only. Since step 1 still occurs, the (thio)ester bond can spontaneously hydrolyze, separating the N-extein from the intein/C-extein portion. The serine or cysteine residue located at the first position of the N-terminal splicing domain is required for N-terminal cleavage (see FIG. 3C). Mutation of this conserved first residue of the intein abolishes steps 1, 2, and 4 of the splicing reaction and leads to C-terminal cleavage only. In such a mutated intein, Asn cyclization (step 3) still occurs, to separate the C-extein from the N-extein/intein portion. The Asn (or Gln), and the His residues located respectively at the last ($X_N$) and penultimate ($x_{N-1}$) positions of the C-terminal splicing domain are required for N-terminal cleavage (see FIG. 3B). Controllable cleavage of modified cis-splicing inteins has been adapted for a wide range of useful applications in molecular biology and biotechnology.

Natural Split Inteins

Inteins can also exist as two fragments encoded by two separately transcribed and translated genes. These so-called split inteins self-associate and catalyze protein-splicing activity in trans.

Split inteins have been identified in diverse cyanobacteria and archaea (Caspi et al., *Mol Microbiol.* 50:1569-1577 (2003); Choi J. et al., *J Mol Biol.* 356:1093-1106 (2006.); Dassa B. et al., *Biochemistry.* 46:322-330 (2007.); Liu X. and Yang J., *J Biol Chem.* 278:26315-26318 (2003); Wu H. et al., *Proc Natl Acad Sci USA.* 95:9226-9231 (1998.); and Zettler J. et al., *FEBS Letters.* 583:909-914 (2009)), but have not been found in eukaryotes thus far. Recently, a bioinformatic analysis of environmental metagenomic data revealed 26 different loci with a novel genomic arrangement. At each locus, a conserved enzyme coding region is interrupted by a split intein, with a free-standing endonuclease gene inserted between the sections coding for intein subdomains. Among them, five loci were completely assembled: DNA helicases (gp41-1, gp41-8); Inosine-5'-monophosphate dehydrogenase (IMPDH-1); and Ribonucleotide reductase catalytic subunits (NrdA-2 and NrdJ-1). This fractured gene organization appears to be present mainly in phages (Dassa et al. *Nucleic Acids Research.* 37:2560-2573 (2009)).

The split intein Npu DnaE was characterized as having the highest rate reported for the protein trans-splicing reaction. In addition, the Npu DnaE protein splicing reaction is considered robust and high-yielding with respect to different extein sequences, temperatures from 6 to 37° C., and the presence of up to 6 M Urea (Zettler J. et al., *FEBS Letters.* 583:909-914 (2009); Iwai I. et al., *FEBS Letters* 580:1853-1858 (2006)). As expected, when the Cys1 Ala mutation at the N-domain of these inteins was introduced, the initial N to S-acyl shift and therefore protein splicing was blocked. Unfortunately, the C-terminal cleavage reaction was also almost completely inhibited. The dependence of the asparagine cyclization at the C-terminal splice junction on the acyl shift at the N-terminal scissile peptide bond seems to be a unique property common to the naturally split DnaE intein alleles (Zettler J. et al. *FEBS Letters.* 583:909-914 (2009)).

Applications of Inteins in Biotechnology

Inteins are valuable tools in a wide range of biotechnological applications The ligation of peptides and proteins using the natural splicing activity of inteins is known as intein-mediated protein ligation (IPL), or expressed protein ligation (EPL), and is well established in molecular biology and biotechnology methods (Evans T. et al., *Biopolymers* 51:333-342 (1999); Muir T. et al., *Proc Natl Acad Sci USA.* 95:6705-6710 (1998); and Severinov K. and Muir T., *J Biol Chem.* 273:16205-16209 (1998)). Furthermore, inteins have been used for protein purification by site-specific cleavage only at the intein-target protein border (Lu W. et al, *J Chromatography A.* 1218:2553-2560 (2011)). The use of intein-mediated procedures in bioseparation is well established at the laboratory scale and is attracting increasing interest in large-scale biotechnology. The potential of these protein purification techniques for large-scale protein production is clear, but intein-mediated protein purification systems under industrial, scaled-up conditions must be developed. Other applications are segmental labeling of proteins for NMR analysis, cyclization of proteins, controlled expression of toxic proteins, conjugation of quantum dots to proteins and incorporation of non-canonical amino acids, (Arnold U., *Biotechnol Lett.* 31:1129-1139 (2009); Charalambous A. et al., *J Nanobiotechnology* 7:9 (2009); Oeemig J. et al., *FEBS Letters* 583:1451-1456 (2009); Seyedsayamdost M. et al., *Nat Protoc.* 2:1225-1235 (2007); Züger S. and Iwai H., *Nat Biotechnol.* 23:736-740 (2005); and Evans T. et al., *Annu Rev Plant Biol.* 56:375-392 (2005)). In basic research studies, inteins have been used to monitor in vivo protein—protein interactions, specifically translocation of proteins into cellular organelles, ligation of exogenous polypeptide to membrane proteins on living cells or photocontrol of protein activity (Chong S. and Xu M., *Homing endonucleases and inteins. Vol 16.* Springer, Berlin Heidelberg, New York, 273-292 (2005); Ozawa T. and Umezawa Y., Homing endonucleases and inteins. Vol 16. Springer, Berlin Heidelberg, New York, 307-323 (2005); Ozawa T. et al., *Nat Biotechnol.* 21:287-293 (2003); Dhar T. and Mootz H., *Chem Commun.* 47:3063-3065 (2011); and Binschik J. et al., Angewandte Chemie International Ed. 50(14):3249-3252 (2011)). Most of the inteins used in biotechnology are derived from prokaryotic organisms, or are engineered variants of the *S. cerevisiae* VMA1 -intein (Elleuche & Pöggeler 2010 Appl. Microbiol Biotechnol 78:479-489).

In order to make use of such techniques in large-scale biological processes, inteins with robust properties and methods of using the same must be identified. The inteins and methods of using such inteins that are described herein address this need by providing highly active inteins that function in a large temperature range, in the presence of salts, and when fused to polypeptides of variable sequences.

BRIEF SUMMARY OF THE INVENTION

The present invention provides robust split inteins and methods of using the same. The split inteins are active over a large temperature range, over a wide pH range, and in the presence of chaotropic salts. They also show high tolerance to sequence variability in fused heterologous polypeptides. These features make the split inteins especially useful in protein purification and engineering techniques.

In particular, fusion proteins comprising (i) an intein domain at least 75% identical to a sequence selected from the group consisting of SEQ ID NOs: 7, 16, 24, 38 and 65 and (ii) a heterologous polypeptide, wherein the heterologous polypeptide is C-terminal to the intein domain are provided. In some embodiments, the last amino acid of the intein domain is asparagine or glutamine. In some embodiments, the last amino acid of the intein domain is an amino acid other than asparagine or glutamine, e.g., an alanine In some embodiments, the penultimate amino acid of the intein domain is an amino acid other than histidine. In some embodiments, the heterologous polypeptide is directly linked to the intein domain via a peptide bond. In some embodiments, the first amino acid of the heterologous polypeptide is serine, cysteine, or threonine. In some embodiments, the last amino acid of the intein domain is an amino acid other than asparagine or glutamine, e.g., an alanine and the first amino acid of the heterologous polypeptide is other than serine, threonine or cysteine, e.g. alanine In some embodiments, the fusion protein further comprises a linker between the heterologous polypeptide and the intein domain. In some embodiments, the first amino acid of the linker is serine, cysteine, or threonine. In some embodiments, the first amino acid of the linker is an amino acid other than serine, cysteine, or threonine, i.e an alanine In some embodiments, the last amino acid of the intein domain is an amino acid other than asparagine or glutamine, e.g., an alanine and the first amino acid of the linker is an amino acid other than serine, threonine or cysteine. e.g an alanine In some embodiments, the linker comprises 1-5 amino acids of a native extein sequence. Fusion proteins comprising an intein domain having a sequence selected from the group consisting of SEQ ID NOs: 7, 16, 24, 38 and 65 and (ii) a heterologous polypeptide, wherein the heterologous polypeptide is C-terminal to the intein domain are also provided.

In addition, fusion proteins comprising (i) an intein domain at least 75% identical to a sequence selected from the group consisting of SEQ ID NOs: 3, 12, 20, 34 and 64 and (ii) a heterologous polypeptide, wherein the heterologous polypeptide is N-terminal to the intein domain are provided. In some embodiments, the first amino acid of the intein domain is a cysteine. In some embodiments, the first amino acid of the intein domain is an amino acid other than serine or cysteine, e.g., an alanine In some embodiments, the heterologous polypeptide is directly linked to the intein domain via a peptide bond. In some embodiments, the fusion protein further comprises a linker between the heterologous polypeptide and the intein domain. In some embodiments, the linker comprises 1-5 amino acids of a native extein sequence. Fusion proteins comprising an intein domain having a sequence selected from the group consisting of SEQ ID NOs: 3, 12, 20, 34 and 64 and a heterologous polypeptide, wherein the heterologous polypeptide is N-terminal to the intein domain are also provided.

Furthermore, fusion proteins comprising a first intein domain, a second intein domain, and a heterologous polypeptide are provided. Furthermore, fusion proteins comprising a first intein domain, a second intein domain, and a heterologous polypeptide are provided wherein the heterologous polypeptide is N-terminal to the first intein domain, and the heterologous polypeptide is C-terminal to the second intein domain. Furthermore, fusion proteins comprising a first intein domain, a second intein domain, and a heterologous polypeptide are provided wherein the heterologous polypeptide is N-terminal to the first intein domain (N-terminal splicing domain), and the heterologous polypeptide is C-terminal to the second intein domain (C-terminal splicing domain). In some embodiments, (a) the first intein domain is at least 75% identical to SEQ ID NO:3 and the second intein domain is at least 75% identical to SEQ ID NO:7; (b) the first intein domain is at least 75% identical to SEQ ID NO:12 and the second intein domain is at least 75% identical to SEQ ID NO:16; (c) the first intein domain is at least 75% identical to SEQ ID NO:20 and the second intein domain is at least 75% identical to SEQ ID NO:24; (d) the first intein domain is at least 75% identical to SEQ ID NO:34 and the second intein domain is at least 75% identical to SEQ ID NO:38; or (d) the first intein domain is at least 75% identical to SEQ ID NO:64 and the second intein domain is at least 75% identical to SEQ ID NO:65. In some embodiments, the first amino acid of the heterologous polypeptide is serine, cysteine, or threonine. In some embodiments, the fusion protein further comprises a linker between the heterologous polypeptide and the second intein domain, wherein the first amino acid of the linker is serine, cysteine, or threonine. In some embodiments, the first amino acid of the linker is serine.

Polynucleotides encoding the fusion proteins according to the invention are also provided herein.

Compositions comprising fusion proteins are also provided. Such compositions are useful, for example, for C-terminal cleavage reactions, N-terminal cleavage reactions, trans-splicing reactions, and protein-cyclization methods.

Host cells comprising the proteins, fusion proteins, polynucleotides, or compositions are also provided.

Methods of using polypeptides and fusion proteins provided herein in, for example, C-terminal cleavage reactions, N-terminal cleavage reactions, trans-splicing reactions, and protein-cyclization are provided. Such methods can occur at temperatures of about 0° C. to about 60° C. at a pH of about 6 to about 10, and/or in the presence of about 0.5 M to about 6 M urea.

In some embodiments, the reaction rate constant of the reactions provided herein is at least about $1 \times 10^{-1}$ s$^{-1}$, or at least about $2 \times 10^{-1}$ s$^{-1}$. In some embodiments, the reaction rate half-life is less than about 100 seconds, less than about 50 seconds, or less than about 25 seconds or less than about 15 seconds.

The reactions can be initiated, for example, by a shift in temperature or pH or mixing proteins.

The invention also provides a vector which comprises a polynucleotide encoding an intein domain at least 75% identical to a sequence selected from the group consisting of SEQ ID NOs: 7, 16, 24, 38 and 65 and at least a cloning site downstream of said polynucleotide which allows the cloning of a polynucleotide of interest such that a polynucleotide is formed which encodes a fusion protein comprising the intein domain and the polypeptide encoded by the polynucleotide of interest.

The invention also provides a vector which comprises a polynucleotide encoding an intein domain at least 75% identical to a sequence selected from the group consisting of SEQ ID NOs: 3, 12, 20, 34 and 64 and at least a cloning site upstream of said polynucleotide which allows the cloning of a polynucleotide of interest such that a polynucleotide is formed which encodes a fusion protein comprising the polypeptide encoded by the polynucleotide of interest and the intein domain.

The invention also provides a vector which comprises a polynucleotide encoding an intein domain at least 75% identical to a sequence selected from the group consisting of SEQ ID NOs: 7, 16, 24, 38 and 65, at least a cloning site downstream of said polynucleotide which allows the cloning of a polynucleotide of interest, and a polynucleotide downstream of the cloning site, encoding an intein domain at least 75% identical to a sequence selected from the group consisting of SEQ ID NOs: 3, 12, 20, 34 and 64, such that a polynucleotide is formed which encodes a fusion protein comprising the polypeptide encoded by the polynucleotide of interest and the two intein domains wherein a. if the first intein domain is at least 75% identical to SEQ ID NO:7, then the second intein domain is at least 75% identical to SEQ ID NO:3;
b. if the first intein domain is at least 75% identical to SEQ ID NO:16 then the second intein domain is at least 75% identical to SEQ ID NO:12;
c. if the first intein domain is at least 75% identical to SEQ ID NO:24, then the second intein domain is at least 75% identical to SEQ ID NO:20;
d. if the first intein domain is at least 75% identical to SEQ ID NO:38, then the second intein domain is at least 75% identical to SEQ ID NO:34.

The invention also provides a vector which comprises a polynucleotide encoding a first intein domain at least 75% identical to a sequence selected from the group consisting of SEQ ID NOs: 7, 16, 24, 38 and 65, a first cloning site downstream of said polynucleotide encoding a first intein domain, a polynucleotide encoding a second intein domain at least 75% identical to a sequence selected from the group consisting of SEQ ID NOs: 3, 12, 20, 34 and 64 and a second cloning site upstream of said polynucleotide encoding a second intein domain, wherein the first cloning site allows the cloning of a first polynucleotide of interest and the second cloning site allows the cloning of a second polynucleotide of interest such that a polynucleotide is formed which encodes a fusion protein comprising, in said order, the polypeptide encoded by the second polynucleotide of interest, the second intein domain, the first intein domain and the polypeptide encoded by the second polynucleotide of interest and wherein a. if the first intein domain is at least 75% identical to SEQ ID NO:7, then the second intein domain is at least 75% identical to SEQ ID NO:3;
b. if the first intein domain is at least 75% identical to SEQ ID NO:16 then the second intein domain is at least 75% identical to SEQ ID NO:12;
c. if the first intein domain is at least 75% identical to SEQ ID NO:24, then the second intein domain is at least 75% identical to SEQ ID NO:20;
d. if the first intein domain is at least 75% identical to SEQ ID NO:38, then the second intein domain is at least 75% identical to SEQ ID NO:34 or
e. if the first intein domain is at least 75% identical to SEQ ID NO:65, then the second intein domain is at least 75% identical to SEQ ID NO:64.

BRIEF DESCRIPTION OF THE DRAWINGS/FIGURES

FIG. 1. (A) Schematic representation of a trans-splicing reaction. The initial N-terminus fragment (F1) and the C-terminus fragment (F2) of the split intein are shown at the top. The regions that will be joined after the trans-splicing reaction are indicated in grey. The 3 fragments resulting from the trans-splicing reaction are shown at the bottom. F3 represents the spliced product (in grey), and F4 and F5 correspond to the N- and C-split intein side-products, respectively. StreptagII purification tag (ST), phage protein bacteriophage λ head protein D (gpD), the five natural flanking amino acids belonging to the N-terminus extein ($E^N$), the N-terminus split intein ($I^N$), the hexa-histidine purification tag (H6), C-terminus split intein ($I^C$), the five natural flanking amino acids belonging to the C-terminus extein ($E^C$), Thioredoxin (Trx), and the junction of the N- and C-terminus exteins ($E^{NC}$). (B) Time course of the trans-splicing reaction of the Gp41.1 (G1) split intein analyzed by Coomassie blue staining of SDS-PAGE gel. The initial N- and C-terminus fragments (F1 and F2, respectively) are shown in lane 1. The trans-splicing reaction after incubation at 25° C. for 10 s, 20 s, 30 s, 1 min, 5 min, 30 min, 1 h and 2 h are shown in lanes 2-9. The position of F1, F2, F3, F4 and F5 are indicated by arrows.

Figure 2:
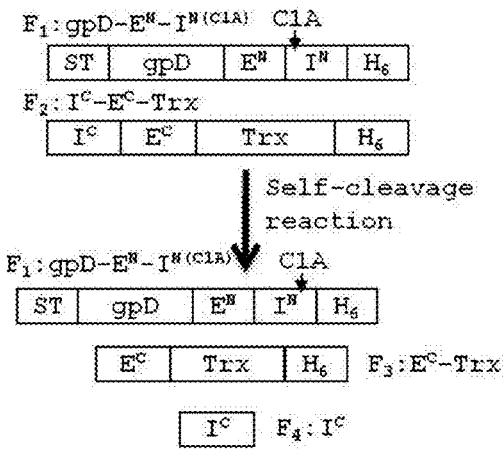
Figure 2:
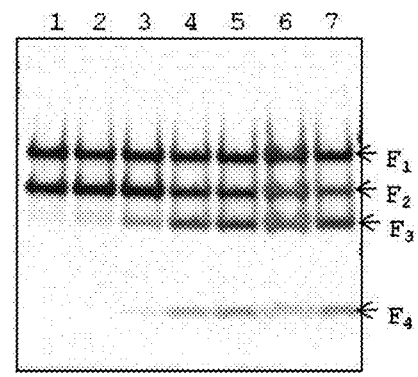
Figure 2:
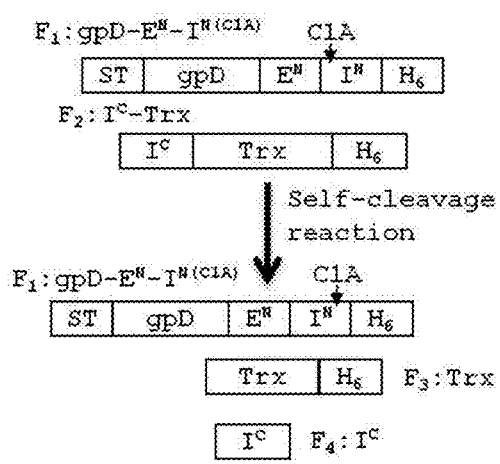
Figure 2:
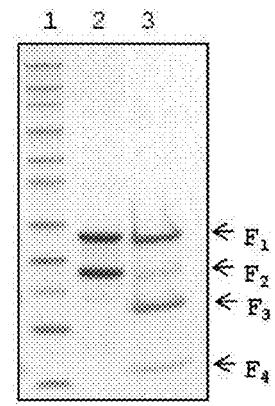

FIG. 2. (A) C-terminal self-cleavage reaction of the Gp41.1 (G1) split intein. The first amino acid (cysteine) from the N-terminus intein has been substituted with an alanine (C1A). The schematic representation of a general self-cleavage reaction is shown on the left. The incubation of the mutated N-terminus fragment (F1) and the C-terminus fragment (F2) of the split intein results in the cleavage of F2 to generate the desired Trx containing fragment (F3) and the C-terminus split intein side-product (F4). The fragment liberated in the self-cleavage reaction is indicated in grey. A time course of the self-cleavage reaction of the Gp41.1 (G1) split intein analyzed by Coomassie blue staining of SDS-PAGE gel is shown on the right. The initial N- and C-terminus fragments (F1 and F2, respectively) are shown in lane 1. The self-cleavage reaction after incubation at 37° C. for 1 min, 5 min, 35 min, 1 h, 2 h and 4 h, are shown in lanes 2 to 7. The position of F1, F2, F3, and F4 are indicated by arrows. (B) C-terminal self-cleavage reaction of the Gp41.1 (G1) split intein. The schematic representation of a general self-cleavage reaction when the N-terminus intein contains the C1A substitution and the 5 natural amino acids corresponding to the EC are missing from F2 is shown on the left. A self-cleavage reaction of the Gp41.1 (G1) split intein analyzed by Coomassie blue staining of SDS-PAGE gel is shown on the right. The initial N- and C-terminus fragments (F1 and F2, respectively) are shown in lane 2. Lane 3 shows the self-cleavage reaction after incubation at 37° C. for 23 h. The position of F1, F2, F3, and F4 are indicated by arrows. StreptagII purification tag (ST), phage protein bacteriophage λ head protein D (gpD), the five natural flanking amino acids belonging to the N-terminus extein ($E^N$), the N-terminus split intein ($I^N$), the hexa-histidine purification tag (H6), C-terminus split intein ($I^C$), the five natural flanking amino acids belonging to the C-terminus extein ($E^C$) and thioredoxin (Trx)

Figure 3:
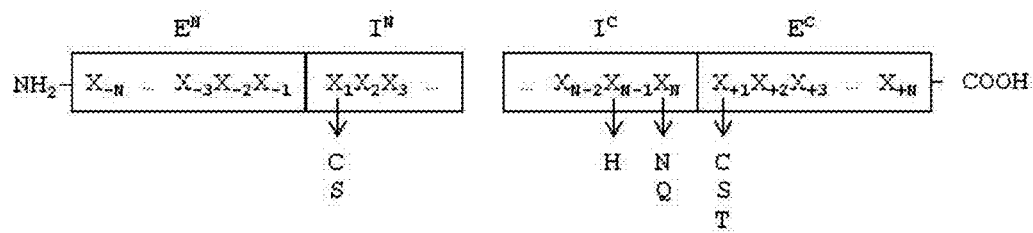
Figure 3:
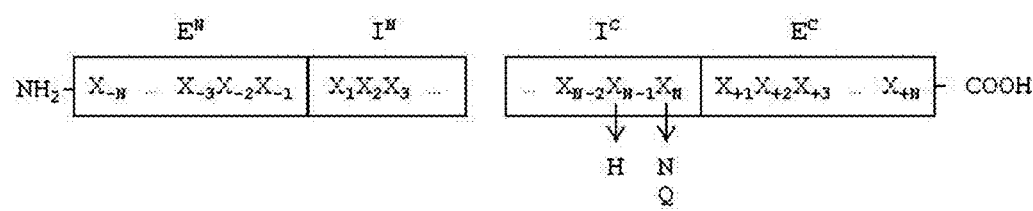
Figure 3:
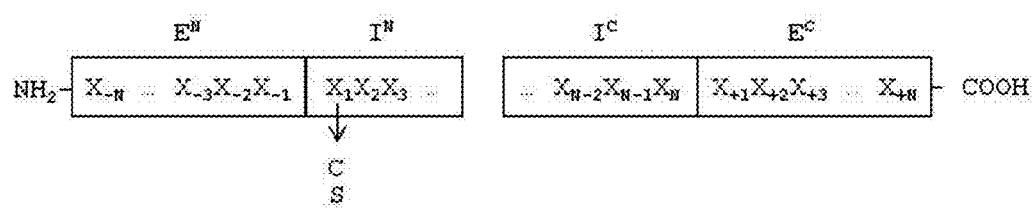

FIG. 3. Schematic representation showing (A) trans-splicing, (B) C-terminal self-cleavage, and (C) N-terminal self-cleavage constructs. Natural flanking amino acids belonging to the N-terminus extein ($E^N$), the N-terminus split intein ($I^N$), C-terminus split intein ($I^C$), natural flanking amino acids belonging to the C-terminus extein ($E^C$). The key amino acids involved directly or indirectly in the corresponding reaction are indicated.

DETAILED DESCRIPTION OF THE INVENTION

The following provides a description of split inteins that are useful in a number of protein-engineering applications. The split inteins contain Gp41.1, Gp41.8, NrdA2, NrdJ1 or IMPDH1 sequences fused to heterologous proteins and can be used, for example, in protein synthesis, cleavage, purification, ligation, cyclization, and regulation and/or monitoring of protein activity.

The section headings used herein are for organizational purposes only and are not to be construed as in any way limiting the subject matter described.

I. Definitions

Unless otherwise expressly defined, the terms used herein are to be understood according to their ordinary meaning in the art. Terms used in the singular or referred to as "a" or "an" also include the plural and vice versa, unless otherwise specified or indicated by context. Standard techniques and procedures are generally performed according to conventional methods in the art and various general references (see generally, Sambrook et al. Molecular Cloning: A Laboratory Manual, 2nd ed. (1989) Cold Spring Harbor Laboratory Press, Cold Spring Harbor, N.Y., which is incorporated herein by reference), which are provided throughout this document.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

A "fusion polypeptide" is a polypeptide comprised of at least two polypeptides and optionally a linking sequence to operatively link the two polypeptides into one continuous polypeptide. The two polypeptides linked in a fusion polypeptide are typically derived from two independent sources, and therefore a fusion polypeptide comprises two linked polypeptides not normally found linked in nature. The two polypeptides may be operably attached directly by a peptide bond or may be linked indirectly through a linker described herein or otherwise known in the art.

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, *Proc. Natl. Acad. Sci.*, 87:2264-2268, as modified in Karlin et al., 1993, *Proc. Natl. Acad. Sci.*, 90:5873-5877, and incorporated into the NBLAST and XBLAST programs (Altschul et al., 1991, *Nucleic Acids Res.*, 25:3389-3402). In certain embodiments, Gapped BLAST can be used as described in Altschul et al., 1997, *Nucleic Acids Res.* 25:3389-3402. BLAST-2, WU- BLAST-2 (Altschul et al., 1996, *Methods in Enzymology*, 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* 48:444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the second sequence is longer than the first sequence, then the percent identity may be determined only in the region of overlap between said first and second sequences. In this case, the same formula as above can be used but using as Z value the length of the region wherein the first and second sequence overlaps, said region having a length which is substantially the same as the length of the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wisc. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value therebetween, and can be over a longer region than 60-80 residues, for example, at least about 90-100 residues, and in some embodiments, the sequences are substantially identical over the full length of the sequences being compared, such as the coding region of a nucleotide sequence for example.

The term "vector" means a construct, which is capable of delivering, and optionally expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells. The vectors can be stable and can be self-replicating. An "expression vector" is a vector that is capable of directing the expression of genes to which it is operably associated.

"Promoter" refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

The term "heterologous" as used herein refers to an element of a vector, plasmid or host cell that is derived from a source other than the endogenous source. Thus, for example, a heterologous sequence (e.g., a polynucleotide sequence or a polypeptide sequence) could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region. "Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The terms "operably associated" and "operably linked" refer to the association of two molecules so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation. Two molecules are "operably linked" whether they are attached directly (e.g., a fusion protein) or indirectly (e.g., via a linker).

As used herein, the term "expression" refers to the transcription of RNA (e.g., mRNA) from a nucleic acid template and/or the translation of mRNA into a polypeptide. The term "increased expression" is intended to include an alteration in gene expression at the level of increased mRNA production and/or at the level of polypeptide expression, generally resulting in an increased amount of a gene product or protein. In some instances, "increased expression" is used interchangeably with the term "overexpression" or "overexpressed."

II. Inteins

An intein is a protein element that is capable of self-excising from a host protein and catalyzing ligation of the flanking sequences with a peptide bond. A split intein is any intein in which the N-terminal domain of the intein and the C-terminal domain of the intein are not directly linked via a peptide bond. Natural split inteins have been identified in cyanobacteria and archaea, but split inteins can also be created artificially by separating an intein's sequence into two pieces. The split inteins described herein provide advantages over known split inteins in that they function over a large temperature range and in the presence of salts. They also splice at rates that are faster than other known split inteins. In addition, the split inteins described herein are tolerant to sequence variation both within the intein and within extein and/or heterologous polypeptide sequences. The split inteins described herein provide advantages over known split inteins in that they can perform C-terminal self-cleavage independently of the first amino acid of the C-Extein.

The split inteins used herein can comprise the six conserved protein-splicing motifs of the HINT (Hog/Intein) family. The sequences of such conserved motifs can be used to predict which amino acids in an intein domain are more strictly conserved and which amino acids are less strictly conserved. Mutations of more strictly conserved amino acids can reduce the efficacy of intein cleavage.

An "intein N-terminal domain" refers to an intein sequence that comprises an N-terminal amino acid sequence that is functional for trans-splicing reactions and/or N-terminal self-cleavage reactions. An intein N-terminal domain can be spliced out when trans-splicing occurs. Suitable assays for determining whether an intein sequence is an N-terminal domain can be found in example 1 of the present invention, which provides an assay for measuring the trans-splicing activity or in example 6, which provides an assay for detecting N-terminal self-cleavage.

The intein N-terminal domain can comprise one or more of N1, N2, N3, and/or N4 motifs of the HINT (Hog/Intein) family. Thus, for example, an intein N-terminal domain can comprise the N1 and N3 motifs.

In some embodiments, the intein N-terminal domain comprises an N1 box (A box) sequence. The N1 box is a non-strictly conserved sequence. The N1 box can comprise, for example, the sequence ChsXcplhXTXXG (SEQ ID NO:44), wherein h is a hydrophobic amino acid, s is a small amino acid, c is a charged amino acid, p is a polar amino acid, and l is a large amino acid. In some embodiments, the intein N-terminal domain comprises the sequence $X_1X_2X_3X_4X_5X_6X_7X_8X_9X_{10}X_{11}X_{12}X_{13}$ (SEQ ID NO:45), wherein $X_1$ is C; $X_2$ is L, F, or V; $X_3$ is S, T, V, or A; $X_4$ is L, P, G, or Y; $X_5$ is D, E, K, or G; $X_6$ is T or A; $X_7$ is E, Q, L, M, K, or T; $X_8$ is I or V; $X_9$ is L, Q, V, N, K, D, or T; $X_{10}$ is T, I, or V; $X_{11}$ is V, P, Q, N, E, K, or L; $X_{12}$ is E, Q, G, N, Y, I, or E; and $X_{13}$ is Y, G, K, P, or D. In some embodiments, the intein N-terminal domain comprises the sequence $X_1X_2X_3X_4X_5X_6X_7X_8X_9X_{10}X_{11}X_{12})_{(13}$ (SEQ ID NO:46), wherein $X_1$ is C; $X_2$ is L, F, or V; $X_3$ is S, T, V, or A; $X_4$ is L, P, or G; $X_5$ is D, K, or G; $X_6$ is T or A; $X_7$ is Q, L, M, K, or T; $X_8$ is I or V; $X_9$ is Q, V, N, K, D, or T; $X_{10}$ is T, I, or V; $X_{11}$ is P, Q, N, E, K, or L; $X_{12}$ is E, Q, G, N, Y, I, or E, and $X_{13}$ is G, K, P, or D.

Based on chemical properties of the amino acids, they can be grouped as: (i) charged (D, E, K, R, H), (ii) acidic (D, E), (iii) basic (K, R, H), (iv) small (V, C, S, T, P, G, D, A), (v) polar (N,Q, S, T), (vi) large (E, Q, R, K, H, Y, W, F, M, L, I), (vii) hydrophobic (V, I, L, M, F, Y, W, A) and (viii) Nucleophilic (S, T, C).

In some embodiments, the intein N-terminal domain N1-Box comprises a sequence that is at least about 75%, at least about 80%, at least about 85%, at least about 90%, at least about 95%, or at least about 99% identical to a sequence corresponding to amino acids 1 to 13 of SEQ ID NO:3.

In some embodiments, an intein N-terminal domain N1-Box comprises a sequence that is at least about 30%, at least about 35%, at least about 40%, at least about 45%, is at least about 50%, at least about 55%, at least about 60%, at least about 70%, at least about 75%, at least about 80%, at least about 85%, at least about 90%, at least about 95%, or at least about 99% identical to a sequence corresponding to amino acids 1 to 13 of SEQ ID NO:12.

In some embodiments, an intein C-terminal domain N1-Box comprises a sequence that is at least about 40%, at least about 45%, is at least about 50%, at least about 55%, at least about 60%, at least about 70%, at least about 75%, at least about 80%, at least about 85%, at least about 90%, at least about 95%, or at least about 99% identical to a sequence corresponding to amino acids 1 to 13 of SEQ ID NO:34.

In some embodiments, the intein N-terminal domain N1-Box comprises a sequence that is at least about 30%, at least about 35%, at least about 40%, at least about 45%, is at least about 50%, at least about 55%, at least about 60%, at least about 70%, at least about 75%, at least about 80%, at least about 85%, at least about 90%, at least about 95%, or at least about 99% identical to a sequence corresponding to amino acids 1 to 13 of SEQ ID NO:64.

In some embodiments, an intein N-terminal domain N1-Box comprises a sequence that is at least about 50%, at least about 55%, at least about 60%, at least about 70%, at least about 75%, at least about 80%, at least about 85%, at least about 90%, at least about 95%, or at least about 99% identical to a sequence corresponding to amino acids 1 to 13 of SEQ ID NO:20.

In some embodiments, the intein N-terminal domain comprises an N3 box (B box) sequence. The N3 box is a non-strictly conserved sequence. The N3 box can comprise, for example, the sequence GXXhXhTXaHXhhTX (SEQ ID NO:47), wherein h is a hydrophobic amino acid and a is an acidic amino acid. In some embodiments, the intein N-terminal domain comprises the sequence $X_1X_2X_3X_4X_5X_6X_7X_8X_9X_{10}X_{11}X_{12}X_{13}$ $X_{14}$ $X_{15}$ (SEQ ID NO:48), wherein $X_1$ is G or A; $X_2$ is S, K, Q, N, or F; $X_3$ is L, E, K, or R; $X_4$ is I, L, or V; $X_5$ is R, I, V, or N; $X_6$ is A, C, V, or E; $X_7$ is T, S, or D; $X_8$ is K, E, A, P, or N; $X_9$ is D, E, N, or I; $X_{10}$ is H; $X_{11}$ is K, L, Q, or M; $X_{12}$ is F, V, or I; $X_{13}$ is M, P, F, Y, or A; $X_{14}$ is T; and $X_{15}$ is V, Q, K, or L. In some embodiments, the intein N-terminal domain comprises the sequence $X_1X_2X_3X_4X_5X_6X_7X_8X_9X_{10}X_{11}X_{12}X_{13}$ $X_{14}$ $X_{15}$ (SEQ ID NO:49), wherein $X_1$ is G or A; $X_2$ is K, Q, N, or F; $X_3$ is E, K, or R; $X_4$ is I, L, or V; $X_5$ is R, I, V, or N; $X_6$ is C, V, or E; $X_7$ is T, S, or D; $X_8$ is E, A, P, or N; $X_9$ is D, E, N, or I; $X_{10}$ is H; $X_{11}$ is K, L, Q, or M; $X_{12}$ is F, V, or I; $X_{13}$ is P, F, Y, or A; $X_{14}$ is T; and $X_{15}$ is Q, K, or L.

The first amino acid in an intein N-terminal domain is highly conserved and is important for the protein splicing reaction. Therefore, in some embodiments, the first amino acid in an intein N-terminal domain is a cysteine. In some embodiments, the first amino acid in an intein N-terminal domain is a serine. In other embodiments, the first amino acid in an intein N-terminal domain can be mutated to an amino acid that prevents or decreases cleavage between a heterologous polypeptide or N-extein and the intein. Thus, in some embodiments, the first amino acid in an intein N-terminal domain is an amino acid other than serine or cysteine. For example, the first amino acid in an intein N-terminal domain can be an alanine.

In some embodiments, the intein N-terminal domain is about 50 to about 150 amino acids. In some embodiments, the intein N-terminal domain is about 60 to about 140 amino acids. In some embodiments, the intein N-terminal domain is about 75 to about 125 amino acids. In some embodiments, the intein N-terminal domain is about 70 to about 80, about 80 to about 90, about 90 to about 100, about 100 to about 110, about 110 to about 120, or about 120 to about 130 amino acids.

In some embodiments, an intein N-terminal domain comprises the amino acids of a sequence selected from the group consisting of SEQ ID NOs: 3, 12, 20, 34 and 64.

In some embodiments, an intein N-terminal domain comprises a sequence that is at least about 80%, at least about 85%, at least about 90%, at least about 95%, at least about 96%, at least about 97%, at least about 98%, or at least about 99% identical to a sequence selected from the group consisting of SEQ ID NOs: 3, 12, 20, 34 and 64.

In some embodiment, the intein N-terminal domain comprises the sequence corresponding to the N-terminal domain of gp4l-1 (SEQ ID NO:79), 41-2 (SEQ ID NO:80), gp4l-3 (SEQ ID NO:81), gp4l-4 (SEQ ID NO:82), 41-5 (SEQ ID NO:83), gp4l-6 (SEQ ID NO:84), gp4l-7 (SEQ ID NO:85), 41-8 (SEQ ID NO:86), IMPDH-1 (SEQ ID NO:87), NrdA-1 (SEQ ID NO:88), NrdA-2 (SEQ ID NO:89), NrdA-4 (SEQ ID NO:90), NrdA-5 (SEQ ID NO:91), NrdA-6 (SEQ ID NO:92), NrdJ-1 (SEQ ID NO:93) and NrdJ-2 (SEQ ID NO:94).

In some embodiments, an intein N-terminal domain contains at least about 10, at least about 20, at least about 30, at least about 40, or at least about 50 amino acids of a sequence selected from the group consisting of SEQ ID NO: 3, 12, 20, 34 and 64. In some embodiments, an intein N-terminal domain contains at least about 10, at least about 20, at least about 30, at least about 40, or at least about 50 consecutive amino acids of a sequence selected from the group consisting of SEQ ID NO: 3, 12, 20, 34 and 64. In some embodiments, an intein N-terminal domain contains a deletion of no more than about 5, about 10, about 15, about 20, or about 25 amino acids of a sequence selected from the group consisting of SEQ ID NO: 3, 12, 20, 34 and 64. In some embodiments, an intein N-terminal domain contains a deletion of no more than about 5, about 10, about 15, about 20, or about 25 consecutive amino acids of a sequence selected from the group consisting of SEQ ID NO: 3, 12, 20, 34 and 64.

In some embodiments, an intein N-terminal domain comprises a sequence that is at least about 75%, at least about 80%, at least about 85%, at least about 90%, at least about 95%, or at least about 99% identical to a sequence of SEQ ID NO:3.

In some embodiments, an intein N-terminal domain comprises a sequence that is at least about 30%, at least about 35%, at least about 40%, at least about 45%, is at least about 50%, at least about 55%, at least about 60%, at least about 70%, at least about 75%, at least about 80%, at least about 85%, at least about 90%, at least about 95%, or at least about 99% identical to a sequence of SEQ ID NO:12.

In some embodiments, an intein N-terminal domain comprises a sequence that is at least about 40%, at least about 45%, is at least about 50%, at least about 55%, at least about 60%, at least about 70%, at least about 75%, at least about 80%, at least about 85%, at least about 90%, at least about 95%, or at least about 99% identical to a sequence of SEQ ID NO: 20.

In some embodiments, an intein N-terminal domain comprises a sequence that is at least about 30%, at least about 35%, at least about 40%, at least about 45%, is at least about 50%, at least about 55%, at least about 60%, at least about 70%, at least about 75%, at least about 80%, at least about 85%, at least about 90%, at least about 95%, or at least about 99% identical to a sequence of SEQ ID NO: 64.

In some embodiments, an intein N-terminal domain comprises a sequence that is at least about 75%, at least about 80%, at least about 85%, at least about 90%, at least about 95%, or at least about 99% identical to a sequence of SEQ ID NO: 34.

An "intein C-terminal domain" refers to an intein sequence that comprises a C-terminal amino acid sequence that is functional for trans-splicing reactions and/or C-terminal self-cleavage reactions. An intein C-terminal domain can be spliced out when trans-splicing occurs. Suitable assays for determining whether a given polypeptide is an intein C-terminal domain can be found in example 1 of the present invention, which provides an assay for measuring the transplicing activity in the presence of a functional N-terminal intein domain or in example 5, which provides an assay for detecting C-terminal self-cleavage of a fusion protein comprising a C-terminal intein and a heterologous polypeptide in the presence of an N-terminal intein domain carrying a mutation in the first cysteine residue.

The intein C-terminal domain can comprise the C1 and/or C2 motifs of the HINT (Hog/Intein) family.

In some embodiments, the intein C-terminal domain comprises a C2 box (F box) sequence. The C2 box is a non-strictly conserved sequence. The C2 box can comprise, for example, the sequence XhhDIpVXXpHXFX (SEQ ID NO: 50), wherein h is a hydrophobic amino acid and p is a polar amino acid. In some embodiments, the intein C-terminal domain comprises the sequence $X_1X_2X_3X_4X_5X_6X_7X_8X_9X_{10}$ $X_{11}X_{12}X_{13}X_{14}$ (SEQ ID NO:51), wherein $X_1$ is N, E, L, K, Q, D, P, or R; $X_2$ is V, L, or T; $X_3$ is Y, I, V, H, or F; $X_4$ is D; $X_5$ is I or L; $X_6$ is G, E, T, Q, or K; $X_7$ is V or T; $X_8$ is E, S, T, D, N, or K; $X_9$ is R, G, D, N, Q, S, or K; $X_{10}$ is D, E, N, T, or K; $X_{11}$ is H, R, S, I, or N; $X_{12}$ is N, L, S, I, or N; $X_{13}$ is F, Y, L, or I; and $X_{14}$ is A, Y, F, N, C, or S. In some embodiments, the intein C-terminal domain comprises the sequence $X_1X_2X_3X_4X_5X_6X_7X_8X_9X_{10}X_{11}X_{12}X_{13}$ $X_{14}$ (SEQ ID NO:52), wherein $X_1$ is E, L, K, Q, D, P, or R; $X_2$ is V, L, or T; $X_3$ is Y, I, V, H, or F; $X_4$ is D; $X_5$ is I or L; $X_6$ is G, E, T, Q, or K; $X_7$ is V or T; $X_8$ is E, S, T, D, N, or K; $X_9$ is G, D, N, Q, S, or K; $X_{10}$ is D, E, N, T, or K; $X_{11}$ is H, R, S, I, or N; $X_{12}$ is N, L, S, I, or N; $X_{13}$ is F, Y, L, or I; and $X_{14}$ is A, Y, F, N, C, or S.

In some embodiments, the intein C-terminal domain comprises part of the C1 box (G box) sequence. The C1 box is a non-strictly conserved sequence. The C1 box can comprise, for example, the sequence hNXIhXHNn (SEQ ID NO: 53), wherein h is a hydrophobic amino acid and n is a nucleophilic amino acid. In some embodiments, the intein C-terminal domain comprises the sequence $X_1X_2X_3X_4X_5X_6X_7X_8X_9$ (SEQ ID NO: 54), wherein $X_1$ is L, A, V, I, or C; $X_2$ is N or R; $X_3$ is G, D, A, or N; $X_4$ is I, F, or T; $X_5$ is L, I, or V; $X_6$ is V, I, T, or A; $X_7$ is H or S; $X_8$ is N; and $X_9$ is S, T, or C. In some embodiments, the intein C-terminal domain comprises the sequence $X_1X_2X_3X_4X_5X_6X_7X_8X_9$ (SEQ ID NO:55), wherein $X_1$ is A, V, I, or C; $X_2$ is N or R; $X_3$ is G, D, A, or N; $X_4$ is I, F, or T; $X_5$ is L or V; $X_6$ is V, I, or T; $X_7$ is H; $X_8$ is N; and $X_9$ is S, T, or C. Within the C1 box sequence, the amino acids from $X_1$ to $X_8$ correspond to the intein sequence, and $X_9$ corresponds to the first amino acid of the extein.

In some embodiments, an intein C-terminal C1-Box domain comprises a sequence that is at least about 75%, at least about 80%, at least about 85%, at least about 90%, at least about 95%, or at least about 99% identical to a sequence corresponding to the last 8 amino acids of SEQ ID NO:7.

In some embodiments, an intein C-terminal C1-Box domain comprises a sequence that is at least about 75%, at least about 80%, at least about 85%, at least about 90%, at least about 95%, or at least about 99% identical to a sequence corresponding to the last 8 amino acids of SEQ ID NO:16.

In some embodiments, an intein C-terminal C1-Box domain comprises a sequence that is at least about 45%, at least about 50%, at least about 55%, at least about 60%, at least about 65%, at least about 70%, at least about 75%, at least about 80%, at least about 85%, at least about 90%, at least about 95%, or at least about 99% identical to a sequence corresponding to the last 8 amino acids of SEQ ID NO: 38.

In some embodiments, an intein C-terminal C1-Box domain comprises a sequence that is at least about 70%, at least about 75%, at least about 80%, at least about 85%, at least about 90%, at least about 95%, or at least about 99% identical to a sequence corresponding to the last 8 amino acids of SEQ ID NO:65.

In some embodiments, an intein C-terminal C1-Box domain comprises a sequence that is at least about 50%, at least about 55%, at least about 60%, at least about 70%, at least about 75%, at least about 80%, at least about 85%, at least about 90%, at least about 95%, or at least about 99% identical to a sequence corresponding to the last 8 amino acids of SEQ ID NO:24.

The last two amino acids in an intein C-terminal domain are highly conserved and are important for the protein splicing reaction. Therefore, in some embodiments, the last amino acid in an intein C-terminal domain is an asparagine. In some embodiments, the last amino acid in an intein C-terminal domain is a glutamine. In some embodiments, the penultimate amino acid in an intein C-terminal domain is a histidine. In other embodiments, the last and/or penultimate amino acid in an intein C-terminal domain can be mutated to an amino acid that prevents or decreases cleavage between a heterologous polypeptide or extein and the intein. Thus, in some embodiments, the last amino acid in an intein C-terminal domain is an amino acid other than asparagine or glutamine. In some embodiments, the penultimate amino acid in an intein C-terminal domain is an amino acid other than histidine. In some embodiments, the last amino acid in an intein C-terminal domain is an amino acid other than asparagine or glutamine and the first amino acid in an extein C-terminal domain is an amino acid other than serine. For example, the last amino acid in an intein C-terminal domain and/or the first amino acid in an extein C-terminal domain can be an alanine.

In some embodiments, the intein C-terminal domain is about 10 to about 80 amino acids. In some embodiments, the intein C-terminal domain is about 20 to about 70 amino acids. In some embodiments, the intein C-terminal domain is about 30 to about 60 amino acids. In some embodiments, the intein C-terminal domain is about 25 to about 35, about 30 to about 40, about 35 to about 45, about 40 to about 50, about 45 to about 55, or about 55 to about 65 amino acids.

In some embodiments, an intein C-terminal domain comprises the amino acids of a sequence selected from the group consisting of SEQ ID NOs: 7, 16, 24, 38 and 65. In some embodiments, an intein C-terminal domain comprises a sequence that is at least about 80%, at least about 85%, at least about 90%, at least about 95%, at least about 96%, at least about 97%, at least about 98%, or at least about 99% identical to a sequence selected from the group consisting of SEQ ID NOs: 7, 16, 24, 38 and 65. In some embodiments, an intein C-terminal domain contains at least about 10, at least about 20, at least about 30, at least about 40, or at least about 50 amino acids of a sequence selected from the group consisting of SEQ ID NO:7, 16, 24, 38 and 65. In some embodiments, an intein C-terminal domain contains at least about 10, at least about 20, at least about 30, at least about 40, or at least about 50 consecutive amino acids of a sequence selected from the group consisting of SEQ ID NO: 7, 16, 24, 38 and 65. In some embodiments, an intein C-terminal domain contains a deletion of no more than about 5, about 10, about 15, about 20, or about 25 amino acids of a sequence selected from the group consisting of SEQ ID NO: 7, 16, 24, 38 and 65. In some embodiments, an intein C-terminal domain contains a deletion of no more than about 5, about 10, about 15, about 20, or about 25 consecutive amino acids of a sequence selected from the group consisting of SEQ ID NO: 7, 16, 24, 38 and 65.

In some embodiments, an intein C-terminal domain comprises a sequence that is at least about 75%, at least about 80%, at least about 85%, at least about 90%, at least about 95%, or at least about 99% identical to a sequence of SEQ ID NO: 7.

In some embodiments, an intein C-terminal domain comprises a sequence that is at least about 30%, at least about 35%, at least about 40%, at least about 45%, is at least about 50%, at least about 55%, at least about 60%, at least about 70%, at least about 75%, at least about 80%, at least about 85%, at least about 90%, at least about 95%, or at least about 99% identical to a sequence of SEQ ID NO:16.

In some embodiments, an intein C-terminal domain comprises a sequence that is at least about 40%, at least about 45%, is at least about 50%, at least about 55%, at least about 55%, at least about 60%, at least about 70%, at least about 75%, at least about 80%, at least about 85%, at least about 90%, at least about 95%, or at least about 99% identical to a sequence of SEQ ID NO:24.

In some embodiment, the intein C-terminal domain comprises the sequence corresponding to the C-terminal domain of gp41-1 (SEQ ID NO:95), gp41-2 (SEQ ID NO:96), gp41-3 (SEQ ID NO:97), gp41-8 (SEQ ID NO:98), gp41-8 (SEQ ID NO:99), IMPDH-1 (SEQ ID NO:100), IMPDH-2 (SEQ ID NO:101), IMPDH-3 (SEQ ID NO:102), NrdA-2 (SEQ ID NO:103), NrdA-3 (SEQ ID NO:104), NrdA-5 (SEQ ID NO:105), NrdA-6 (SEQ ID NO:106), NrdA-7 (SEQ ID NO:107), NrdJ-1 (SEQ ID NO:108).

In some embodiments, the intein N-terminal domain and the intein C-terminal domain have opposite charges. Thus, in some embodiments, the intein N-terminal domain is negatively charged, and the intein C-terminal domain is positively charged. In other embodiments, the intein N-terminal domain is positively charged, and the intein C-terminal domain is negatively charged.

TABLE 1

| Intein domain | SEQ ID NO: | | Sequence | | | |
|---|---|---|---|---|---|---|
| N-terminal domain of GP41.1 | 3 | 1<br>61 | CLDLKTQVQT<br>EEHLFPTQTG | PQGMKEISNI<br>EMNISGGLKE | QVGDLVLSNT<br>GMCLYVKE | GYNEVLNVFP KSKKKSYKIT LEDGKEIICS |
| N-terminal domain of GP41.8 | 12 | 1<br>61 | CLSLDTMVVT<br>ANHKFPTKDG | NGKAIEIRDV<br>LKTINSGLKV | KVGDWLESEC<br>GDFLRSRA | GPVQVTEVLP IIKQPVFEIV LKSGKKIRVS |
| N-terminal domain of NrdJ1 | 20 | 1<br>61 | CLVGSSEIIT<br>VELEINTLHG | RNYGKTTIKE<br>VKTIRCTPDH | VVEIFDNDKN<br>PVYTKNRDYV | IQVLAFNTHT DNIEWAPIKA AQLTRPNAEL<br>RADELTDDDE LVVAI |
| N-terminal domain of IMPDH1 | 34 | 1<br>61 | CFVPGTLVNT<br>EFYVIDKENA | ENGLKKIEEI<br>NRVNEDNIHL | KVGDKVFSHT<br>FARWVHAEEL | GKLQEVVDTL IFDRDEEIIS INGIDCTKNH<br>DMKKHLLIEL E |
| N-terminal domain of NrdA-2 | 64 | 1<br>61 | CLTGDAKIDV<br>SAEVLEIIDE | LIDNIPISQI<br>ETGQKIVCTP | SLEEVVNLFN<br>DHKVYTLNRG | EGKEIYVLSY NIDTKEVEYK EISDAGLISE<br>YVSAKDLKED DELVFS |
| N-terminal domain of DNA-E | 28 | 1<br>61 | CLSYETEILT<br>EDGSLIRATK | VEYGLLPIGK<br>DHKFMTVDGQ | IVEKRIECTV<br>MLPIDEIFER | YSVDNNGNIY TQPVAQWHDR GEQEVFEYCL<br>ELDLMRVDNL PN |
| C-terminal domain of GP41.1 | 7 | 1 | MMLKKILKIE | ELDERELIDI | EVSGNHLFYA NDILTHN | |
| C-terminal domain of GP41.8 | 16 | 1 | MCEIFENEID | WDEIASIEYV | GVEETIDINV TNDRLFFANG ILTHN | |
| C-terminal domain of NrdJ1 | 24 | 1 | MEAKTYIGKL | KSRKIVSNED | TYDIQTSTHN FFANDILVHN | |
| C-terminal domain of IMPDH1 | 38 | 1 | MKFKLKEITS | IETKHYKGKV | HDLTVNQDHS YNVRGTVVHN | |
| C-terminal domain of NrdA-2 | 65 | 1 | MGLKIIKRES | KEPVFDITVK | DNSNFFANNI LVHN | |
| C-terminal domain of DNA-E | 31 | 1 | MIKIATRKYL | GKQNVYDIGV | ERDHNFALKN GFIASN | |

Sequences of the N- and C-terminal domains of the inteins used in the present invention. Underlined sequences correspond to the N1-boxes of the intein N-terminal domains. Double underlined sequences correspond to the C1 boxes of the intein c-terminal domains (Lacking the first amino acid of the extein).

60%, at least about 70%, at least about 75%, at least about 80%, at least about 85%, at least about 90%, at least about 95%, or at least about 99% identical to a sequence of SEQ ID NO:38.

In some embodiments, an intein C-terminal domain comprises a sequence that is at least about 30%, at least about 35%, at least about 40%, at least about 45%, is at least about 50%, at least about 55%, at least about 60%, at least about 70%, at least about 75%, at least about 80%, at least about 85%, at least about 90%, at least about 95%, or at least about 99% identical to a sequence of SEQ ID NO:65.

In some embodiments, an intein C-terminal domain comprises a sequence that is at least about 50%, at least about Among the several boxes identified in inteins and split inteins (N1, N2, C1 and C2) protein sequences, C1 is the most conserved box and is directly involved in the trans-splicing reaction. The central role of C1 is considered an important characteristic in classifying and grouping split inteins.

In some embodiments, an intein C-terminal domain contains a C1-Box that is at least about 60%, at least about 80%, at least about 85%, at least about 90%, at least about 95%, or at least about 99% identical to the sequence ANDILTHNS (SEQ ID NO:78), corresponding to the C1-Box of the C-terminal domain of the gp-41-1 split intein.

TABLE 2

Percentage of identity of C1 boxes (also known as G boxes) from several split inteins with regard to gp41-1 C1 box (ANDILTHNS, SEQ ID NO: 78)

| Split intein name | % of identity versus gp41-1 C1 box |
|---|---|
| gp41-2 | 87.5 |
| gp41-8 | 87.5 |
| gp41-9 | 100 |
| NrdA2 | 75 |
| NrdA3 | 87.5 |
| NrdA6 | 62.5 |
| NrdA7 | 87.5 |
| NrdJ1 | 87.5 |
| Npu DNA-E | 25 |

As for the rest of the patent, the identity is calculated as the percentage of identical amino acids with regard to of to the total number of amino acids. For clarity purposes, the identity is calculated between two sequences having the same length. The DNA-E intein known from the prior art differs from the remaining inteins in that the C1 box does not show substantial identity to the gp41-1 C1 box.

III. Intein Fusion Proteins

Fusion proteins comprising split inteins are also described herein. The intein N-terminal domain and/or the intein C-terminal domain can be fused either directly (i.e., via a peptide bond) or indirectly (i.e., via a linker amino acid sequence) to a heterologous polypeptide.

Thus, in some embodiments, a heterologous polypeptide is fused either directly or indirectly to the N-terminus of an intein N-terminal domain. Such polypeptides can optionally also comprise additional amino acids or heterologous polypeptides fused directly or indirectly to the C-terminus of the intein N-terminal domain (e.g., expression or purification tags) or fused directly or indirectly to the N-terminus of the heterologous polypeptide.

In some embodiments, a heterologous polypeptide is fused either directly or indirectly to the C-terminus of an intein C-terminal domain. Such polypeptides can optionally also comprise additional amino acids or heterologous polypeptides fused directly or indirectly to the N-terminus of the intein C-terminal domain (e.g., expression or purification tags) or fused directly or indirectly to the C-terminus of the heterologous polypeptide.

In some embodiments, a fusion protein comprising a heterologous polypeptide fused to the C-terminus of an intein C-terminal domain and a fusion protein comprising a heterologous polypeptide fused to the N-terminus of the an intein N-terminal domain are expressed as two separate polypeptides.

In some embodiments, a fusion protein comprising a heterologous polypeptide fused to the C-terminus of an intein C-terminal domain and a fusion protein comprising a heterologous polypeptide fused to the N-terminus of the an intein N-terminal domain are expressed as a single polypeptide. The fusion protein comprising a heterologous polypeptide fused to the C-terminus of an intein C-terminal domain can be separated from the fusion protein comprising a heterologous polypeptide fused to the N-terminus of the an intein N-terminal domain by about 1 to about 1000, about 1 to about 500, about 1 to about 250, about 1 to about 200, about 1 to about 150, about 1 to about 100, or about 1 to about 50 amino acids.

In some embodiments, a fusion protein comprises an intein C-terminal domain fused to the N-terminus of a heterologous polypeptide. In a preferred embodiment, the fusion protein comprises (i) an intein domain at least 75% identical to a sequence selected from the group consisting of SEQ ID NOs: 7, 16, 24, 38 and 65 and (ii) a heterologous polypeptide, wherein the heterologous polypeptide is C-terminal to the intein domain. In a still more preferred embodiment, the last amino acid of the intein domain is glutamine or asparagine. In yet another embodiment, the first amino acid of the heterologous polypeptide is selected from the group consisting of Met, Cys, Thr, Arg, Lys, Ser, Gln, His, Ala, Tyr, Phe, Asn, Tip, Val, Leu, Asp, Ile, Gly, Glu or Pro. In another embodiment, the last amino acid of the intein domain is an amino acid other than asparagine or glutamine and the first amino acid of the heterologous polypeptide is selected from the group consisting of Met, Cys, Thr, Arg, Lys, Ser, Gln, His, Ala, Tyr, Phe, Asn, Trp, Val, Leu, Asp, Ile, Gly, Glu or Pro. In another embodiment, the last amino acid of the intein domain is an amino acid other than asparagine or glutamine and the first amino acid of the heterologous polypeptide is an amino acid other than serine, cysteine, or threonine.

In some embodiments, a fusion protein comprises an intein N-terminal domain fused to the C-terminus of a heterologous polypeptide. In another embodiment, the fusion protein comprises (i) an intein domain at least 75% identical to a sequence selected from the group consisting of SEQ ID NOs: 3, 12, 20, 34 and 64 and (ii) a heterologous polypeptide, wherein the heterologous polypeptide is N-terminal to the intein domain. In a preferred embodiment, the first amino acid of the intein domain is a serine or cysteine. In yet another embodiment, the first amino acid of the intein domain is an amino acid other than serine or cysteine.

The heterologous polypeptide can be, for example, an enzyme, a hormone, such as calcitonin, erythropoietin, thrombopoietin, human growth hormone, epidermal growth factor, and the like, an interferon, a cytokine, a protein having therapeutic, nutraceutical, agricultural, or industrial use. Additional heterologous polypeptides can be enzymes, antibodies, antibody fragments, and pharmaceutical proteins. A heterologous polypeptide can also be a polypeptide fragment.

The heterologous polypeptide can also be, for example, an antibody chain, single domain antibodies, camelid heavy-chain antibody (VHH or nanobodies), or a recombinant antibody developed using combinations of antibody domains, such as monovalent (fragment variable (Fv), disulfide-stabilized Fv antibody fragment (dsFv), scFv, single-chain antibody fragment (scAb) and Fab), divalent (minibody, diabody, F(ab')2 and (scFv)2) and multivalent (tetrabody, triabody and F(ab')3) formats (FIG. 3 from Vijayalakshmi B et al. Methods Volume 56, Issue 2, February 2012, 116-129).

In some embodiments, the first amino acid of the heterologous polypeptide is a serine, cysteine, or threonine. In some embodiments, the first amino acid of the heterologous polypeptide is not a serine, cysteine, or threonine.

In some embodiments, a fusion protein comprising a heterologous polypeptide and an intein or intein domain further comprises additional sequences such as purification tags or expression tags. Such expression and/or purification tags include, for example, Strep, His, and Myc tags.

In some embodiments, the fusion protein further comprises a sequence that increases protein solubility, e.g., a phage bacteriophage lambda head protein D (gpD), tioredoxine (Tx) or GST.

In some embodiments a fusion protein comprising a heterologous polypeptide and an intein N- and/or C-terminal domain can comprise an additional chemical moiety including, among others, fluorescence groups, biotin, polyethylene glycol (PEG), amino acid analogs, unnatural amino acids, phosphate groups, glycosyl groups, radioisotope labels, and pharmaceutical molecules. In other embodiments, the heterologous polypeptide can comprise one or more chemically reactive groups including, among others, ketone, aldehyde, Cys residues and Lys residues.

In some embodiments, the fusion protein comprises a linker between the heterologous polypeptide and the intein sequence. Thus, the fusion protein can comprise a linker between the C-terminus of the heterologous protein and the N-terminus of the N-terminal domain of the intein. The fusion protein can also comprise a linker between the N-terminus of the heterologous protein and the C-terminus of the C-terminal domain of the intein. The linker can be, for example, from 1-10 amino acids in length. The linker can be 1-5 amino acids in length. Thus, the linker can contain 1, 2, 3, 4, or 5 amino acids. In some embodiments, the linker can comprise an extein sequence.

In some embodiments, the first amino acid off the linker contacting the heterologous polypeptide and the C-terminus of the C-terminal domain of an intein is selected from the group consisting of Met, Cys, Thr, Arg, Lys, Ser, Gln, His, Ala, Tyr, Phe, Asn, Tip, Val, Leu, Asp, Ile, Gly, Glu or Pro. In yet another embodiment, the first amino acid off the linker contacting the heterologous polypeptide and the C-terminus of the C-terminal domain of an intein can comprise a serine, cysteine, or threonine. A serine, cysteine, or threonine adjacent to the C-terminus of the C-terminal domain of an intein can increase the efficiency of C-terminal cleavage (i.e., cleavage between the intein C-terminal domain and the serine, cysteine, or threonine of the heterologous polypeptide). In some embodiments, the first, second, third, fourth and/or fifth amino acid of the linker is a serine, cysteine, or threonine.

In some embodiments, the linker can comprise a native extein sequence. As used herein, the term "extein" refers to the sequence naturally found next to an intein or intein domain. Thus, a heterologous polypeptide, which is a polypeptide not naturally found next to an intein or intein domain, is not an extein. In some embodiments, the extein comprises a sequence selected from the group consisting of SEQ ID NOs: 4, 8, 13, 17, 21, 25, 35, and 39. In some embodiments, a linker comprising amino acids of an extein comprises, for example, the first (i.e., N-terminal) 1-5 amino acids of a sequence selected from the group consisting of SEQ ID NOs: 4, 8, 13, 17, 21, 25, 35, and 39. In some embodiments, the linker comprises 1, 2, 3, 4, or 5 amino acids of a sequence selected from the group consisting of SEQ ID NOs: 4, 8, 13, 17, 21, 25, 35, and 39. In some embodiments, a fusion protein comprises an intein domain and an extein domain that are naturally found together. In other embodiments, a fusion protein comprises an intein domain and an extein domain that are not naturally found together, i.e., a heterologous extein domain. By way of example, a fusion protein can comprise a Gp41.1 intein domain and a heterologous extein domain such an IMPDH extein domain.

III. Polynucleotides Encoding Intein Fusions and Expression of Intein Fusions

Polynucleotides that encode intein fusions are also described herein. The polynucleotides can be in the form of RNA or DNA. DNA includes cDNA, genomic DNA, and synthetic DNA; and can be double-stranded or single-stranded, and if single stranded can be the coding strand or non-coding (anti-sense) strand. In certain embodiments, the polynucleotides are isolated. In certain embodiments, the polynucleotides are substantially pure.

Such polynucleotides can, for example, be incorporated in an expression vector for producing intein fusion proteins. Expression vectors are replicable DNA constructs that have synthetic or cDNA-derived DNA fragments encoding an intein fusion protein, operatively linked to suitable transcriptional or translational regulatory elements. The transcriptional or translational regulatory elements can be derived from, for example, mammalian, microbial, viral, or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR 1, pBR322, pMB9 and their derivatives, wider host range plasmids, such as M13 and filamentous single-stranded DNA phages.

In some embodiments, a vector comprising a polynucleotide that encodes an intein further comprises a multiple cloning site. A multiple cloning site is a polynucleotide sequence comprising one or more unique restriction sites. Non-limiting examples of the restriction sites include EcoRI, SacI, KpnI, SmaI, XmaI, BamHI, XbaI, HincII, PstI, SphI, HindIll, AvaI, or any combination thereof.

Multiple cloning sites can be used in vectors comprising a polynucleotide encoding an intein to simplify the insertion of a polynucleotide encoding a heterologous polypeptide into the vector such that the vector can be used to express a fusion protein comprising the intein and the heterologous polypeptide. Thus, for example, a vector can comprise a sequence encoding an intein C-terminal domain upstream of a multiple cloning site so that a sequence encoding a heterologous polypeptide can be easily inserted downstream of the intein C-terminal domain. A vector can also comprise a sequence encoding an intein N-terminal domain downstream of a multiple cloning site so that a sequence encoding a heterologous polypeptide can be easily inserted upstream of the intein N-terminal domain.

Thus, for example, a vector can comprise a sequence encoding an intein C-terminal domain upstream of a multiple cloning site, which is in its turn upstream of a sequence encoding an intein N-terminal domain so that a sequence encoding a heterologous polypeptide can be easily inserted downstream of the intein C-terminal domain and upstream of the intein N-terminal domain.

A vector comprising a polynucleotide with a multiple cloning site upstream of an intein N-terminal domain can be combined in a kit with a vector comprising a polynucleotide with a multiple cloning site downstream of an intein C-terminal domain. In some embodiments, a single vector comprises a polynucleotide with a multiple cloning site upstream of an intein N-terminal domain and a polynucleotide with a multiple cloning site downstream of an intein C-terminal domain. In such vectors, each of the polynucleotide with a multiple cloning site upstream of an intein N-terminal domain and the polynucleotide with a multiple cloning site downstream of an intein C-terminal domain can be operably linked to regulatory sequences, and the regulatory sequences can be the same or different.

The vectors can comprise at least one promoter. The promoter can be any sequence that is suitable for driving expression of an intein domain or intein fusion.

Different hosts often have preferences for a particular codon to be used for encoding a particular amino acid residue. Such codon preferences are well known and a DNA sequence encoding a desired fusion protein sequence can be altered, using in vitro mutagenesis for example, so that host-preferred codons are utilized for a particular host in which the fusion protein is to be expressed.

A recombinant nucleic acid molecule such as a DNA molecule, comprising a gene vector or construct containing one or more regulatory sequences (control elements) such as a promoter suitable for driving the expression of the gene in a compatible bacterial or eukaryotic host cell organism operatively linked to an exogenous nucleic acid segment (e.g., a DNA segment or sequence) that defines a gene that encodes a contemplated fusion protein, as discussed above, is also contemplated. More particularly, also contemplated is a recombinant DNA molecule that comprises a gene vector comprising a promoter for driving the expression of the fusion protein in host organism cells operatively linked to a DNA segment that defines a gene encodes an intein domain linked to a heterologous polypeptide. That recombinant DNA molecule, upon suitable transfection and expression in a host cell, provides a contemplated fusion protein.

As is well known in the art, so long as the required nucleic acid, illustratively DNA sequence, is present, (including start and stop signals), additional base pairs can usually be present at either end of the DNA segment, and that segment can still be utilized to express the protein. This, of course, presumes the absence in the segment of an operatively linked DNA sequence that represses expression, expresses a further product that consumes the fusion protein desired to be expressed, expresses a product that consumes a wanted reaction product produced by that desired fusion protein, or otherwise interferes with expression of the gene of the DNA segment.

Thus, so long as the DNA segment is free of such interfering DNA sequences, a DNA segment of the invention can be about 500 to about 15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known.

A DNA segment that encodes a fusion protein can be synthesized by chemical techniques, for example, the phosphotriester method of Matteucci et al., 1981 J. Am. Chem. Soc., 103:3185. Of course, by chemically synthesizing the coding sequence, any desired modifications can be made simply by substituting the appropriate bases for those encoding the native amino acid residue sequence.

DNA segments containing a gene encoding the fusion protein can also be obtained from recombinant DNA molecules (plasmid vectors) containing that gene.

A vector that directs the expression of a fusion protein gene in a host cell is referred to herein as an "expression vector". An expression vector contains expression control elements including the promoter. The fusion protein-coding gene is operatively linked to the expression vector to permit the promoter sequence to direct RNA polymerase binding and expression of the fusion protein-encoding gene. Useful in expressing the polypeptide coding gene are promoters that are inducible, viral, synthetic, constitutive as described by Paszkowski et al., 1989 EMBO J., 3:2719 and Odell et al., 1985 Nature, 313:810, as well as temporally regulated, spatially regulated, and spatiotemporally regulated as given in Chua et al., 1989 Science, 244:174-181.

Expression vectors compatible with eukaryotic cells, such as those compatible with cells of prokaryotes (*E. coli*), mammals, algae or insects and the like, are contemplated herein. Such expression vectors can also be used to form the recombinant DNA molecules of the present invention. Prokaryotic and eukaryotic cell expression vectors are well known in the art and are available from several commercial sources. Normally, such vectors contain one or more convenient restriction sites for insertion of the desired DNA segment and promoter sequences. Optionally, such vectors contain a selectable marker specific for use in prokaryotic or eukaryotic cells.

The choice of which expression vector and ultimately to which promoter a fusion protein-encoding gene is operatively linked depends directly on the functional properties desired, e.g., the location and timing of protein expression, and the host cell to be transformed. These are well known limitations inherent in the art of constructing recombinant DNA molecules. However, a vector useful in practicing the present invention can direct the replication, and preferably also the expression (for an expression vector) of the fusion protein gene included in the DNA segment to which it is operatively linked.

The split intein fusion proteins can be expressed in any cell type. For example, split intein fusion proteins can be expressed in prokaryotes, plants (e.g., monocots or dicots), animals, insects, fungi, or yeasts (e.g., *Saccharomyces* or *Pichia*). Suitable cells include, by way of example, plants (e.g., tomato, tobacco, arabidopsis, alfalfa), mammalian cells (e.g., CHO, COS and 293T cells), filamentous fungi (e.g., *Tricoderma resei* and *Aspergillus* sp.), and insect cells. Examples of suitable mammalian host cell lines include the COS-7 lines of monkey kidney cells, described by Gluzman (*Cell* 23:175, 1981), and other cell lines capable of expressing an appropriate vector including, for example, L cells, C127, 3T3, Chinese hamster ovary (CHO), HeLa and BHK cell lines. Baculovirus systems for production of heterologous proteins in insect cells are reviewed by Luckow and Summers, *Bio/Technology* 6:47 (1988). Split intein fusion proteins can be purified from such cells using techniques that are known in the art. In addition, split intein fusion proteins can be produced in cell-free transcription/translational systems.

IV. Compositions Comprising Intein Fusions

The invention also relates to compositions and kits-of-parts containing the fusion proteins of the invention. The term "composition", as used herein, refers to a combination of one or more components wherein the components may be:
(i) provided as separate formulations (i.e. independently of one another), which are subsequently brought together for use in conjunction with each other; or
(ii) packaged and presented together as separate components of a "combination pack" for use in conjunction with each other.

In one embodiment, the composition or kit-of-parts comprises components adequate for C-terminal cleavage of a polypeptide which is connected to the C-terminus of the C-terminal domain of a intein. These compositions comprise
(i) a first component which is a fusion protein comprising
   (i) an intein domain at least 75% identical to a sequence selected from the group consisting of SEQ ID NOs: 7, 16, 24, 38 and 65 and (ii) a heterologous polypeptide, wherein the heterologous polypeptide is C-terminal to the intein domain and
(ii) a second component which is selected from the group consisting of a fusion protein comprising (i) an intein domain at least 75% identical to a sequence selected from the group consisting of SEQ ID NOs: 3, 12, 20, 34 and 64 and (ii) a heterologous polypeptide, wherein the heterologous polypeptide is N-terminal to the intein domain and an N-terminal intein domain wherein the first amino acid of the intein domain is an amino acid other than serine or cysteine.

wherein
a. the intein domain from the fusion protein forming the first component is at least 75% identical to SEQ ID NO:7 and the intein domain from the fusion protein forming the second component or the N-terminal intein domain is at least 75% identical to SEQ ID NO:3;
b. the intein domain from the fusion protein forming the first component is at least 75% identical to SEQ ID NO:16 and the intein domain from the fusion protein of the second component or the N-terminal intein domain is at least 75% identical to SEQ ID NO:12;
c. the intein domain from the fusion protein forming the first component is at least 75% identical to SEQ ID NO:24 and the intein domain from the fusion protein forming the second component or the N-terminal intein domain is at least 75% identical to SEQ ID NO:20;
d. the intein domain from the fusion protein forming the first component is at least 75% identical to SEQ ID NO:38 and the intein domain from the fusion protein forming the second component or the N-terminal intein domain is at least 75% identical to SEQ ID NO:34 or
e. the intein domain from the fusion protein forming the first component is at least 75% identical to SEQ ID NO:65 and the intein domain from the fusion protein forming the second component or the N-terminal intein domain is at least 75% identical to SEQ ID NO:64

In another embodiment, the heterologous polypeptide and the intein domain forming the fusion protein forming the first component of the composition of kit-of-parts are either directly connected by a peptide bond or by a linker. In another embodiment, the last amino acid of the C-terminal intein domain is glutamine or asparagine.

In another embodiment, the second component is selected from the group consisting of an intein domain at least 75% identical to a sequence selected from the group consisting of SEQ ID NOs: 3, 12, 20, 34 and 64, wherein the first amino acid of the intein domain is an amino acid other than serine or cysteine. (no tengo claro que sea necesario que el dominio N de la inteina este fusionado a una proteina heterologa para funcionar).

In another embodiment, the composition or kit-of-parts of the invention comprises components adequate for N-terminal cleavage of a polypeptide which is connected to the N-terminus of the N-terminal domain of an intein. These compositions comprise
(i) a first component which is a fusion protein comprising (i) an intein domain at least 75% identical to a sequence selected from the group consisting of SEQ ID NOs: 3, 12, 20, 34 and 64 and (ii) a heterologous polypeptide, wherein the heterologous polypeptide is N-terminal to the intein domain and
(ii) a second component which is selected from the group consisting of the fusion protein of comprising (i) an intein domain at least 75% identical to a sequence selected from the group consisting of SEQ ID NOs: 7, 16, 24, 38 and 65 and (ii) a heterologous polypeptide, wherein the heterologous polypeptide is C-terminal to the intein domain and a C-terminal intein domain and wherein the last amino acid of the intein domain is an amino acid other than asparagine or glutamine and wherein the first amino acid of the heterologous polypeptide or of the linker is an amino acid other than serine, cysteine, or threonine.

wherein
a. the intein domain from the fusion protein forming the first component is at least 75% identical to SEQ ID NO:3 and the intein domain from the fusion protein forming the second component or the C-terminal intein domain is at least 75% identical to SEQ ID NO:7;
b. the intein domain from the fusion protein forming the first component is at least 75% identical to SEQ ID NO:12 and the intein domain from the second component or the C-terminal intein domain is at least 75% identical to SEQ ID NO:16;
c. the intein domain from the fusion protein forming the first component is at least 75% identical to SEQ ID NO:20 and the intein domain from the fusion protein forming the second component or the C-terminal intein domain is at least 75% identical to SEQ ID NO:24;
d. the intein domain from the fusion protein forming the first component is at least 75% identical to SEQ ID NO:34 and the intein domain from the fusion protein forming the second component or the C-terminal intein domain is at least 75% identical to SEQ ID NO:38 or
e. the intein domain from the fusion protein forming the first component is at least 75% identical to SEQ ID NO:64 and the intein domain from the fusion protein forming the second component or the C-terminal intein domain is at least 75% identical to SEQ ID NO:65.

In a preferred embodiment, the heterologous polypeptide and the intein domain forming the first component of the composition or kit-of-parts are either directly connected by a peptide bond or by a linker. In another embodiment, the first amino acid of the intein domain is a serine or cysteine.

In another embodiment, the second component is selected from the group consisting of an intein domain at least 75% identical to a sequence selected from the group consisting of SEQ ID NOs: 7, 16, 24, 38 and 65, wherein the last amino acid of the intein domain is an amino acid other than asparagine or glutamine.

In another embodiment, the composition or kit-of-parts according to the invention comprises reagents adequate for covalently linking the N-terminus of a first polypeptide to the C-terminus of a second polypeptide, said composition comprising (i) a fusion protein comprising (i) an intein domain at least 75% identical to a sequence selected from the group consisting of SEQ ID NOs: 7, 16, 24, 38 and 65 and (ii) a second heterologous polypeptide, wherein the heterologous polypeptide is C-terminal to the intein domain and (ii) a fusion protein comprising (i) an intein domain at least 75% identical to a sequence selected from the group consisting of SEQ ID NOs: 3, 12, 20, 34 and 64 and (ii) a first heterologous polypeptide, wherein the heterologous polypeptide is N-terminal to the intein domain wherein a. the intein domain from the fusion protein forming the first component is least 75% identical to SEQ ID NO:7 and the intein domain from the fusion protein forming the second component is at least 75% identical to SEQ ID NO:3;

b. the intein domain from the fusion protein forming the first component is at least 75% identical to SEQ ID NO:16 and the intein domain from the fusion protein forming the second component is at least 75% identical to SEQ ID NO:12;

c. the intein domain from the fusion protein forming the first component is at least 75% identical to SEQ ID NO:24 and the intein domain from the fusion protein forming the second component is at least 75% identical to SEQ ID NO:20;

d. the intein domain from the fusion protein forming the first component is at least 75% identical to SEQ ID NO:38 and the intein domain from the fusion protein forming the second component is at least 75% identical to SEQ ID NO:34; or e. the intein domain from the fusion protein forming the first component is at least 75% identical to SEQ ID NO:65 and the intein domain from the fusion protein forming the second component is at least 75% identical to SEQ ID NO:64

In a preferred embodiment, the heterologous polypeptide and the intein domain forming part of the fusion protein which is the first component of the composition are either directly connected by a peptide bond or by a linker In a more preferred embodiment, the last amino acid of the intein domain in the fusion protein which is the first component of the invention is glutamine or asparagine.

In another preferred embodiment, the heterologous polypeptide and the intein domain forming part of the fusion protein which is the second component of the composition are either directly connected by a peptide bond or by a linker. In a more preferred embodiment, the first amino acid of the intein domain in the fusion protein which is the second component of the invention is serine or cysteine.

The ratio of the components in the compositions is adequate for an efficient processing of the fusion proteins. Suitable ratios of the first and second components include, without limitation, 1000:1, 100:1; 10:1, 1:1, 1:10, 1:100 and 1:1000.

V. Methods of Using Intein Fusions

The split inteins and fusion proteins comprising split inteins described herein can be used, for example, to cleave, link (splice) and/or cyclize polypeptide sequences. The intein sequences catalyze these reactions, which can occur in the absence of any other enzymes, chemical additives, or treatments.

In some embodiments, a heterologous polypeptide can be cleaved from an intein domain. For example, a heterologous polypeptide can be cleaved from the C-terminus of an intein C-terminal domain using a split intein comprising a fusion protein comprising an amino acid sequence that prevents or decreases cleavage between a heterologous polypeptide and an intein N-terminal domain. In a preferred embodiment, the first amino acid of the intein N-terminal domain is an amino acid other than cysteine or serine, e.g. alanine The first amino acid of the heterologous polypeptide can be selected in order to increase the yield of the reaction, either because it results in an increased reaction half-life or because it results in an increased k value. Thus, in a preferred embodiment, the first amino acid of the heterologous polypeptide or of the linker connecting the intein C-terminal domain and the heterologous polypeptide is selected from the group consisting of Met, Cys, Thr, Arg, Lys, Ser, Gln, His, Ala, Tyr, Phe, Asn, Trp, Val, Leu, Asp, Ile, Gly, Glu or Pro.

In addition, a heterologous polypeptide can be cleaved from the N-terminus of an intein N-terminal domain using a split intein comprising a fusion protein containing an amino acid sequence that decreases cleavage between a heterologous polypeptide and an intein C-terminal domain. In a preferred embodiment, the last amino acid of the intein C-terminal domain is an amino acid other than glutamine or asparagine, e.g. alanine In some embodiments a first polypeptide can be linked (spliced) to a second polypeptide by contacting a fusion protein comprising the first polypeptide and an intein N-terminal domain with a fusion protein comprising the second polypeptide and an intein C-terminal domain. The C-terminus of the first polypeptide will be linked to the N-terminus of the second polypeptide.

In some embodiments, the split inteins can be used to cyclize a polypeptide that comprises an intein C-terminal domain on the polypeptide's N-terminus and an intein N-terminal domain on the polypeptide's C-terminus.

In some embodiments, the reaction occurs at about 0° C. to about 60° C. In some embodiments, the reaction occurs at about 0° C., about 4° C., about 8° C., about 12° C., about 20° C., about 25° C., about 30° C., about 32° C., about 34° C., about 37° C., about 40° C., about 45° C., about 50° C., about 55° C., or about 60° C.

In some embodiments, the reaction occurs at a pH of about 5 to about 10. In some embodiments, the reaction occurs at a pH of about 6, about 6.5, about 7, about 7.5, about 8, about 8,5, about 9, about 9,5 or about 10.

In some embodiments, the reaction occurs in the presence of a denaturing agent, e.g., to increase protein solubility. In some embodiments, the reaction occurs in the presence of urea. In some embodiments, the reaction occurs in a presence of no more than about 6.5M, about 6M, about 5M, about 4.5M, about 4M, about 3.5M, about 3M, about 2.5M, about 2M, about 1.5M, about 1M, or about 0.5M urea. In some embodiments, the reaction occurs in the presence of about 0.5 to about 6M, about 0.5 to about 4M, about 1 to about 4 M, about 2 to about 4M, or about 3 to about 4M urea. In some embodiments, the reaction occurs in the presence of about 0.5 to about 2M, or about 0.5 to 1M urea.

The methods described herein demonstrate that the split inteins can have robust activity. Thus, in some embodiments, the reaction rate constant is at least about $0.5 \times 10^{-1}$ s$^{-1}$, $1 \times 10^{-1}$ s$^{-1}$, $1.5 \times 10^{-1}$ s$^{-1}$, $0.5 \times 10^{-2}$ s$^{-1}$, about $1 \times 10^{-2}$ s$^{-1}$, about $1.5 \times 10^{-2}$ s$^{-1}$, about $2.0 \times 10^{-2}$ s$^{-1}$, about $2.5 \times 10^{-2}$ s$^{-1}$, or about $3 \times 10^{-2}$ s$^{-1}$ when an intein N-terminal domain and C-terminal domain are mixed in equimolar concentrations. In addition, the reaction rate half life can be less than about 150, about 100, about 50, about 40, about 45, about 30, about 25, about 20, or about 15 seconds when an intein N-terminal domain and C-terminal domain are mixed in equimolar concentrations. In some embodiments, the trans-splicing reaction rate constant is at least about 0.5× 10−1 s−1, 1×10−1 s−1, 1.5×10−1 s−1, 0.5×10−2 s−1, about 1×10−2 s−1, about 1.5×10−2 s−1, about 2.0×10−2 s−1, about 2.5×10−2 s−1, or about 3×10−2 s−1 when an intein N-terminal domain and C-terminal domain are mixed in equimolar concentrations. In addition, the reaction rate half life can be less than about 150, about 100, about 50, about 40, about 45, about 30, about 25, about 20, or about 15 seconds when an intein N-terminal domain and C-terminal domain are mixed in equimolar concentrations. In some embodiments, the C-cleavage reaction rate constant is at least about 1×10−4 s−1, 3×10−4 s−1, 6×10−4 s−1, 9×10−4 s−1 1×10−5 s−1, about 3×10−5 s−1, about 6×10−5 s−1, or about 9×10−5 s−1, when an intein N-terminal domain and C-terminal domain are mixed in equimolar concentrations. In addition, the reaction rate half life can be less than about 150, about 100, about 50, about 40, about 45, about 30, about 25, about 20, or about 15 minutes when an intein N-terminal domain and C-terminal domain are mixed in equimolar concentrations (el C cleavage es mas lento)

In some embodiments, the reaction results in a yield at least about 50%, at least about 55%, at least about 60%, at least about 65%, of at least about 70%, at least about 75%, at least about 80%, at least about 85%, at least about 90%, at least about 95% when an intein N-terminal domain and C-terminal domain are mixed in equimolar concentrations. In some embodiments, the reaction results in a yield of at least about 80%, at least about 85%, at least about 90%, at least about 95% within 5 minutes when an intein N-terminal domain and C-terminal domain are mixed in equimolar concentrations. In some embodiments, the reactions results in a yield of about 75 to about 80%, 80% to about 85%, 85% to about 90%, or about 90 to 95% within 5 minutes when an intein N-terminal domain and C-terminal domain are mixed in equimolar concentrations.

In some embodiments, an intein reaction (e.g., cleavage, linkage (splicing), cyclization) can be initiated by contacting a fusion protein comprising an intein N-terminal domain and, optionally, a heterologous polypeptide with a fusion protein comprising an intein C-terminal domain and, optionally a heterologous polypeptide. In other embodiments, an intein reaction can be initiated by shifting the conditions, e.g., the temperature or pH, in which a split intein fusion protein or combination of split intein fusion proteins is incubated. In some embodiments, a C-terminal cleavage is initiated by a pH or temperature shift.

In some embodiments, an intein reaction is initiated by contacting fusion proteins with DTT or another strong nucleophile. In some embodiments, DTT is used to enhance a reaction. In some embodiments, an N-terminal cleavage is initiated by a strong nucleophile, e.g., DTT.

Another manner of inducing protein splicing or cleavage is by contact with a peptide or peptidomimetic agent that activates splicing or cleavage. Another manner of inducing protein splicing or cleavage is by removal of a peptide or peptidomimetic agent that blocks or inhibits splicing or cleavage.

In some embodiments, the fusion protein can be attached to a resin, e.g., for the purpose of protein separation or purification such as those provided, for example, in Lu et al., *Journal of Chromatography A* 1218: 2553-2560 (2011) and Elleuche and Poggeler, *Appl. Microbiol. Biotechnol* 87:479-489 (2010), which are herein incorporated by reference. In addition, a fusion protein can be in solution, bound to affinity beads or column, anchored to a cell membrane or phage surface. Affinity binders can include His-tags, chitin binding domains, a maltose binding protein, or a glutathione-S-transferase, for example, The fusion protein can be inside or outside a cell.

In some embodiments, intein reactions can be used in protein purification, (e.g., using chromatographic tags or non-chromatographic tags and/or in large-scale processes), in protein circularization, in protein polymerization, and in selenoprotein production, for example as described in Elleuche and Poggeler, *Appl. Microbiol. Biotechnol* 87:479-489 (2010), and Evans T. et al., *Biopolymers* 51:333-342 (1999), which are herein incorporated by reference in their entireties. The high efficiency of the inteins provided herein makes them particular amenable to large-scale industrial applications.

In some embodiments, an intein reaction can be used to produce a target polypeptide. The target polypeptide can be a fusion polypeptide containing two sequences that were previously unlinked. The target polypeptide can also be a polypeptide that is cleaved from a sequence it was previously linked to.

Multiple splicing reactions can be performed in tandem and in any order to arrange and rearrange polypeptide sequences or to join multiple or different polypeptides as desired.

VI. Vectors for the Generation of Intein Fusion Proteins

The invention also provides vectors suitable for generation of intein fusion proteins which comprise a polynucleotide encoding an intein domain and one or more cloning sites which allow the insertion a polynucleotide encoding a heterologous polypeptide in a position which results in the expression of a fusion protein comprising the intein domain and the heterologous polypeptide.

Therefore, in another aspect, the invention relates to a vector which comprises a polynucleotide encoding an intein domain at least 75% identical to a sequence selected from the group consisting of SEQ ID NOs: 7, 16, 24, 38 and 65 and at least a cloning site downstream of said polynucleotide which allows the cloning of a polynucleotide of interest such that a polynucleotide is formed which encodes a fusion protein comprising the intein domain and the polypeptide encoded by the polynucleotide of interest.

In one embodiment, the polynucleotide encoding an intein domain showing at least 75% identical to a sequence selected from the group consisting of SEQ ID NOs: 7, 16, 24, 38 and 65 encodes an intein domain wherein the last amino acid is glutamine or asparagines. In another embodiment, the polynucleotide encoding an intein domain showing at least 75% identical to a sequence selected from the group consisting of SEQ ID NOs: 7, 16, 24, 38 and 65 encodes an intein domain wherein the last amino acid of the intein domain is an amino acid other than asparagine or glutamine. In another embodiment, the vector further comprises a polynucleotide encoding a polypeptide which forms a linker peptide between the intein domain and the polypeptide encoded by the heterologous peptide. In a preferred embodiment, when the polynucleotide encoding the intein domain showing at least 75% identical to a sequence selected from the group consisting of SEQ ID NOs: 7, 16, 24, 38 and 65 encodes an intein domain wherein the last amino acid of the intein domain is an amino acid other than asparagines or glutamine, then the polynucleotide encodes a linker region wherein the first amino acid of said linker is an amino acid other than serine, threonine or serine.

In another aspect, the invention relates to a vector which comprises a polynucleotide encoding an intein domain at least 75% identical to a sequence selected from the group consisting of SEQ ID NOs: 3, 12, 20, 34 and 64 and at least a cloning site upstream of said polynucleotide which allows the cloning of a polynucleotide of interest such that a polynucleoptide is formed which encodes a fusion protein comprising the polypeptide encoded by the polynucleotide of interest and the intein domain.

In one embodiment, the polynucleotide encoding an intein domain showing at least 75% identical to a sequence selected from the group consisting of SEQ ID NOs: 3, 12, 20, 34 and 64 encodes an intein domain wherein the first amino acid is serine or cysteine. In another embodiment, the polynucleotide encoding an intein domain showing at least 75% identical to a sequence selected from the group consisting of SEQ ID NOs: 7, 16, 24, 38 and 65 encodes an intein domain wherein the first amino acid of the intein domain is an amino acid other than serine or cysteine.

In another embodiment, the invention relates to a vector which is useful for cloning a polynucleotide encoding a protein of interest and producing said polypeptide which can be cyclized. Thus the invention relates to a vector comprises a polynucleotide encoding a first intein domain at least 75% identical to a sequence selected from the group consisting of SEQ ID NOs: 7, 16, 24, 38 and 65, at least a cloning site downstream of said polynucleotide which allows the cloning of a polynucleotide of interest, and a polynucleotide downstream of the cloning site, encoding a second intein domain at least 75% identical to a sequence selected from the group consisting of SEQ ID NOs: 3, 12, 20, 34 and 64, such that a polynucleotide is formed which encodes a fusion protein comprising the polypeptide encoded by the polynucleotide of interest and the first and second intein domains.

In a preferred embodiment, the last amino acid of the first intein domain is glutamine or asparagines. In another embodiment, the penultimate amino acid of the first intein domain is histidine. In yet another embodiment, the first amino acid of the second intein domain is serine or cysteine.

In one embodiment, the invention relates to a vector which is useful for preparing fusion proteins comprising the N-terminal and C-terminal domains and two regions of a polypeptide which are to be connected by a transplicing reaction between both intein domains. Thus, in another aspect, the invention relates to a vector which comprises:
  i. a polynucleotide encoding a first intein domain at least 75% identical to a sequence selected from the group consisting of SEQ ID NOs: 7, 16, 24, 38 and 65,
  ii. a first cloning site downstream of said polynucleotide encoding a first intein domain,
  iii. a polynucleotide encoding a second intein domain at least 75% identical to a sequence selected from the group consisting of SEQ ID NOs: 3, 12, 20, 34 and 64 and
  iv. a second cloning site upstream of said polynucleotide encoding a second intein domain,
wherein the first cloning site allows the cloning of a first polynucleotide of interest and the second cloning site allows the cloning of a second polynucleotide of interest such that a polynucleotide is formed which encodes a fusion protein comprising, in said order, the polypeptide encoded by the second polynucleotide of interest, the second intein domain, the first intein domain and the polypeptide encoded by the second polynucleotide of interest and wherein
  a. if the first intein domain is at least 75% identical to SEQ ID NO:7, then the second intein domain is at least 75% identical to SEQ ID NO:3;
  b. if the first intein domain is at least 75% identical to SEQ ID NO:16 then the second intein domain is at least 75% identical to SEQ ID NO:12;
  c. if the first intein domain is at least 75% identical to SEQ ID NO:24, then the second intein domain is at least 75% identical to SEQ ID NO:20;
  d. if the first intein domain is at least 75% identical to SEQ ID NO:38, then the second intein domain is at least 75% identical to SEQ ID NO:34 or
  e. if the first intein domain is at least 75% identical to SEQ ID NO:65, then the second intein domain is at least 75% identical to SEQ ID NO:64.

In another embodiment, the vector further comprises a polynucleotide encoding a first peptide linker connecting the second intein domain and the polypeptide encoded by the second polynucleotide of interest and/or further comprising a polynucleotide encoding a second peptide linker connecting the first intein domain and the polypeptide encoded by the first polynucleotide of interest.

In another embodiment, the first amino acid of the second intein domain is cysteine or serine, wherein the last amino acid of the first intein domain is glutamine or asparagine, wherein the penultimate amino acid of first the intein domain is histidine and/or wherein the first amino acid of the second polypeptide of interest or of the first peptide linker is cysteine, serine or threonine.

As used in this invention, the term "vector" refers to a vehicle whereby a polynucleotide or a DNA molecule may be manipulated or introduced into a cell. The vector may be a linear or circular polynucleotide, or it may be a larger-size polynucleotide or any other type of construct, such as DNA or RNA from a viral genome, a virion or any other biological construct that allows for the manipulation of DNA or the introduction thereof into the cell. It is understood that the expressions "recombinant vector" and "recombinant system" may be used interchangeably with the term "vector". Those skilled in the art will note that there is no limitation in terms of the type of vector that may be used, since said vector may be a cloning vector suitable for propagation and to obtain the adequate polynucleotides or gene constructs or expression vectors in different heterologous organisms suitable for the purification of the fusion proteins. Thus, suitable vectors in accordance with this invention include expression vectors in prokaryotes, such as pUC18, pUC19, Bluescript and the derivatives thereof, mp18, mp19, pBR322, pMB9, CoIE1, pCR1, RP4, phages and "shuttle" vectors, such as pSA3 and pAT28, expression vectors in yeasts, such as vectors of the 2-micron plasmid type, integration plasmids, YEP vectors, centromere plasmids and similar ones, expression vectors in insect cells, such as the vectors in the pAC series and the pVL series, expression vectors in plants, such as vectors from the pIBI, pEarleyGate, pAVA, pCAMBIA, pGSA, pGWB, pMDC, pMY, pORE series and similar ones, and expression vectors in higher eukaryotic cells based on viral vectors (adenoviruses, viruses associated with adenoviruses, as well as retroviruses and lentiviruses) and non-viral vectors, such as pSilencer 4.1-CMV (Ambion), pcDNA3, pcDNA3.1/hyg, pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1.

In a preferred form of embodiment, the vector additionally comprises, at the 3' position with respect to the polynucleotide encoding the intein domain one or several sites that allow for the cloning of polynucleotides encoding an heterologous polypeptide. Preferably, the cloning sites are grouped so as to form a multiple cloning site, as they frequently appear in cloning vectors. Thus, the term "multiple cloning site", as used in this invention, refers to a nucleic acid sequence that comprises a series of two or more restriction endonuclease target sequences that are located close to one another. Multiple cloning sites include restriction endonuclease targets which allow for the insertion of fragments with blunt ends, sticky 5'-ends or sticky 3'-ends. The insertion of polynucleotides of interest is performed using standard molecular biology methods, as described, for example, by Sambrook et al. (Sambrook et al. Molecular Cloning: A Laboratory Manual, Cold Spring Harbour Laboratory Press, 1989) and/or Ausubel et al. (Current Protocols in Molecular Biology, Greene Pub. Associates and Wiley-Interscience (1988, including all updates until present).

As will be apparent to the skilled artisan from the description herein, the present disclosure is useful for producing expression constructs, i.e., in which nucleic acids are operably linked to suitable promoters.

Cell free expression systems are contemplated by the present disclosure. For example, a nucleic acid is operably linked to a suitable promoter, e.g., a T7 promoter, and the resulting expression construct exposed to conditions sufficient for transcription and translation. Typical expression vectors for in vitro expression or cell-free expression have been described and include, but are not limited to, the TNT T7 and TNT T3 systems (Promega), the pEXP1-DEST and pEXP2-DEST vectors (Invitrogen).

Many vectors for expression in cells are available. The vector components generally include, but are not limited to, one or more of the following: a signal sequence, a sequences encoding a polypeptide(s), an enhancer element, a promoter, and a transcription termination sequence. The skilled artisan will be aware of suitable sequences for expression of a protein. For example, exemplary signal sequences include prokaryotic secretion signals (e.g., pelB, alkaline phosphatase, penicillinase, Ipp, or heat-stable entero toxin II), yeast secretion signals (e.g., invertase leader, a factor leader, or acid phosphatase leader) or mammalian secretion signals (e.g., herpes simplex gD signal).

Exemplary promoters include those active in prokaryotes (e.g., phoA promoter, beta -lactamase and lactose promoter systems, alkaline phosphatase, a tryptophan (trp) promoter system, and hybrid promoters such as the tac promoter). These promoter are useful for expression in prokaryotes including eubacteria, such as Gram-negative or Gram-positive organisms, for example, Enterobacteriaceae such as *Escherichia*, e.g., *E. coli*, *Enterobacter, Erwinia, Klebsiella, Proteus, Salmonella*, e.g., *Salmonella typhimurium, Serratia*, e.g., *Serratia marcescans*, and *Shigella*, as well as *Bacilli* such as *B. subtilis* and *B. licheniformis, Pseudomonas* such as *P. aeruginosa*, and *Streptomyces*. In one example, the host is *E. coli*. One preferred *E. coli* cloning host is *E. coli* 294 (ATCC 31,446), although other strains such as *E. coli* B, *E. coli* X 1776 (ATCC 31,537), and *E. coli* W3110 (ATCC 27,325), DH5a or DH1OB are suitable.

Exemplary promoters active in mammalian cells include cytomegalovirus immediate early promoter (CMV-IE), human elongation factor 1-oc promoter (EF1), small nuclear RNA promoters (U1a and U1b), a-myosm heavy chain promoter, Simian virus 40 promoter (SV40), Rous sarcoma virus promoter (RSV), Adenovirus major late promoter, beta -actin promoter; hybrid regulator}' element comprising a CMV enhancer/ beta-actin promoter or an immunoglobulin promoter or active fragment thereof Examples of useful mammalian host cell lines are monkey kidney CV1 line transformed by SV40 (COS-7, ATCC CRL 1651); human embryonic kidney line (293 or 293 cells subcloned for growth in suspension culture); baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GALL promoter, the GAL4 promoter, the CUPI promoter, the PHO5 promoter, the nmt promoter, the RPR1 promoter, or the TEF1 promoter.

Typical promoters suitable for expression in insect cells include, but are not limited to, the OPEI2 promoter, the insect actin promoter isolated from *Bombyx muri*, the *Drosophila* sp. dsh promoter and the inducible metallothionein promoter. Exemplary insect cells for expression of recombinant proteins include an insect cell selected from the group comprising, BT1 -TN-5B1-4 cells, and *Spodoptera frugiperda* cells (e.g., sfl9 cells, sf21 cells). Suitable insects for the expression of the nucleic acid fragments include but are not limited to *Drosophila* sp. The use of *S. frugiperda* is also contemplated.

The vector according to the present invention may further comprise a polynucleotide encoding a marker protein. Suitable marker proteins for the present disclosure include those that confer antibiotic resistance or resistance to another toxic compound. Examples of marker proteins conferring resistance to antibiotics include neomycin phosphtransferase that phosphorylates neomycin and kanamycin, or hpt, phosphorylating hygromycin, or proteins conferring resistance to, for example, bleomycin, streptomycin, tetracycline, chloramphenicol, ampicillm, gentamycin, geneticin (G418), spectinomycin or blasticidin). In one example, the protein confers resistance to chloramphenicol. For example, the protein is a gene from *E. coli* designated CmR, e.g., as described in Nilsen et al, J. Bacteriol, 178: 3188-3193, 1996.

Alternatively, the marker protein complements an auxotrophy in a cell. For example, a eukaryotic cell lacking HPRT expression is transformed with an expression construct comprising a nucleic acid encoding HPRT. Expression of the reporter gene results in the cell being capable of growing in HAT medium, while cells that do not express the reporter gene are not capable of growing in these conditions.

Alternatively, in the case of a yeast cell, the marker protein is, for example, LEU2 or LYS2 or TRP. Such a reporter gene is capable of complementing a yeast cell that is auxotrophic for the relevant gene, and, as a consequence unable to produce the relevant amino acid.

In another example, the marker protein that is directly detectable, e.g., is a fluorescent protein. Several fluorescent reporter genes are known in the art and include, for example, those that encode green fluorescent protein (GFP), enhanced green fluorescent protein (eGFP), red shifted green fluorescent protein (RFP), cyan fluorescent protein (CFP), yellow fluorescent protein (YFP), monomeric discosoma red fluorescent protein (dsRED), or dsRED2; monomeric orange fluorescent protein or monomeric GFP from *Aequorea coerulescens*. These proteins permit selection of a cell expressing the marker protein using standard techniques, e.g., fluorescence activated cell sorting (FACS).

In a further example, a marker gene is an enzyme that catalyzes a detectable reaction. Exemplary enzymatic reporter genes include for example, beta-galactosidase, alkaline phosphatase, firefly luciferase or Renilla luciferase. For example, the expression of beta-galactosidase is detected by the addition of the substrate 5-bromo-4- chloro-3-indolyl-beta-D-galactopyranoside (x-gal), which is hydrolyzed by beta-galactosidase to produce a blue colored precipitate. Alternatively, the expression of either firefly luciferase or Renilla luciferase is detected by addition of a substrate that in the presence of the relevant protein is luminescent and is detectable, for example, using a spectrophotometer.

The cloning of the polynucleotide encoding the polypeptide of interest into the vector of the invention can be carried out using standard techniques well known to the skilled person. For example, the polynucleotide encoding the polypeptide of interest is produced using polymerase chain reaction (PCR). Methods for performing PCR are known in the art. In the case of antibodies, PCR can be used to amplify variable regions, optionally linked to one or more constant regions, e.g., form a subject or from a library or after screening a library. Primers for such amplifying nucleic acids encoding antibody regions are known in the art (e.g., as described in U.S. Pat. No. 6,096,551 and WOOO/70023). In a further example, nucleic acid can be produced/isolated using restriction endonuclease digestion according to standard methods in the art.

Methods for linking nucleic acids will be apparent to the skilled artisan and described, for example, in Sambrook et al. Molecular Cloning: A Laboratory Manual, Cold Spring Harbour Laboratory Press, 1989 and/or Ausubel et al. (editors), Current Protocols in Molecular Biology, Greene Pub. Associates and Wiley-Interscience (1988, including all updates until present). In one example, the method makes use of a hgase, e.g., T4 DNA ligase. to link nucleic acids.

In one exemplary form of the disclosure, ligase independent cloning is used to link nucleic acids.

In one form of ligase independent cloning, complementary single stranded regions are included in two nucleic acids to be linked. These nucleic acids are then hybridized to one another and the resulting nucleic acid is transformed into a cell, in which endogenous enzymes repair any remaining gap and form a single contiguous nucleic acid.

In another form of ligase independent cloning, one or more enzymes are used to enhance formation of a single nucleic acid molecule. For example, U.S. Pat. No. 7,575,860 describes a technique in which a polymerase having 3'-5' endonuclease activity (e.g., from Vaccinia virus) is used to link the two nucleic acids. For example, the nucleic acids to be linked comprise regions that are substantially identical or are identical. These regions can be between 5 to 50 nucleotides in length, e.g., about 12 to 15 nucleotides in length, such as about 15 nucleotides in length. The nucleic acids to be linked are then contacted with a polymerase having 3 '-5' exonuclease activity. Exemplary polymerases include vaccinia DNA polymerase, T4 DNA polymerase and the Klenow fragment of *E. Coli* DNA polymerase I. In one example, the nucleic acid is additionally contacted with a single strand DNA binding protein, such as, vaccinia and *E. coli* single strand binding proteins, Herpes simplex virus ICP8 protein, and yeast and human replication Protein A (eg. yRPA and hRPA). Kits for performing this type of ligase independent cloning are commercially available from Clontech under the trademark In-Fusion(R).

Additional ligase independent cloning methods are known in the art and include, for example, ligation independent cloning (LIC; e.g., as described in Aslanidis et al, Nucl. Acids Res., 18: 6069), T7 exonuclease-mediated cloning (U.S. Pat. No. 5,580,759), hetero- stagger PCR-based cloning (Liu et al, Nucleic Acids Res 24: 2458-2459, 1996), uracil- excision based cloning (Nisson et al, PCR Meth. Appl 7: 120-123, 1991), phosphorothioate-based ligase-independent cloning (e.g., as described by Blanusa et al, Anal. Biochem, 406: 141-146, 2010).

The resulting nucleic acid can then be introduced into cells using a standard method in the art, e.g., as discussed below.

In one example, recombination is used to link nucleic acids. For example, two nucleic acids to be linked both comprise a region (e.g., 100 nucleotides or 50 nucleotides or 20 nucleotides or 10 nucleotides in length) that are identical or substantially identical. The nucleic acids are then introduced into cells capable of homologous recombination and cells in which homologous recombination has occurred are selected, e.g., by selecting for expression of the marker protein.

\* \* \*

The invention is herein described by way of the following examples which are intended as merely illustrative and not limitative of the scope of the invention.

EXAMPLES

Example 1

Trans-Splicing Activity of Gp41.1, Gp41.8, NrdJ1, IMPDH1 Split Inteins Compared with Npu DnaE In vitro trans-splicing reactions were performed with constructs containing split intein sequences of Gp41.1 (G1), Gp41.8 (G8), NrdJl(N1), and IMPDH1(I1). The split intein Npu DnaE (DE), which has been characterized as a robust and high-yielding intein (Zettler J. et al, *FEBS Letters* 583:909-914 (2009)), was selected as a control. The numbering, abbreviation, sequence and molecular weight of these inteins are presented in Table 3 below. As shown in FIG. 1A, the N-terminal fragment of each split intein construct consisted of (i) a Streptagll (ST) purification tag, (ii) the phage protein bacteriophage λ head protein D (gpD), which can increase protein solubility, (iii) the five natural flanking amino acids belonging to the N-extein ($E^N$), (iv) the N-terminus split intein fragment ($I^N$), and (v) the hexa-histidine purification tag ($H_6$). The C-terminal fragment of each split intein construct is also shown in Figure 1A and consisted of (i) the C-terminus split intein fragment ($I^C$), (ii) the five natural flanking amino acids belonging to the C-extein ($E^C$), (iii) thioredoxin, which can increase protein solubility and help protein folding, and (iv) the hexa-histidine purification tag ($H_6$).

All these fusion proteins were expressed independently in *E. coli*, and the soluble forms were purified. Equimolar concentrations (5-15 μM) of N- and C-terminal split intein pairs were mixed ($G1^N+G1^C+$, $G8^N+G8^C$, $N1^N+N1^C$, and $I^N+I^C$). After incubation at 25° C., the trans-splicing reaction was stopped at different time points by boiling for 5 minutes immediately after the addition of SDS-sample buffer. The trans-splicing reaction is summarized in FIG. 1A.

TABLE 3

Summary of split inteins numbering, abbreviation, sequence and molecular weights of the fusion proteins containing the split inteins. Streptag II and His-sequences are underlined. The linker between the split inteins and the proteins of interest (gpD or Trx) is indicated in bold and italics. The extein sequence within the linker is enclosed by brackets.

| Abbr. | Protein sequence | MW kDa |
|---|---|---|
| $G1^N$ | MAS<u>WSHPQFEKAS</u>-gpD-*GS[TRSGY]*-Gp41.1$^N$-GG<u>HHHHHH</u> (SEQ ID NO: 2) | 24.2 |
| $G8^N$ | MAS<u>WSHPQFEKAS</u>-gpD-*GS[SQLNR]*-Gp41.8$^N$-GG<u>HHHHHH</u> (SEQ ID NO: 11) | 24.2 |
| $N1^N$ | MAS<u>WSHPQFEKAS</u>-gpD-*GS[GTNPC]*-NrdJ1$^N$-GG<u>HHHHHH</u> (SEQ ID NO: 19) | 26.2 |
| $I1^N$ | MAS<u>WSHPQFEKAS</u>-gpD-*GS[GIGGG]*-IMPDH1$^N$-GG<u>HHHHHH</u> (SEQ ID NO: 33) | 25.8 |
| $DE^N$ | MAS<u>WSHPQFEKAS</u>-gpD-*GS*-DnaE$^N$ (SEQ ID NO: 27) | 24.7 |
| $G1^C$ | Gp41.1$^C$-*[SSSDV]GT*-Trx-EFRS<u>HHHHHH</u> (SEQ ID NO: 6) | 18.8 |
| $G8^C$ | Gp41.8$^C$-*[SAVEE]GT*-Trx-EFRS<u>HHHHHH</u> (SEQ ID NO: 15) | 19.1 |
| $N1^C$ | NrdJ1$^C$-*[SEIVL]GT*-Trx-EFRS<u>HHHHHH</u> (SEQ ID NO: 23) | 18.6 |
| $I1^C$ | IMPDH1$^C$-*[SICST]GT*-Trx-EFRS<u>HHHHHH</u> (SEQ ID NO: 37) | 18.6 |
| $DE^C$ | DnaE$^C$-*[CFN]GT*-Trx-EFRS<u>HHHHHH</u> (SEQ ID NO: 30) | 17.9 |
| $G1^{N(C1A)}$ | MAS<u>WSHPQFEKAS</u>-gpD-*GS[TRSGY]*-Gp41.1$^{N(C1a)}$-GG<u>HHHHHH</u> (SEQ ID NO: 56) | 24.2 |
| $G8^{N(C1A)}$ | MAS<u>WSHPQFEKAS</u>-gpD-*GS[SQLNR]*-Gp41.8$^{N(C1A)}$-GG<u>HHHHHH</u> (SEQ ID NO: 57) | 24.2 |
| $N1^{N(C1A)}$ | MAS<u>WSHPQFEKAS</u>-gpD-*GS[GTNPC]*-NrdJ1$^{N(C1A)}$-GG<u>HHHHHH</u> (SEQ ID NO: 58) | 26.2 |
| $I1^{N(C1A)}$ | MAS<u>WSHPQFEKAS</u>-gpD-*GS[GIGGG]*-IMPDH1$^{N(C1A)}$-GG<u>HHHHHH</u> (SEQ ID NO: 59) | 25.8 |
| $G1^{C(\Delta ext)}$ | Gp41.1$^C$-*GT*-Trx-EFRS<u>HHHHHH</u> (SEQ ID NO: 60) | 18.3 |
| $G1^{C(S)}$ | Gp41.1C-*[S]GT*Trx-EFRS<u>HHHHHH</u> (SEQ ID NO: 66) | 18.3 |
| $G8^{C(\Delta ext)}$ | Gp41-8$^C$-*GT*-Trx-EFRS<u>HHHHHH</u> (SEQ ID NO: 61) | 18.6 |
| $N1^{C(\Delta ext)}$ | NrdJ-1$^C$-*GT*-Trx-EFRS<u>HHHHHH</u> (SEQ ID NO: 62) | 18.2 |
| $I1^{C(\Delta ext)}$ | IMPDH-1$^C$-*GT*-Trx-EFRS<u>HHHHHH</u> (SEQ ID NO: 63) | 18.1 |
| $G1^{N(\Delta ext)}$ | MAS<u>WSHPQFEKAS</u>-gpD-*GS*-Gp41.1$^N$-GG<u>HHHHHH</u> (SEQ ID NO: 67) | 24.2 |
| $G1^{C(N \to A)}$ | Gp41.1$^{C(N \to A)}$-*[SSSDV]GT*-Trx-EFRS<u>HHHHHH</u> (SEQ ID NO: 68) | 18.8 |
| $G8^{C(N \to A)}$ | Gp41.8$^{C(N \to A)}$-*[SAVEE]GT*-Trx-EFRS<u>HHHHHH</u> (SEQ ID NO: 69) | 19.1 |
| $N1^{C(N \to A)}$ | NrdJ1$^{C(N \to A)}$-*[SEIVL]GT*-Trx-EFRS<u>HHHHHH</u> (SEQ ID NO: 70) | 18.6 |
| $I1^{C(N \to A)}$ | IMPDH1$^{C(N \to A)}$-*[SICST]GT*-Trx-EFRS<u>HHHHHH</u> (SEQ ID NO: 71) | 18.6 |

TABLE 3-continued

Summary of split inteins numbering, abbreviation, sequence and molecular weights of the fusion proteins containing the split inteins. Streptag II and His-sequences are underlined. The linker between the split inteins and the proteins of interest (gpD or Trx) is indicated in bold and italics. The extein sequence within the linker is enclosed by brackets.

| Abbr. | Protein sequence | MW kDa |
|---|---|---|
| G1$^{C(N/S \to A)}$ | Gp41.1$^{C(N/S \to A)}$-**[ASSDV]*GT***-Trx-EFRS<u>HHHHHH</u> (SEQ ID NO: 72) | 18.8 |
| G8$^{C(N/S \to A)}$ | Gp41.8$^{C(N/S \to A)}$-**[AAVEE]*GT***-Trx-EFRS<u>HHHHHH</u> (SEQ ID NO: 73) | 19.1 |
| N1$^{C(N/S \to A)}$ | NrdJ1$^{C(N/S \to A)}$-**[AEIVL]*GT***-Trx-EFRS<u>HHHHHH</u> (SEQ ID NO: 74) | 18.6 |
| I1$^{C(N/S \to A)}$ | IMPDH1$^{C(N/S \to A)}$-**[AICST]*GT***-Trx-EFRS<u>HHHHHH</u> (SEQ ID NO: 75) | 18.6 |

P = Protein number, Abbr = Abbreviation, MW = molecular weight, Gp41.1$^N$: N-terminal fragment of the Gp41.1 split intein (SEQ ID NO: 3), Gp41.8$^N$: N-terminal fragment of the Gp41.8 split intein (SEQ ID NO: 12), NrdJ1$^N$: N-terminal fragment of the Nrdj1 split intein (SEQ ID NO: 20), IMPDH1$^N$: N-terminal fragment of the IMPDH1 split intein (SEQ ID NO: 34), DnaE$^N$: N-terminal fragment of the DnaE split intein (SEQ ID NO: 28), Gp41.1$^C$: C-terminal fragment of the Gp41.1 split intein (SEQ ID NO: 7), Gp41.8$^C$: C-terminal fragment of the Gp41.8 split intein (SEQ ID NO: 16), NrdJ1$^C$: C-terminal fragment of the Nrdj1 split intein (SEQ ID NO: 24), IMPDH1$^C$: C-terminal fragment of the IMPDH1 split intein (SEQ ID NO: 38), DnaE$^C$: C-terminal fragment of the DnaE split intein (SEQ ID NO: 31), Trx: *E. coli* thioredoxin (SEQ ID NO: 77); gpD: bacteriophage λ head protein D (SEQ ID NO: 76).

Experiments were performed with all four split inteins (Gp41.1 (G1), Gp41.8(G8), NrdJl(N1), and IMPDH1(I1)). Exemplary results obtained using Gp41.1 (G1) are show in FIG. 1B. The initial N- and C-terminal fragments (FIG. 1B, lane 1: F1 and F2, respectively) reacted very quickly to produce the spliced product and the N- and C-split intein side-products (FIG. 1B, lane 2-9: F3, F4, and F5, respectively). The speed of the trans-splice reaction was calculated as the rate constant "k," which is directly proportional to the speed of the trans-splice reaction. The reaction half life "$t_{1/2}$," which represents the time needed for half of the precursors (F1 or F2) in a splicing reaction to be consumed, was also calculated.

Surprisingly, all the split inteins analyzed (G1, G8, N1 and I1) were faster than the previously characterized Npu DnaE (Zettler J. et al, *FEBS Letters* 583:909-914 (2009)). In the same reaction conditions at 25° C., the G1, G8, N1 and I1 were respectively 31-, 6-, 9- and 7-fold faster than Npu DnaE, which has been characterized as an exceptional split intein having the highest rate constant reported so far (Table 4). The splicing yields demonstrated that at 5 minutes, the G1, G8, N1 and I1 have about 90% of splice product formation.

TABLE 4

Percentage of protein splicing and first order rate constants of protein trans-splicing reaction determined for split inteins.

| Intein | Temp ° C. | SP (%) | k (s$^{-1}$) | $t_{1/2}$ (s) |
|---|---|---|---|---|
| G1 | 25 | 80-90 | 5.7 × 10$^{-2}$ | 12 |
| G8 | 25 | 85-95 | 1.7 × 10$^{-2}$ | 40 |
| N1 | 25 | 85-95 | 6.2 × 10$^{-2}$ | 20 |
| I1 | 25 | 90-95 | 2.0 × 10$^{-2}$ | 34 |
| DE | 25 | 75-85 | 3.4 × 10$^{-3}$ | 180 |
| DE* | 25 | 75-85 | 3.5 × 10$^{-3}$ | 198 |

SP = splice product
*Zettler J. et al 2009. FEBS Letters 583:909-914

The splice products of G1, G8, N1 and I1 were identified by mass spectrometry LC-MS/MS (>90% sequence coverage). The molecular weights determined were consistent with the theoretical value of 27.3 kDa for all of them.

Given these outstanding properties, this group of natural split inteins seems to be a new generation of ultra-rapid splice inteins that can be used for many applications including protein engineering, cellular chemistry, cyclization, purification and others.

Example 2

Effect of the Temperature on the Trans-splicing Activity of Gp41.1

In order to test the versatility and robustness of these split inteins at different temperatures, Gp41.1 was analysed in more detail. Intein activity has been shown to be affected by temperature. Evidence of protein splicing activity mediated by naturally Ssp DnaE and semisynthetic Mtu RecA split inteins at low temperature such as 4° C. have been previously reported (Martin, D. et al. 2001. Biochemistry, 40:1393-1402 and Lew, B. et al. 1999. Biopolymers (Peptide Science), 51:355-362), but activity at less than 4° C. has, to our knowledge, not previously documented. Therefore, the activity of GP41.1 was tested at various temperatures. Purified N- and C-terminal fragments of Gp41.1 were mixed in splicing buffer at an equimolar concentration of 5 μM, and incubated at 0, 12, 25 and 37° C. The splice product formation and constant rates were determined, and the results are shown in Table 5.

Surprisingly, Gp41.1 intein was still active at 0° C. It had a k=5.5×10$^{-3}$S$^{-1}$, and after 1 hour of reaction under such extreme conditions, between 80-90% of the splice product was formed. When the same reaction was performed at 12° C., the trans-splicing speed was increased to a k=1.3×10$^{-2}$s$^{-1}$ (faster than Npu DnaE at 12° C. with a k=2.2±0.5×10$^{-3}$s$^{-1}$), and after 1 hour of reaction, between 85-90% of the splice product was formed. At 25° C., the Gp41.1 split intein exhibited a k=5.2×10$^{-2}$s$^{-1}$ (also faster than Npu DnaE at 25° C., k=3.5±0.2×10$^{-3}$s$^{-1}$) with 90-95% of splice product formation at 30 minutes.

It has also been previously shown that many split inteins, including Ssp DnaE and Mtu RecA, exhibit reduced yields and increased formation of hydrolysis side products at higher temperatures (i.e., 37° C.). Other inteins, however, such as Npu DnaE, are most active at 37° C. The Gp41.1 split intein displayed its highest rate of activity at 37° C.: k=1.1×10$^{-1}$s$^{-1}$ (faster again than the Npu DnaE at 37° C., k=1.1±0.2×10$^{-2}$s$^{-1}$). Notably, 90-95% of splice product had formed within 5 minutes. These results indicate that G1 has a wide-range (from 0 to 37° C.) temperature-tolerance.

TABLE 5

Effect of the temperature over G1 trans-splicing activity.

| Temp (° C.) | k (s$^{-1}$) | t$_{1/2}$ (s) | SP (%) |
| --- | --- | --- | --- |
| 0 | 5.5 × 10$^{-3}$ | 126 | 80-90 |
| 12 | 1.8 × 10$^{-2}$ | 39 | 80-90 |
| 25 | 5.7 × 10$^{-2}$ | 12 | 90-95 |
| 37 | 1.4 × 10$^{-1}$ | 5 | 90-95 |
| 45 | 1.8 × 10$^{-1}$ | 4 | 85-95 |
| 50 | 1.2 × 10$^{-1}$ | 6 | 85-95 |
| 55 | 8.3 × 10$^{-2}$ | 8 | 65-75 |

Interestingly, at all of the temperatures analyzed, G1 trans-splicing activity was faster than the high performing Npu DnaE split intein. At 12° C. and 25° C., G1 was 6- and 15-fold faster than Npu DnaE, and even at 37° C., where Npu DnaE displays its fastest activity, G1 had 10-fold faster activity.

Example 3

Effect of pH and Chaotropic Salt on Trans-splicing Activity

It has been shown that many split inteins including Ssp DnaE, and Mtu RecA inteins, exhibit reduced yields and increased formation of hydrolysis side products at high pH or in the presence of denaturing agents (Zettler et al., 2009. FEBS letters 583: 909-914). However, the efficiency of G1 splicing was nearly independent of pH between 6 and 9 (table 6). A decline of activity was only observed at extreme pH values such as 4 and 10. Mtu RecA, in contrast, has a much more narrow optimal splicing range of between pH 6 and 7.5 (Lew B. et al. Biopolymers. 51:355-362 (1999)). The Ssp DnaE intein exhibits a maximal trans-splicing activity at pH 7.0, but it drops off at higher pH (Martin D. et al. 2001. Biochemistry. 40:1393-1402).

TABLE 6

Effect of the pH and the presence of chaotropic salts over G1 trans-splicing activity

| pH | Chaotropic salt | SP (%) in 1 hour |
| --- | --- | --- |
| 6 | — | 80-85 |
| 7 | — | 80-85 |
|   | Urea 4M | 40-45 |
| 8 | — | 80-85 |
| 9 | — | 75-80 |

In some cases, expression of intein fusion proteins might require the presence of some denaturing agent to increase their solubility. Therefore, tolerance toward the presence of 4M urea in the splicing reaction was also determined for the Gp41.1 split intein. The results presented in table 4 show significant splicing activity in presence of a moderate concentration of urea (4M), with nearly 50% of trans-splicing activity after 1 hour of reaction with regard to the optimized conditions.

These features demonstrate the unexpected versatility and the robustness of the G1 split intein.

Example 4

Effect of the Exteins on Trans-splicing Activity

The N-extein (E$^N$) amino acids flanking the N-intein domain do not participate directly in the trans-splicing reaction, but they could have an influence in the reaction efficiency. In order to test this possibility the five amino acids of the E$^N$ from G1 (TRSGY) were deleted, and the new N-terminal fragment generated (G1$^{N(\Delta ext)}$) was incubated with the corresponding C-terminal fragment (G1$^C$) in the same conditions described in example 1. Interestingly, it was observed trans-splicing activity in the absence of E$^N$ (rate value 1.8 E−3 s$^{-1}$ and a yield 45%), demonstrating that E$^N$ from G1 split intein is not essential.

On the contrary, it has been described that the first amino acid of the C-extein is directly involved in the trans-splicing reaction mediated by inteins and split-inteins. In order to test the role of the serine located at the first position of the G1 N-extein two new G1 C-terminal fragments were generated. They comprised a C-terminal fragment where the E$^C$ domain was: (i) partially (only the serine flanking I$^N$ was maintained; G1$^{C(S)}$) or (ii) completely removed (G1$^{C(\Delta ext)}$).

The incubation of G1$^{C(S)}$ with the corresponding N-terminal fragment, either containing or lacking the E$^N$ (G1$^N$ or G1$^{N(\Delta ext)}$ respectively) resulted in an efficient trans-splicing reaction. On the contrary, when G1$^N$ or G1$^{N(\Delta ext)}$ are incubated in the presence of G1$^{C(\Delta ext)}$, no trans-splicing reaction is observed. In this specific situation, surprisingly C- and N-cleavage activity is observed. From these results, it can be concluded that a serine residue close to the I$^N$, and preferably flanking it, is necessary to ensure an efficient trans-splicing reaction.

Example 5

Effect on C-terminal Self-cleavage of the Point Mutation C1A at the I$^N$ in Gp41.1, Gp41.8, NrdJ1 and IMPDH1 Split Inteins Some inteins show independent self-cleavage activity at the N-terminus or C-terminus and require distinct amino acid residues. The mutation at Cys1 to Ala (C1A) in I$^N$ disables the cleavage at the N-terminus but not the C-terminus (heretofore referred as C-terminal self-cleavage), while mutation at the C-terminal Asn154 to Ala in I$^C$ disables cleavage at the C-terminus but not the N-terminus (Mathys, S. et al. Gene 231:1-13 (1999) and Lu et al. *J. Chromatography A.* 1218:2553-2560 (2011)). Because of this interesting property, some mutated inteins can be used as self-cleavable peptides that allow a controlled liberation of the protein of interest from fusion proteins. Thus, such mutated inteins can be used instead of expensive commercial proteases.

In all natural split inteins analyzed to date, the C1A mutation abolishes the protein splicing. The C1A mutation in the natural split inteins Npu DnaE and Ssp DnaE blocks the initial N to S-acyl shift and blocks proteins splicing, but also almost completely inhibits the C-terminal cleavage reaction (Zettler J., et al. 2009. FEBS Letters 583:909-914) and Ssp DnaE (Martin, D. et al. 2001. Biochemistry.

40:1393-1402). In addition, it has been reported that the C-terminal self-cleavage activity is inhibited up to 90% in the natural full length Pab PolII intein point mutated at S1A (Xu, M. & Perler, F. *EMBO J.* 15:5146-5153 (1996)).

In order to test the C-terminal self-cleavage activity, the mutation Cys1 to Ala (C1A) was introduced in all $I^N$ split inteins ($G1^{N(C1A)}$, $G8^{N(C1A)}$, $N1^{N(C1A)}$, and $I1^{(C1A)}$). The numbering and schematic representation of this point mutated constructs are presented in Table 3 and FIG. 2A, respectively. Purified F1 ($I^{N(C1A)}$) and F2 ($I^C$) fragments from *E. coli* homogenates were mixed at equimolar concentrations of 5-15 uM, and time course experiments were performed at 25° C. Surprisingly, in contrast to the natural split inteins Npu DnaE and Ssp DnaE, all four tested split inteins showed C-terminal self-cleavage. In all the cases, two new protein bands were observed that corresponded in size to the expected F3 (Trx-H6) and to the excised F4 ($Int^C$) fragment (FIG. 2A). The values of the yield (% CP) and the constant rate of the C-terminal cleavage reaction at 25° C. is shown in the following table.

TABLE 7

Yield of C-terminal cleavage reaction

| Intein | Temp (° C.) | k (s$^{-1}$) | t$_{1/2}$ (min) | CP (%) |
|---|---|---|---|---|
| G1 | 25 | 5.95E−04 | 19.4 | 85-95 |
| G8 | 25 | 9.50E−05 | 121.6 | 85-95 |
| N1 | 25 | 2.70E−04 | 43 | 85-95 |
| I1 | 25 | 3.65E−04 | 31.6 | 85-95 |

CP = Cleaved product

Contrary to the N-terminal extein ($E^N$), the C-terminal extein ($E^C$) participates indirectly in the C-terminal self-cleavage reaction. The $E^C$ is believed to provide a proper environment to the $I^C$ to ensure an efficient C-terminal self-cleavage reaction (Zettler J. et al, *FEBS Letters* 583: 909-914 (2009); Lu L. et al, *J. Chromatography A*. 1218: 2553-2560 (2011); Nichols N. et al. *Biochemistry.* 42:5301-5311 (2003); and Appleby et al., *JBC* 284:6194-6199 (2009)). This requirement can be an important limitation for several applications because the extein sequence will remain attached to the protein of interest after the self-cleavage reaction.

The 5 amino acids of the extein sequence ($E^C$) flanking the C-terminal split inteins were removed. The corresponding constructs ($G1^{C(\Delta ext)}$, $G8^{C(\Delta ext)}$, $N1^{C(\Delta ext)}$, and $I1^{C(\Delta ext)}$, see table 1) presented a direct junction between the $I^C$ and the Trx gene. For cloning purposes, the KpnI cleavage site was maintained, but the presence of the extra amino acids GT do not affect the analysis of the role of the exteins because they share no homology to the extein flanking sequence and can be considered as part of the Trx protein.

The F1 (gpD-$I^{N(C1A)}$) and F2 ($I_C$-Trx) fragments corresponding to Gp41.1 (G1), Gp41.8(G8), NrdJ1(N1), and IMPDH1(I1) were purified from *E. coli* homogenates and were mixed at equimolar concentrations of 5-15 μM. Time course experiments were performed at 25° C. Surprisingly, all four natural split inteins showed C-terminal self-cleavage, and two bands with a mobility consistent with F3 (Trx) and F4 ($I^C$) were observed after 3 hours of incubation (FIG. 2B). The yield (% CP) and the constant rate of the C-terminal cleavage reaction at 25° C. of G1 and N1 was determined. A comparison of Tables 4 and 5 demonstrates that the yield is very high and is independent of the presence of the five amino acids of the $E^C$. The absence of the $E^C$ fragment results in a reduction of the constant rate, but this decrease in the rate of the split intein reaction can be overcome by increasing the reaction temperature to 37 or 45° C. (Table 8). This unexpected observation suggests that these inteins can work very efficiently at high temperatures, even though these proteins do not come from thermophilic microorganisms.

Edman protein sequencing of the F3 fragments liberated in the C-terminal cleavage reaction demonstrated that the first amino acids in the F3 fragment were GT. This demonstrates that the C-terminal cleavage reaction was performed properly.

TABLE 8

Yield of C-terminal cleavage reaction

| Intein | Temp (° C.) | k (s$^{-1}$) | t$_{1/2}$ (min) | CP (%) |
|---|---|---|---|---|
| G1 | 25 | 9.00E−05 | 128 | 85-95 |
|  | 37 | 2.4E−04 | 48 | 85-95 |
|  | 45 | 5.2E−04 | 22 | 85-95 |
| N1 | 25 | 4.00E−05 | 144 | 85-95 |

CP = Cleaved product

These results demonstrate that, in contrast to Npu DnaE (Zettler J. et al, *FEBS Letters* 583:909-914 (2009)), Ssp DnaE (Nichols N. et al., *Biochemistry* 42:5301-5311 (2003)), and Ssp DnaB (Lu L. et al, *J. Chromatography A*. 1218:2553-2560 (2011)) Gp41.1 (G1), Gp41.8 (G8), NrdJ1 (N1), and IMPDH1 (I1) are able to display a C-terminal cleavage in the absence of the 5 amino acid C-extein flanking fragment ($E^C$).

In the experiments described above, it has been demonstrated that the C-cleavage can be performed in the absence of the $E^C$. Nevertheless, the influence the nature of the first amino acid after the $I^C$ has on the C-cleavage efficiency was not analysed. For C-cleavage applications, it is preferred that the liberated protein from the cleaved fusion protein do not contain any extra amino acid on its N-terminal end. In order to determine whether the G1 split intein was able to produce a "clean" cleavage independently of the fist amino acid of the protein of interest, a new battery of constructs were performed. In these constructs, the first amino acid of the Trx protein was mutated to all amino acid natural variants, and then cloned directly to the C-terminal domain of G1. Surprisingly, all the variants showed a significant C-cleavage activity.

The yield, constant rate and t(1/2) determined for each construct are summarized in the Table 9.

TABLE 9

Summary of the yield and kinetic parameters (k and t(½)) of C-Cleavage for several G1 constructs.

| | C-terminal Cleavage | | |
|---|---|---|---|
| Residue* | Yield (%) | k s$^{-1}$ | t(½) min |
| Met | 85.63 | 8.70E-04 | 13.28 |
| Cys | 83.62 | 6.83E-04 | 16.91 |
| Thr | 87.51 | 5.73E-04 | 20.15 |
| Arg | 87.32 | 5.10E-04 | 22.65 |
| Lys | 86.71 | 5.10E-04 | 22.65 |
| Ser** | 89.40 | 4.83E-04 | 23.90 |
| Gln | 88.85 | 4.70E-04 | 24.58 |
| His | 71.13 | 4.47E-04 | 25.86 |
| Ala | 75.82 | 3.57E-04 | 32.39 |
| Tyr | 91.34 | 3.30E-04 | 35.01 |
| Phe | 72.60 | 3.07E-04 | 37.67 |

TABLE 9-continued

Summary of the yield and kinetic parameters (k and t(½)) of C-Cleavage for several G1 constructs.

| | C-terminal Cleavage | | |
|---|---|---|---|
| Residue* | Yield (%) | k s$^{-1}$ | t(½) min |
| Asn | 71.20 | 2.87E-04 | 40.30 |
| Trp | 94.12 | 2.80E-04 | 41.26 |
| Val | 86.68 | 2.73E-04 | 42.27 |
| Leu | 69.32 | 2.73E-04 | 42.27 |
| Asp | 68.61 | 2.47E-04 | 46.83 |
| Ile | 88.37 | 1.73E-04 | 66.65 |
| Gly | 75.18 | 1.37E-04 | 84.53 |
| Glu | 86.18 | 1.27E-04 | 91.20 |
| Pro | 57.82 | 6.00E-05 | 192.54 |

*Corresponds to the first residue after the IC.
**Serine is the natural amino acid found in G1

Example 6

N-terminal Self-cleavage with Gp41.1, Gp41.8, NrdJ1 and IMPDH1 Split Inteins

It has been described for several inteins and split inteins that blocking of C-terminal cleavage by means of the mutation of the Asn just upstream from the extein still allows the N-cleavage to occur. This mutation was introduced in the $I_C$ domain of Gp41.1, Gp41.8, NrdJ1 and IMPDH1 split inteins (G1$^{C(N \to A)}$, G8$^{C(N \to A)}$, N1$^{C(N \to A)}$ and I1$^{C(N \to A)}$ respectively) by replacing the Asn just upstream from the extein by an Ala. As previously described these fusion proteins were produced in E coli, purified and incubated afterwards with equivalent amounts of the corresponding counterparts G1$^N$, G8$^N$, N1$^N$ and I1$^N$, essentially as described previously. Surprisingly, the N-terminal self-cleavage reaction was highly inefficient, as can be concluded by the observation that only one of the two expected N-terminal self-cleavage products was clearly observed in SDS-PAGE gels (I$^N$-H6). The second expected product corresponding to the ST-gpD-E$^N$ was also observed, but as a very faint band demonstrating that the N-terminal self-cleavage reaction was very inefficient. Moreover, an intermediary product probably corresponding to the C-terminal fragment (G1$^{C(N \to A)}$, G8$^{C(N \to A)}$, N1$^{C(N \to A)}$ or I1$^{C(N \to A)}$ bound to the ST-gpD-E$^N$ was observed as a major by-product.

In order to increase the efficiency of the N-cleavage, a second round of point mutations on all the single mutants previously assayed (G1$^{C(N \to A)}$, G8$^{C(N \to A)}$, N1$^{C(N \to A)}$, and I1$^{C(N \to A)}$) was performed. The first Ser residue of the E$^C$ was mutated to Ala. The new double mutants generated (G1$^{C(N/S \to A)}$, G8$^{C(N/S \to A)}$, N1$^{C(N/S \to A)}$ and I1$^{C(N/S \to A)}$) were expressed in E coli, and the purified proteins were incubated at 25° C. with an equivalent concentration of the corresponding counterpart (G1$^N$, G8$^N$, N1$^N$ and I1$^N$, respectively). In this case, the analysis by SDS-PAGE showed as the N-terminal self-cleavage occurred very efficiently. In conclusion, the mutation of the Ser residue at the first position of the E$^C$ combined with the mutation at the last Asn residue of the I$^C$ allows an efficient N-terminal cleavage. For instance, the incubation of the purified G1$^{C(N/S \to A)}$ with the G1$^N$, resulted in a N-terminal cleavage rate of 5.7 E-4 s$^{-1}$ and a yield of 70%.

* * *

All publications, patents, patent applications, internet sites, and accession numbers/database sequences (including both polynucleotide and polypeptide sequences) cited herein are hereby incorporated by reference in their entirety for all purposes to the same extent as if each individual publication, patent, patent application, internet site, or accession number/database sequence were specifically and individually indicated to be so incorporated by reference.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A fusion protein comprising (i) an intein domain having a sequence selected from the group consisting of SEQ ID NOs: 7, 16, 24, and 38 and (ii) a heterologous polypeptide, wherein the heterologous polypeptide is C-terminal to the intein domain and wherein said intein domain is functional for trans-splicing reactions and/or C-terminal cleavage reaction and allows faster trans-splicing reaction than the sequence shown in SEQ ID NO: 31.

2. The fusion protein of claim 1 wherein the last amino acid of the intein domain is glutamine or asparagine.

3. The fusion protein of claim 2 wherein the first amino acid of the heterologous polypeptide is serine, cysteine or threonine.

4. The fusion protein of claim 1 wherein the last amino acid of the intein domain is an amino acid other than asparagine or glutamine and wherein the first amino acid of the heterologous polypeptide is an amino acid other than serine, cysteine, or threonine.

5. A fusion protein comprising (i) an intein domain having a sequence selected from the group consisting of SEQ ID NOs: 3, 12, 20, and 34 and (ii) a heterologous polypeptide, wherein the heterologous polypeptide is N-terminal to the intein domain and wherein said intein domain is functional for trans-splicing reactions and/or N-terminal cleavage reaction and allows faster trans-splicing reaction than the sequence shown in SEQ ID NO: 28.

6. The fusion protein of claim 5, wherein the first amino acid of the intein domain is a serine or cysteine.

7. The fusion protein of claim 5 wherein the first amino acid of the intein domain is an amino acid other than serine or cysteine.

8. A composition or kit-of-parts comprising a first component and a second component wherein
   (i) the first component is the fusion protein of claim 1 and
   (ii) the second component is selected from the group consisting of a N-terminal intein domain and a fusion protein comprising (a) an N-terminal intein domain having a sequence selected from the group consisting of SEQ ID NOs: 3, 12, 20, and 34 and (b) a heterologous polypeptide, wherein the heterologous polypeptide is N-terminal to the N-terminal intein domain, and wherein the first amino acid of the intein domain is an amino acid other than serine or cysteine;
wherein
  a. the intein domain from the first component is SEQ ID NO:7 and the intein domain from the second component is SEQ ID NO:3;
  b. the intein domain from the first component is SEQ ID NO:16 and the intein domain from the second component is SEQ ID NO:12;
  c. the intein domain from the first component is SEQ ID NO:24 and the intein domain from the second component is SEQ ID NO:20; or
  d. the intein domain from the first component is SEQ ID NO:38 and the intein domain from the second component is SEQ ID NO:34.

9. A composition or kit-of-parts comprising a first component and a second component wherein
  (i) the first component is the fusion protein of claim 5 and
  (ii) the second component is selected from the group consisting of a C-terminal intein domain and a fusion protein comprising (a) a C-terminal intein domain having a sequence selected from the group consisting of SEQ ID NOs: 7, 16, 24, and 38 and (b) a heterologous polypeptide, wherein the heterologous polypeptide is C-terminal to the intein domain, and wherein the last amino acid of the C-terminal intein domain is an amino acid other than asparagine or glutamine and wherein the first amino acid of the heterologous polypeptide is an amino acid other than serine, cysteine, or threonine;
wherein
  a. the intein domain from the first component is SEQ ID NO:3 and the intein domain from the second component is SEQ ID NO:7;
  b. the intein domain from the first component is SEQ ID NO:12 and the intein domain from the second component is SEQ ID NO:16;
  c. the intein domain from the first component is SEQ ID NO:20 and the intein domain from the second component is SEQ ID NO:24; or
  d. the intein domain from the first component is SEQ ID NO:34 and the intein domain from the second component is SEQ ID NO:38.

10. A composition or kit-of-parts comprising a first component and a second component wherein (i) the first component is the fusion protein of claim 1 and (ii) the second component is a fusion protein comprising (a) an intein domain having a sequence selected from the group consisting of SEQ ID NOs: 3, 12, 20, and 34 and (b) a heterologous polypeptide, wherein the heterologous polypeptide is N-terminal to the intein domain, wherein
  a. the intein domain from the first component is SEQ ID NO:7 and the intein domain from the second component is SEQ ID NO:3;
  b. the intein domain from the first component is SEQ ID NO:16 and the intein domain from the second component is SEQ ID NO:12;
  c. the intein domain from the first component is SEQ ID NO:24 and the intein domain from the second component is SEQ ID NO:20; or
  d. the intein domain from the first component is SEQ ID NO:38 and the intein domain from the second component is SEQ ID NO:34.

11. A method for cleaving a heterologous polypeptide from an intein domain wherein the heterologous polypeptide is linked to the C-terminus of the intein domain, comprising incubating the composition of claim 8 or bringing into association the components of the kit-of-parts of claim 8 under conditions allowing intein-mediated protein cleavage.

12. A method for cleaving a heterologous polypeptide from an intein domain wherein the heterologous polypeptide is linked to the N-terminus of the intein domain, comprising incubating the composition of claim 9 or bringing into association the components of the kit-of-parts of claim 9 under conditions allowing intein-mediated protein cleavage.

13. A method for covalently linking the N-terminus of a first polypeptide to the C-terminus of a second polypeptide comprising incubating the composition of claim 10 or bringing into association the components of the kit-of-parts of claim 10 under conditions allowing intein splicing wherein said first polypeptide is the heterologous polypeptide which forms part of the first component and said second polypeptide is the heterologous polypeptide which forms part of the second component.

14. A method for cyclizing a heterologous polypeptide comprising incubating a fusion protein comprising a first intein domain, a second intein domain, and a heterologous polypeptide, wherein the heterologous polypeptide is N-terminal to the first intein domain, and wherein the heterologous polypeptide is C-terminal to the second intein domain and wherein
  (a) the first intein domain is SEQ ID NO:3 and the second intein domain is SEQ ID NO:7;
  (b) the first intein domain is SEQ ID NO:12 and the second intein domain is SEQ ID NO:16;
  (c) the first intein domain is SEQ ID NO:20 and the second intein domain is SEQ ID NO:24; or
  (d) the first intein domain is SEQ ID NO:34 and the second intein domain is SEQ ID NO:38, under conditions allowing intein splicing, wherein the heterologous polypeptide is the heterologous polypeptide that forms part of the fusion protein.

* * * * *